US012110272B2

(12) United States Patent
Nivorozhkin et al.

(10) Patent No.: US 12,110,272 B2
(45) **Date of Patent: *Oct. 8, 2024**

(54) DEUTERATED TRYPTAMINE DERIVATIVES AND METHODS OF USE

(71) Applicant: CYBIN IRL LIMITED, Dublin (IE)

(72) Inventors: Alex Nivorozhkin, West Roxbury, MA (US); Michael Palfreyman, St. Petersburg, FL (US)

(73) Assignee: Cybin IRL Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,492

(22) Filed: Jul. 17, 2023

(65) Prior Publication Data

US 2023/0357147 A1 Nov. 9, 2023

Related U.S. Application Data

(63) Continuation of application No. 17/974,007, filed on Oct. 26, 2022, now Pat. No. 11,746,088, which is a continuation of application No. PCT/IB2021/054340, filed on May 19, 2021.

(60) Provisional application No. 63/157,118, filed on Mar. 5, 2021, provisional application No. 63/114,738, filed on Nov. 17, 2020, provisional application No. 63/026,939, filed on May 19, 2020.

(51) Int. Cl.
*C07D 209/16* (2006.01)
*A61K 9/20* (2006.01)
*A61K 31/4045* (2006.01)

(52) U.S. Cl.
CPC .............. *C07D 209/16* (2013.01); *A61K 9/20* (2013.01); *A61K 9/2054* (2013.01); *A61K 31/4045* (2013.01); *C07B 2200/05* (2013.01); *C07B 2200/07* (2013.01)

(58) Field of Classification Search
CPC ...... C07D 209/16; A61K 9/20; C07B 2200/05
See application file for complete search history.

(56) References Cited

U.S. PATENT DOCUMENTS 3,072,530 A 1/1963 Albert et al.
3,078,214 A 2/1963 Albert et al.
3,192,111 A 6/1965 Hoffman et al.
3,444,174 A 5/1969 Remers et al.
3,686,213 A 8/1972 Poletto et al.
4,855,325 A 8/1989 Naftchi
4,861,760 A 8/1989 Mazuel et al.
4,911,920 A 3/1990 Jani et al.
5,158,956 A 10/1992 Gidda et al.
5,212,162 A 5/1993 Missel et al.
5,258,379 A 11/1993 Gidda et al.
5,403,841 A 4/1995 Lang et al.
5,417,987 A 5/1995 Dietz et al.
5,594,034 A 1/1997 Gidda et al.
6,107,499 A 8/2000 Shashoua
6,207,396 B1 3/2001 Sigler
6,306,616 B1 10/2001 Shindelman
6,376,531 B1 4/2002 Bell
6,403,808 B1 6/2002 Glennon et al.
6,407,137 B2 6/2002 Shashoua
6,815,212 B2 11/2004 Ness et al.
7,052,846 B2 5/2006 Van Ness et al.
7,642,344 B2 1/2010 Van Ness et al.
7,745,665 B2 6/2010 Gant et al.
8,980,880 B1 3/2015 King et al.
9,139,821 B2 9/2015 Nazor et al.
9,226,925 B1 1/2016 King et al.
9,421,266 B2 8/2016 King et al.
9,435,816 B2 9/2016 Johansen et al.
9,458,082 B2 10/2016 Gant et al.
9,775,379 B2 10/2017 Davidson et al.
9,839,241 B2 12/2017 Davidson et al.
9,974,743 B2 5/2018 Rose et al.
10,015,979 B2 7/2018 Shchepinov
(Continued)

FOREIGN PATENT DOCUMENTS

AT 501069 3/2011
AU 3230299 12/1999
(Continued)

OTHER PUBLICATIONS 5-methoxy DMT (5-methoxy-N, N-Dimethyltryptamine, 5-MeO DMT, CAS No. 1019-45-0)1 Cayman Chemical, Retrieved from the internet: https://www.caymanchem.com/product/11480/5-methoxy-dmt#:-:text=5-methoxyDMT is a,(5-HT) receptors.&text=5methoxy DMT is regulated,is intended for forensic applications., Jan. 26, 2022.
Barker et al, "Comparison of the brain levels of N,N-dimethyltryptamine and a,a,I3,I3-tetradeutero-N,N-dimethyltryptamine following intraperitoneal injection: The In Vivo kinetic isotope effect", Biochemical Pharmacology, vol. 31, No. 15, pp. 2513-2516, Aug. 1, 1982.
(Continued)

*Primary Examiner* — Kamal A Saeed
(74) *Attorney, Agent, or Firm* — Lathrop GPM LLP; Lisa Hillman

(57) ABSTRACT

The present disclosure is directed to chemical compounds and to the use of such compounds in the treatment of diseases associated with a serotonin 5-$HT_2$ receptor.

Formula (III)

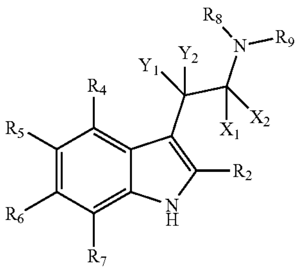

18 Claims, No Drawings

(56) References Cited

U.S. PATENT DOCUMENTS

| | | | |
|---|---|---|---|
| 10,183,001 | B1 | 1/2019 | King et al. |
| 10,519,175 | B2 | 12/2019 | Londesbrough et al. |
| 10,668,030 | B2 | 6/2020 | Dwoskin et al. |
| 10,721,963 | B2 | 7/2020 | Thorens et al. |
| 10,722,479 | B2 | 7/2020 | Zhang |
| 10,729,706 | B2 | 8/2020 | Kucuksen et al. |
| 10,738,268 | B2 | 8/2020 | Leo |
| 10,933,073 | B2 | 3/2021 | Chadeayne |
| 11,000,534 | B1 | 5/2021 | Sippy |
| 11,136,293 | B2 | 10/2021 | Protzko |
| 11,242,318 | B2 | 2/2022 | Nivorozhkin et al. |
| 11,312,684 | B1 | 4/2022 | Nichols et al. |
| 11,324,762 | B2 | 5/2022 | Sippy |
| 11,471,417 | B2 | 10/2022 | Rands et al. |
| 11,680,043 | B2 | 6/2023 | Nichols et al. |
| 11,724,985 | B2 | 8/2023 | Nivorozhkin et al. |
| 11,746,088 | B2 | 9/2023 | Nivorozhkin et al. |
| 11,834,410 | B2 | 12/2023 | Nivorozhkin et al. |
| 11,958,807 | B2 | 4/2024 | Nivorozhkin et al. |
| 2001/0008641 | A1 | 7/2001 | Krotzer |
| 2003/0007961 | A1 | 1/2003 | Wilburn |
| 2003/0078231 | A1 | 4/2003 | Wilburn |
| 2003/0096013 | A1 | 5/2003 | Werling et al. |
| 2004/0105881 | A1 | 6/2004 | Cevc et al. |
| 2004/0132800 | A1 | 7/2004 | Chen et al. |
| 2004/0180147 | A1 | 9/2004 | Parikh et al. |
| 2004/0258617 | A1 | 12/2004 | Weber et al. |
| 2005/0288616 | A1 | 12/2005 | Bozenbury et al. |
| 2006/0192098 | A1 | 8/2006 | Danylewych-May |
| 2008/0045588 | A1 | 2/2008 | Gant et al. |
| 2008/0010318 | A1 | 5/2008 | Gant et al. |
| 2008/0103189 | A1 | 5/2008 | Gant |
| 2008/0194553 | A1 | 8/2008 | Gillessen |
| 2008/0220441 | A1 | 9/2008 | Birnbaum et al. |
| 2008/0221170 | A1 | 9/2008 | Roberts et al. |
| 2008/0227830 | A1 | 9/2008 | Roberts et al. |
| 2008/0241255 | A1 | 10/2008 | Rose et al. |
| 2009/0023765 | A1 | 1/2009 | Gant et al. |
| 2009/0028796 | A1 | 1/2009 | Bednarek et al. |
| 2009/0093513 | A1 | 4/2009 | Hamann et al. |
| 2009/0197822 | A1 | 8/2009 | Griffin |
| 2009/0286760 | A1 | 11/2009 | Chen |
| 2009/0318527 | A1 | 12/2009 | Sard et al. |
| 2010/0137616 | A1 | 6/2010 | Sard et al. |
| 2010/0292448 | A1 | 11/2010 | Nilssen |
| 2011/0060037 | A1 | 3/2011 | Woldbye et al. |
| 2011/0207627 | A1 | 8/2011 | Liotta |
| 2012/0108510 | A1 | 5/2012 | Young |
| 2012/0156139 | A1 | 6/2012 | Katz-Brull |
| 2012/0183600 | A1 | 7/2012 | Chen |
| 2013/0210167 | A1 | 8/2013 | Benchikh et al. |
| 2013/0303735 | A1 | 11/2013 | Epshtein et al. |
| 2014/0066881 | A1 | 3/2014 | Freeman |
| 2014/0242722 | A1 | 8/2014 | Knop et al. |
| 2014/0256688 | A1 | 9/2014 | Lozinsky et al. |
| 2014/0349976 | A1 | 11/2014 | Hacksell |
| 2015/0343144 | A1 | 12/2015 | Altschul et al. |
| 2016/0022930 | A1 | 1/2016 | Greim et al. |
| 2016/0067711 | A1 | 3/2016 | Yoon et al. |
| 2016/0120220 | A1 | 5/2016 | Malgat et al. |
| 2016/0250201 | A1 | 9/2016 | Rose et al. |
| 2016/0309784 | A1 | 10/2016 | Charles et al. |
| 2016/0338945 | A1 | 11/2016 | Knight |
| 2017/0100341 | A1 | 4/2017 | Tygesen et al. |
| 2017/0173262 | A1 | 6/2017 | Veltz |
| 2017/0210704 | A1 | 7/2017 | Campbell |
| 2017/0281652 | A1 | 10/2017 | Altschul et al. |
| 2017/0313666 | A1 | 11/2017 | Wu et al. |
| 2017/0348303 | A1 | 12/2017 | Bosse et al. |
| 2018/0021326 | A1 | 1/2018 | Stamets |
| 2018/0043113 | A1 | 2/2018 | Hogwood et al. |
| 2018/0147142 | A1 | 5/2018 | Knight |
| 2018/0221396 | A1 | 8/2018 | Chadeayne |
| 2018/0289905 | A1 | 10/2018 | Hogwood et al. |
| 2018/0343812 | A1 | 12/2018 | Leo |
| 2018/0354995 | A1 | 12/2018 | Gudkov et al. |
| 2019/0119310 | A1 | 4/2019 | Londesbrough |
| 2019/0142851 | A1 | 5/2019 | Chadeayne |
| 2019/0246591 | A1 | 8/2019 | Leo |
| 2019/0254988 | A1 | 8/2019 | Archibald |
| 2019/0350949 | A1 | 11/2019 | Kocoksen et al. |
| 2020/0030309 | A1 | 1/2020 | Olson |
| 2020/0060997 | A1 | 2/2020 | Goren |
| 2020/0114005 | A1 | 4/2020 | Fernandes et al. |
| 2020/0147038 | A1 | 5/2020 | Russ et al. |
| 2020/0179349 | A1 | 5/2020 | Yun et al. |
| 2020/0172469 | A1 | 6/2020 | Gant et al. |
| 2020/0229411 | A1 | 7/2020 | Leo |
| 2020/0230128 | A1 | 7/2020 | Bosse et al. |
| 2020/0237683 | A1 | 7/2020 | Whalley et al. |
| 2020/0290992 | A1 | 9/2020 | Zhang |
| 2020/0331939 | A1 | 10/2020 | Londesbrough et al. |
| 2020/0370073 | A1 | 11/2020 | Leo |
| 2020/0375967 | A1 | 12/2020 | Stamets |
| 2020/0390746 | A1 | 12/2020 | Rands et al. |
| 2020/0397752 | A1 | 12/2020 | Perez Castillo et al. |
| 2021/0000803 | A1 | 1/2021 | Sharp et al. |
| 2021/0015738 | A1 | 1/2021 | Larosa et al. |
| 2021/0015833 | A1 | 1/2021 | Larosa et al. |
| 2021/0023052 | A1 | 1/2021 | Chadeayne |
| 2021/0030787 | A1 | 2/2021 | Goren |
| 2021/0069170 | A1 | 3/2021 | Stamets |
| 2021/0085671 | A1 | 3/2021 | Chadeayne |
| 2021/0113644 | A1 | 4/2021 | Chadeayne |
| 2021/0137137 | A1 | 5/2021 | Leo |
| 2021/0137854 | A1 | 5/2021 | Goren |
| 2021/0137908 | A1 | 5/2021 | Kristensen et al. |
| 2021/0145851 | A1 | 5/2021 | Stamets |
| 2021/0147888 | A1 | 5/2021 | Vogan et al. |
| 2021/0183519 | A1 | 6/2021 | Shlomi |
| 2021/0236523 | A1 | 8/2021 | Schindler et al. |
| 2021/0251157 | A1 | 8/2021 | Leo |
| 2021/0267966 | A1 | 9/2021 | Petcavich |
| 2021/0267985 | A1 | 9/2021 | Horn |
| 2021/0268036 | A1 | 9/2021 | Hsiao et al. |
| 2021/0275618 | A1 | 9/2021 | Davidson et al. |
| 2021/0292278 | A1 | 9/2021 | Chadeayne |
| 2021/0300870 | A1 | 9/2021 | Chadeayne |
| 2021/0308200 | A1 | 10/2021 | Stamets |
| 2021/0322306 | A1 | 10/2021 | Espinoza et al. |
| 2021/0322447 | A1 | 10/2021 | Plakogiannis |
| 2021/0363104 | A1 | 11/2021 | Nivorozhkin et al. |
| 2021/0378969 | A1 | 12/2021 | Rands et al. |
| 2021/0395201 | A1 | 12/2021 | Rands et al. |
| 2021/0403426 | A1 | 12/2021 | Rands et al. |
| 2022/0017549 | A1 | 1/2022 | Slassi et al. |
| 2022/0017550 | A1 | 1/2022 | Slassi et al. |
| 2022/0024956 | A1 | 1/2022 | Slassi et al. |
| 2022/0062237 | A1 | 3/2022 | Layzell et al. |
| 2022/0071958 | A1 | 3/2022 | Terwey |
| 2022/0105041 | A1 | 4/2022 | Lubda et al. |
| 2022/0110955 | A1 | 4/2022 | Sippy |
| 2022/0119346 | A1 | 4/2022 | Nivorozhkin et al. |
| 2022/0168275 | A1 | 6/2022 | Rands et al. |
| 2022/0280482 | A1 | 9/2022 | Barrow et al. |
| 2022/0281818 | A1 | 9/2022 | Rands et al. |
| 2022/0313660 | A1 | 10/2022 | Layzell et al. |
| 2022/0370413 | A1 | 11/2022 | Barrow et al. |
| 2023/0066286 | A1 | 3/2023 | Nivorozhkin et al. |
| 2023/0126298 | A1 | 4/2023 | Nivorozhkin et al. |
| 2023/0202979 | A1 | 6/2023 | Nivorozhkin et al. |
| 2023/0219889 | A1 | 7/2023 | Nivorozhkin et al. |
| 2023/0285359 | A1 | 9/2023 | Barrow et al. |
| 2023/0357144 | A1 | 11/2023 | Nichols et al. |
| 2023/0357147 | A1 | 11/2023 | Nivorozhkin et al. |
| 2024/0067605 | A1 | 2/2024 | Nivorozhkin et al. |

FOREIGN PATENT DOCUMENTS

| | | | |
|---|---|---|---|
| AU | 2007209313 | A1 | 8/2007 |
| AU | 2009214724 | A1 | 8/2009 |
| AU | 2014202047 | A1 | 5/2014 |
| AU | 2018203524 | A1 | 6/2018 |

(56) References Cited

FOREIGN PATENT DOCUMENTS

| | | | |
|---|---|---|---|
| AU | 20210215274 1 | | 9/2021 |
| CA | 672478 | A | 10/1963 |
| CA | 2338326 | A1 | 2/2000 |
| CA | 2422730 | A1 | 3/2002 |
| CA | 2487849 | A1 | 1/2004 |
| CA | 2489410 | A1 | 1/2004 |
| CA | 2498938 | A1 | 4/2004 |
| CA | 2686723 | A1 | 11/2008 |
| CA | 2758774 | A1 | 10/2010 |
| CA | 2796883 | A1 | 11/2011 |
| CA | 2816595 | A1 | 4/2012 |
| CA | 2838667 | A1 | 4/2012 |
| CA | 2812063 | A1 | 6/2012 |
| CA | 2909633 | A1 | 9/2014 |
| CA | 2952818 | A1 | 11/2016 |
| CA | 3050679 | A1 | 7/2018 |
| CA | 3051914 | A1 | 8/2018 |
| CA | 3052974 | A1 | 8/2018 |
| CA | 3079560 | A1 | 4/2019 |
| CA | 3099293 | A1 | 11/2019 |
| CA | 3127854 | A1 | 8/2020 |
| CA | 3088384 | A1 | 10/2020 |
| CN | 1450065 | A | 10/2003 |
| CN | 1688288 | A | 10/2005 |
| CN | 101427140 | A | 5/2009 |
| CN | 101795621 | A | 8/2010 |
| CN | 102115455 | A | 7/2011 |
| CN | 102724913 | A | 10/2012 |
| CN | 103816150 | A | 5/2014 |
| CN | 204576485 | A | 8/2015 |
| CN | 105706423 | A | 6/2016 |
| CN | 105792942 | A | 7/2016 |
| CN | 106692144 | A | 5/2017 |
| CN | 107095680 | A | 8/2017 |
| CN | 107771056 | A | 3/2018 |
| CN | 107949314 | A | 4/2018 |
| CN | 108619214 | A | 10/2018 |
| CN | 108929259 | A | 12/2018 |
| CN | 109069073 | A | 12/2018 |
| CN | 109890371 | A | 6/2019 |
| CN | 110049723 | A | 7/2019 |
| CN | 110325954 | A | 10/2019 |
| CN | 209606445 | U | 11/2019 |
| CN | 110996775 | A | 4/2020 |
| CN | 112430187 | A | 3/2021 |
| CS | 276073 | B6 | 3/1992 |
| CZ | 2015962 | A3 | 7/2017 |
| DE | 255749 | A1 | 4/1988 |
| DE | 265636 | A1 | 3/1989 |
| DE | 102016014603 | A1 | 1/2018 |
| EP | 0152379 | A2 | 8/1985 |
| EP | 0850320 | A2 | 7/1998 |
| EP | 0962464 | A2 | 12/1999 |
| EP | 0990047 | A2 | 4/2000 |
| EP | 1693366 | A1 | 8/2006 |
| EP | 0992511 | B1 | 3/2009 |
| EP | 3698260 | A1 | 8/2020 |
| EP | 3713568 | A1 | 9/2020 |
| EP | 3826632 | A1 | 6/2021 |
| EP | 3844147 | A1 | 7/2021 |
| EP | 3873883 | A1 | 9/2021 |
| ES | 2355024 | A1 | 3/2011 |
| FI | 34529 | A | 10/1964 |
| FR | 2448540 | A1 | 9/1980 |
| GB | 672478 | | 5/1952 |
| GB | 912715 | | 8/1959 |
| GB | 911946 | A1 | 12/1962 |
| GB | 912714 | A | 12/1962 |
| GB | 981192 | A | 1/1965 |
| GB | 982738 | A | 2/1965 |
| GB | 1264610 | A | 2/1972 |
| GB | 2586940 | A | 3/2021 |
| GB | 2588505 | A | 4/2021 |
| GB | 2585978 | A | 7/2021 |
| GB | 2592822 | A | 9/2021 |

| | | | |
|---|---|---|---|
| GB | 202107702 | A | 9/2021 |
| GB | 2595776 | A | 12/2021 |
| GB | 202106881 | A | 12/2021 |
| HU | 0400250 | A2 | 8/2004 |
| IN | 201721041262 | A | 11/2017 |
| JP | H0827020 | A | 1/1996 |
| JP | H0827029 | A | 1/1996 |
| JP | 2005-031029 | A | 2/2005 |
| JP | 2008-183012 | A | 8/2008 |
| JP | 4786653 | B2 | 10/2011 |
| KR | 20110028361 | A | 3/2011 |
| KR | 20110115128 | A | 10/2011 |
| KR | 20150046994 | A | 5/2015 |
| MX | PA01005905 | A | 9/2002 |
| PT | 879054 | E | 3/2008 |
| RU | 2005101344 | A | 8/2005 |
| RU | 2005101343 | C2 | 3/2008 |
| SG | 10201705968 | A | 8/2017 |
| SG | 10201707484 | U | 10/2017 |
| TW | 201103937 | A | 2/2011 |
| TW | 201242600 | A | 11/2012 |
| TW | 201605856 | A | 2/2016 |
| TW | 202045477 | A | 12/2020 |
| TW | 202103699 | A | 2/2021 |
| TW | 202128610 | A | 8/2021 |
| WO | WO 1991/001756 | A1 | 2/1991 |
| WO | WO 1995/001334 | A1 | 1/1995 |
| WO | WO 1998/026644 | A2 | 6/1998 |
| WO | WO 1999/042840 | A1 | 8/1999 |
| WO | WO 2000/003679 | A2 | 1/2000 |
| WO | WO 2001/095903 | A1 | 12/2001 |
| WO | WO 2002/005851 | A2 | 1/2002 |
| WO | WO 2002/036113 | A1 | 5/2002 |
| WO | WO 2002/036114 | A1 | 5/2002 |
| WO | WO 2002/102988 | A2 | 12/2002 |
| WO | WO 2003/016903 | A2 | 2/2003 |
| WO | WO 2004/025268 | A2 | 3/2004 |
| WO | WO 2004/054500 | A2 | 7/2004 |
| WO | WO 2006/086978 | A2 | 8/2006 |
| WO | WO 2007/024741 | A2 | 3/2007 |
| WO | WO 2007/097754 | A1 | 8/2007 |
| WO | WO 2007/110637 | A1 | 10/2007 |
| WO | WO 2008/003028 | A2 | 1/2008 |
| WO | WO 2008/016677 | A2 | 2/2008 |
| WO | WO 2008/016677 | A3 | 3/2008 |
| WO | WO 2008/121610 | A1 | 10/2008 |
| WO | WO 2008/122990 | A1 | 10/2008 |
| WO | WO 2008/130638 | A2 | 10/2008 |
| WO | WO 2009/021055 | A1 | 2/2009 |
| WO | WO 2009/097596 | A1 | 8/2009 |
| WO | WO 2009/140680 | A1 | 11/2009 |
| WO | WO 2010/033724 | A2 | 3/2010 |
| WO | WO 2010/124089 | A2 | 10/2010 |
| WO | WO 2010/151258 | A1 | 12/2010 |
| WO | WO 2011/028875 | A1 | 3/2011 |
| WO | WO 2011/140607 | A1 | 11/2011 |
| WO | WO 2011/140608 | A1 | 11/2011 |
| WO | WO 2012/005951 | A1 | 1/2012 |
| WO | WO 2012/058337 | A2 | 5/2012 |
| WO | WO 2012/058769 | A1 | 5/2012 |
| WO | WO 2012/134436 | A1 | 10/2012 |
| WO | WO 2012/139042 | A2 | 10/2012 |
| WO | WO 2013/022775 | A1 | 2/2013 |
| WO | WO 2013/032940 | A1 | 3/2013 |
| WO | WO 2013/064690 | A1 | 5/2013 |
| WO | WO 2014/004460 | A1 | 1/2014 |
| WO | WO 2014/026044 | A2 | 2/2014 |
| WO | WO 2014/064703 | A1 | 5/2014 |
| WO | WO 2014/070424 | A1 | 5/2014 |
| WO | WO 2014/078374 | A | 5/2014 |
| WO | WO 2014/144712 | A1 | 9/2014 |
| WO | WO 2014/146091 | A1 | 9/2014 |
| WO | WO 2014/152182 | A1 | 9/2014 |
| WO | WO 2014/152663 | A1 | 9/2014 |
| WO | WO 2015/066344 | A1 | 5/2015 |
| WO | WO 2015/073459 | A1 | 5/2015 |
| WO | WO 2015/073588 | A1 | 5/2015 |
| WO | WO 2015/090583 | A1 | 6/2015 |
| WO | WO 2015/094981 | A1 | 6/2015 |

(56) References Cited

FOREIGN PATENT DOCUMENTS

WO WO 2015/122964 A1 8/2015
WO WO 2015/127556 A1 9/2015
WO WO 2015/127558 A1 9/2015
WO WO 2015/164541 A1 10/2015
WO WO 2016/033204 A2 3/2016
WO WO 2016/057343 A1 4/2016
WO WO 2016/138135 A1 9/2016
WO WO 2016/161138 A1 10/2016
WO WO 2017/044702 A1 3/2017
WO WO 2017/112398 A1 6/2017
WO WO 2017/189528 A1 11/2017
WO WO 2018/031803 A1 2/2018
WO WO 2018/049167 A1 3/2018
WO WO 2018/057576 A1 3/2018
WO WO 2018/064465 A1 4/2018
WO WO 2018/089375 A1 5/2018
WO WO 2018/106738 A1 6/2018
WO WO 2018/135943 A1 7/2018
WO WO 2018/136610 A1 7/2018
WO WO 2018/145219 A1 8/2018
WO WO 2018/148605 A1 8/2018
WO WO 2018/195455 A1 10/2018
WO WO 2018/204764 A1 11/2018
WO WO 2018/207192 A1 11/2018
WO WO 2018/223044 A1 12/2018
WO WO 2019/018735 A1 1/2019
WO WO 2019/021158 A1 1/2019
WO WO 2019/058145 A1 3/2019
WO WO 2019/073379 A1 4/2019
WO WO 2019/079742 A1 4/2019
WO WO 2019/081764 A1 5/2019
WO WO 2019/099745 A1 5/2019
WO WO 2019/109124 A1 6/2019
WO WO 2019/122525 A1 6/2019
WO WO 2019/173797 A1 9/2019
WO WO 2019/241451 A1 12/2019
WO WO 2020/023084 A1 1/2020
WO WO 2020/219461 A1 1/2020
WO WO 2020/024060 A1 2/2020
WO WO 2020/024071 A1 2/2020
WO WO 2020/041329 A1 2/2020
WO WO 2012/058337 A1 3/2020
WO WO 2020/053196 A1 3/2020
WO WO 2020/148442 A1 7/2020
WO WO 2020/157569 A1 8/2020
WO WO 2020/169850 A1 8/2020
WO WO 2020/169851 A1 8/2020
WO WO 2020/176597 A1 9/2020
WO WO 2020/181194 A1 9/2020
WO WO 2020/185581 A1 9/2020
WO WO 2020/212948 A1 10/2020
WO WO 2020/212951 A1 10/2020
WO WO 2020/245133 A1 12/2020
WO WO 2020/247632 A1 12/2020
WO WO 2020/260917 A1 12/2020
WO WO 2020/264390 A2 12/2020
WO WO 2021/000053 A1 1/2021
WO WO 2021/000054 A1 1/2021
WO WO 2021/000997 A1 1/2021
WO WO 2021/003467 A1 1/2021
WO WO 2021/007659 A1 1/2021
WO WO 2021/007660 A1 1/2021
WO WO 2021/007661 A1 1/2021
WO WO 2021/007662 A1 1/2021
WO WO 2021/007663 A1 1/2021
WO WO 2021/009374 A1 1/2021
WO WO 2021/016423 A1 1/2021
WO WO 2021/016710 A1 2/2021
WO WO 2021/030571 A1 2/2021
WO WO 2021/038112 A2 3/2021
WO WO 2021/041407 A1 3/2021
WO WO 2021/052989 A1 3/2021
WO WO 2021/062557 A1 4/2021
WO WO 2021/062559 A1 4/2021
WO WO 2021/067262 A1 4/2021
WO WO 2021/067626 A2 4/2021
WO WO 2021/072530 A1 4/2021
WO WO 2021/076572 A1 4/2021
WO WO 2021/076849 A1 4/2021
WO WO 2021/081138 A1 4/2021
WO WO 2021/086513 A1 5/2021
WO WO 2021/089872 A1 5/2021
WO WO 2021/089873 A1 5/2021
WO WO 2021/102567 A1 6/2021
WO WO 2021/102568 A1 6/2021
WO WO 2021/102569 A1 6/2021
WO WO 2021/108911 A1 6/2021
WO WO 2021/113958 A1 6/2021
WO WO 2021/113959 A1 6/2021
WO WO 2021/113986 A1 6/2021
WO WO 2021/116503 A2 6/2021
WO WO 2021/138564 A1 7/2021
WO WO 2021/142238 A1 7/2021
WO WO 2021/155467 A1 8/2021
WO WO 2021/155468 A2 8/2021
WO WO 2021/155470 A1 8/2021
WO WO 2021/159213 A1 8/2021
WO WO 2021/168082 A1 8/2021
WO WO 2021/173989 A1 9/2021
WO WO 2021/178579 A1 9/2021
WO WO 2021/179091 A1 9/2021
WO WO 2021/183490 A1 9/2021
WO WO 2021/188782 A1 9/2021
WO WO 2021/188812 A1 9/2021
WO WO 2021/188870 A1 9/2021
WO WO 2021/207137 A1 10/2021
WO WO 2021/207824 A1 10/2021
WO WO 2021/209815 A1 10/2021
WO WO 2021/234608 A1 11/2021
WO WO 2021/244831 A1 12/2021
WO WO 2022/016289 A1 1/2022
WO WO 2022/023812 A1 2/2022
WO WO 2022/038170 A1 2/2022
WO WO 2022/038171 A1 2/2022
WO WO 2022/043227 A1 3/2022
WO WO 2022/069690 A2 4/2022
WO WO 2022/076642 A1 4/2022
WO WO 2022/094719 A1 5/2022
WO WO 2022/117359 A1 6/2022
WO WO 2022/173888 A1 8/2022
WO WO 2022/183287 A1 9/2022
WO WO 2022/192097 A1 9/2022
WO WO 2022/195011 A1 9/2022
WO WO 2022/246572 A1 12/2022
WO WO 2023/036473 A1 3/2023

OTHER PUBLICATIONS

Barker et al, "Distribution of the hallucinogens N,N-dimethyltryptamine and 5-methoxy-N,N-dimethyltryptamine in rat brain following intraperitoneal injection: application of a new solid-phase extraction LC-APcl-MS-MS-isotope dilution method", J. Chromatogr. B, vol. 751, pp. 37-47, Aug. 3, 2000.

Barker et al, "In vivo metabolism of a,a,I3,I3-tetradeutero-n, N-dimethyltryptamine in rodent brain", Biochemical Pharmacology vol. 33, No. 9, pp. 1395-1400, May 1, 1984.

Barker, "N, N-Dimethyltryptamine (DMT), an Endogenous Hallucinogen: Past, Present, and Future Research to Determine Its Role and Function", Frontiers in Neuroscience, vol. 12, No. 536, 17 pages, Aug. 6, 2018.

Bauer, "New Toad Venom Compound Synthesized for Clinical Use: 5-MeO-DMT Succinate", Psychedelic Science Review, Retrieved from the internet: https://psychedelicreview.com/new-toad-venom-compound-synthesized-for-clinical-use-5-meo-dmt-succinate/, Jan. 18, 2021.

Bauer, "The State of the Art of Psilacetin (4-AcO-DMT)", Psychedelic Science Review, Sep. 18, 2019, Retrieved from the internet: https://psychedelicreview.com/the-state-of-the-art-of-psilacetin-4-aco-dmt/.

Bauer, "Two New Crystalline Forms of Norpsilocin", Psychedelic Science Review, Retrieved from the internet: https://psychedelicreview.com/two-new-crystalline-forms-of-norpsilocin/, Apr. 23, 2020.

(56) References Cited

OTHER PUBLICATIONS

Bijlsma et al, "Fragmentation pathways of drugs of abuse and their metabolites based on QTOF MS/MS and MSE accurate—mass spectra", Journal of Mass Spectrometry, vol. 46, No. 9, pp. 865-875, Sep. 13, 2011.
Bjornstatd et al., "Development and Clinical Application of an LC-MS-MS Method for Mescaline in Urine", Journal of Analytical Toxicology, Apr. 2008, vol. 32, No. 3, pp. 227-231.
Borchardt et al., "General methods for the preparation of [alpha] and/or [beta] deuterium labelled 6-hydroxydopamine derivatives", Journal of Labelled Compounds and Radiopharmaceuticals, Mar. 1, 1982, vol. 19, No. 3, pp. 433-445.
Brandt et al., "Characterization of the synthesis of N,N-dimethyltryptamine by reductive amination using gas chromatography ion trap mass spectrometry", Drug Testing and Analysis, vol. 2, pp. 330-338, Jun. 2, 2010.
Brandt et al, "Microwave-accelerated synthesis of psychoactive deuterated N,N-dialkylated4a,a,B,B-d4]-tryptamines", Journal of Labelled Compounds and Radiopharmaceuticals, vol. 51, pp. 423-429, Nov. 3, 2008.
BusinessWire, "Cybin Advances IND-Enabling Studies of Two Psychedelic Molecules, CYB003 and CYB004 for Investigational New Drug Applications", Retrieved from the internet: https://www.businesswire.com/news/ CYB004-for-Investigational-New-Drug-Applications, Apr. 13, 2021. home/20210413005466/en/Cybin-Advances-IND-Enabling-Studies-of-Two-Psychedelic-Molecules-CYB003-and.
BusinessWire, "Cybin Announces Completion of its 51st Pre-Clinical Psychedelic Molecule Study", Retrieved from the internet: https://www.businesswire.com/news/home/20210622005438/en/Cybin-Announces-Completion-of-its-51st-Pre-Clinical-Psychedelic-Molecule-Study, Jun. 22, 2021.
Businesswire, "Lennham Pharmaceuticals Announces Issuance of U.S. Patent Covering Deuterated Psilocybin Products" www.lennham.com, May 14, 2021.
Businesswire, "Usona Institute Publishes Synthesis and Characterization of cGMP 5-MeO-DMT", Retrieved from the internet: https://www.businesswire.com/news/home/20201208005761/en/Usona-Institute-Publishes-Synthesis-and-Characterization-of-CGMP-5-MeO-DMT, Dec. 8, 2020.
Cameron et al, "A non-hallucinogenic psychedelic analogue with therapeutic potential", Nature, vol. 589, pp. 474-479, Dec. 9, 2020.
Cecil Textbook of Medicine, 20th edition (1996), vol. 2, pp. 1992-1996.
Cecil Textbook of Medicine, 20th edition (1996), vol. 2, pp. 2050-2057.
Celuch et al, "Effects of deuterium substitution on the chronotropic responses to some sympathomimetic amines in the isolated rat atria", Naunyn-Schmiedeberg's Arch Pharmacol, vol. 336, pp. 391-395, (1987).
Chadeayne et al, "Active Metabolite of Aeruginascin (4-Hydroxy-N,N,N-trimethyltryptamine): Synthesis, Structure, and Serotonergic Binding Affinity", ACS Omega, vol. 5, No. 27, pp. 16940-16943, Jul. 2, 2020.
Chadeayne et al, "Bis(4-acetoxy-N,N-dimethyltryptammonium) fumarate: a new crystalline form of psilacetin, an alternative to psilocybin as a psilocin prodrug", Crystallographic Communications, vol. E75, pp. 900-902, May 20, 2019.
Chadeayne et al, "Bis(4-hydroxy-N,N-di-n-propyltryptammonium) fumarate tetrahydrate", IUCrData, vol. 4, 3 pages, Oct. 29, 2019.
Chadeayne et al, "Bis(4-hydroxy-N-isopropyl-N-methyltryptammonium) fumarate: a new crystalline form of miprocin", Crystallographic Communications, vol. E76, pp. 517-517, Mar. 2, 2020.
Chadeayne et al, "DMT analogues: N-ethyl-N-propyltryptamine and N-allyl-N-methytryptamine as their hydrofumarate salts", Crystallographic Communications, vol. E76, pp. 1201-1205, Jun. 26, 2020.
Chadeayne et al, "Norpsilocin: freebase and fumarate salt", Crystallographic Communications, vol. E76, pp. 589-593, Mar. 23, 2020.
Chadeayne et al, "The Crystal Structure of 4-AcO-DMT Fumarate", Psychedelic Science Review, 7 pages, Mar. 25, 2019.
Chadeayne et al, "The fumarate salts of the N-isopropyl-N-methyl derivatives of DMT and psilocin", Crystallographic Communications vol. E75, pp. 1316-1320, Aug. 12, 2019.
Cheze et al, "Simultaneous analysis of six amphetamines and analogues in hair, blood and urine by LC-ESI-MS/MS: Application to the determination of MDMA after low Ecstasy intake", Forensic Science International, vol. 170, No. 2-3, pp. 100-104, Aug. 6, 2007.
Clinical Trials Arena, "Cybin gets approval to trial psilocybin for depression", Retrieved from the internet: https:// www.clinicaltrialsarena.com/news/cybin-phase-ii-psilocybin/, May 19, 2021.
Compass Pathways, "About psilocybin therapy", Retrieved from the internet: https://compasspathways.com/our -research/psilocybin-therapy/about-psilocybin-therapy/, Jan. 27, 2022.
Compass Pathways, "Compass Pathways announces positive topline results from groundbreaking phase llb trial of investigational COMP360 psilocybin therapy for treatment-resistant despression", News Release, Retrieved from the internet: https://ir.compasspathways.com/news-releases/news-release-details/compass-pathways-announces-positive-topline-results#:-:text=COMPASS%20Pathways%20plc%20(Nasdaq%3A%20CMPS,depressioncY020has%20achieved c/020itsc/020primary, Nov. 9, 2021.
Compass Pathways, "Compass Pathways granted patent covering use of its psilocybin formulation in addressing treatment-resistant depression", Retrieved from the internet: https://compasspathways.com/compass-pathways -granted-patent-covering-use-of-its-psilocybin-formulation-in-addressing-treatment-resistant-depression/, Jan. 15, 2020.
Database Caplus [online] Dec. 29, 2009, Chen: "A series of deuterium labelled phenylalkylamines as drug testing standards", XP055867027, Database accession No. 2010:371880.
Database Registry [online] Chemical Abstracts Service, Columbus, Ohio, US; Oct. 25, 2007, "Benzeneethanamine, 4-chloro-2,5-di(methoxy-d3)-", XP055866907, accession No. 1144584103 (CHEMCATS) Database accession No. 951442-78-7.
Database Registry [online] Chemical Abstracts Service, Columbus, Ohio, US; Apr. 5, 2010, "2,5-(Dimethoxy-d6)-4-iodophenethylamine Hydrochloride", XP055866911, accession No. 1819317403 (CHEMCATS) Database accession No. 1216685-82-3.
Database Registry [online] Chemical Abstracts Service, Columbus, Ohio, US; Oct. 22, 2009, "2,5-(Dimethoxy-d6)-4-methylphenethylamine Hydrochloride", XP055866918, accession No. 1725444279 (CHEMCATS) Database accession No. 1189467-51-3.
Database Registry [online] Chemical Abstracts Service, Columbus, Ohio, US; Oct. 25, 2009, "2C-B-d6 Hydrochloride", XP055866926, accession No. 2145931586 (CHEMCATS) Database accession No. 1189978-45-7.
Database Registry [online] Oct. 22, 2009, Chemcats N: "2-[4-methyl-2,5-bis(trideuteriomethoxy)phenyl]ethanamine", XP055866937, Database accession No. 1189574-92-2.
Database STN [Online] Chemical Abstracts Service, Columbus, Ohio, US; Mar. 1, 2019 (Mar. 1, 2019), Alex Kizi: "2-amino-3-(5-methoxy-2H-1,3-benzoxathiol-6-Apropanenitrile", XP055865405,accession No. AZ06532047(ON) Database No. 0797974793 CHEMCATS ; & "Azepine Product List", Mar. 1, 2019 (Mar. 1, 2019), Azepine Ltd. Suite 7777, 6 Slington House Rankine Road Basingstoke, UK.
Database STN [Online] Chemical Abstracts Service, Columbus, Ohio, US; Mar. 1, 2019 (Mar. 1, 2019), Azepine O M: "1-(5-methoxy-2H-1,3-benzoxathiol-6-yl)-2-methylpropan-2-amine", XP055865399,accession No. AZ05508757 accession No. 0103296540 CHEMCATS ; & "Azepine Product List", Azepine td. Suite 7777, & Slington House, rankine Roadd, Basingstoke, Hampshire, RG24 8PH, UK.
Database STN [Online] Chemical Abstracts Service, Columbus, Ohio, US; Mar. 1, 2019 (Mar. 1, 2019), Azepine H C: "2-(5-methoxy-2H-1,3-benzoxath iol-6-yl)propan-1-am ine", XP055865393,accession No. AZ05479357(ON) Database accession No. 1334856705 CHEMCATS ; & "Azepine Product List", Mar. 1, 2019 (Mar. 1, 2019), Azepine Ltd Suite 7777, 6 Slington House, Rankine Road, Basingstoke, Hampshire, UK.

(56) References Cited

OTHER PUBLICATIONS

Database STN [Online] Chemical Abstracts Service, Columbus, Ohio, US; Mar. 1, 2019 (Mar. 1, 2019), "[2-(5-methoxy)-2H-1,3-benzoxythiol-6-ypethyl](methyl)amine", XP055865383,accession No. AZ04786463 Database accession No. 0915409267 CHEMCATS ; & "Aurora Buildings Blocks 2", Apr. 19, 2019 (Apr. 19, 2019), Aurora Fine Chemicals LLC 7929-Silvertone Ave. Suite 609, San Diego, CA, US.
Database STN [Online] Chemical Abstracts Service, Columbus, Ohio, US; Mar. 1, 2019 (Mar. 1, 2019), "2-(5-methoxy-2H-1,3-benzoxathiol-6-ypethan-1-amine", XP055865372,accession No. AZ04784681(ON) Database accession No. 2022733918 CHEMCATS ; & "Azepine Product List", Mar. 1, 2019 (Mar. 1, 2019), Azepine Ltd 60/5 Lomonosovastr Suite 111, Kiev, Kiev Oblast, 03191 Ukraine.
Dourish et al, "Deuterium Substitution Enhances the Effects of B-Phenylethylamine on Spontaneous Motor Activity in the Rat", Pharmacology Biochemistry & Behavior, vol. 19, pp. 471-475, Mar. 3, 1983.
Ermakova et al, "A narrative synthesis of research with 5-MeO-DMT", Journal of Psychopharmacology, pp. 1-22, 2021.
European Monitoring Centre for Drugs and Drug Addiction, "Lysergide (LSD) drug profile", Retrieved from the internet: https://www.emcdda.europa.eu/publications/drug-profiles/lsd_en, Jan. 26, 2022.
FDA mulls drug to slow late-stage Alzheimer's [online], [retrieved on Sep. 23, 2003]. Retrieved from the Internet, URL; http://www.cnn.conn/2003/HEALTH/conditions/09/24/alzheimers.drug.ap/index.html.
Future4200, "A/B Extraction and Isolation of Psilocybin", Retrieved from the internet: https://future4200.com/t/a-b -extraction-and-isolation-of-psilocybin/84573, Apr. 2020.
Gal et al, "Denver just became the first city in the US to decriminalize magic mushrooms. Here's what they do to your body and mind.", Business Insider, Retrieved from the internet: https://www.businessinsider.in/denver-just-became-the-first-city-in-the-us-to-decriminalize-magic-mushrooms-heres-what-they-do-to-your-body-and-mind-/ articleshow/69258788.cms, May 10, 2019.
Gardenhire et al, "A Guide to Aerosol Delivery Devices for Respiratory Therapists", 4th Edition, 61 pages, Jan. 1, 2017.
GB Application No. 2018950.2, filed Dec. 1, 2020 to Small Pharma Ltd (34 pages).
GB Application No. 2018955.1, filed Dec. 1, 2020 to Small Pharma Ltd (59 pages).
GB Application No. 2103981.3, filed Mar. 22, 2020 to Small Pharma Ltd (87 pages).
GlobeNewswire, "Mindset Selects its Lead Clinical Candidate, MSP-1014, a Next Generation Psychedelic Medicine", Retrieved from the internet: https://www.globenewswire.com/en/news-release/2021/06/03/2241140/0/en/Mindset-Selects-its-Lead-Clinical-Candidate-MSP-1014-a-Next-Generation-Psychedelic-Medicine.html, Jun. 3, 2021.
GlobeNewswire, "Orthogonal Thinker Launches First Psychedelics Lifestyle Brand PsillyLife to Promote Psychedelic Culture and Proprietary Research", Retrieved from the internet: https://www.globenewswire.com/news -release/2019/12/02/1954840/0/en/Orthogonal-Thinker-Launches-First-Psychedelics-Lifestyle-Brand-PsillyLife-to-Promote-Psychedelic-Culture-and-Proprietary-Research.html, Dec. 2, 2019.
Gupta et al, "Heliox administration in the pediatric intensive care unit: An evidence-based review", Pediatr Crti Care Med, vol. 6, No. 2, pp. 204-211, Mar. 1, 2005.
Halberstadt et al, "Behavioral effects of a,a,B,B-tetradeuto-5-MeO-DMT in rats: comparison with 5-MeO-DMT administered in combination with a menoamine oxidase inhibitor", Psychopharmacology, vol. 221, No. 4, pp. 709-718, Jun. 2012.
Halberstadt et al, "Modification of the effects of 5-methoxy-N,N-dimethyltryptamine on exploratory behavior in rats by oxidase monoamine inhibitors", Psychopharmacology, vol. 201, No. 1, pp. 55-66, Nov. 2008.
Halberstadt, "Behavioral and Pharmacokinetic Interactions Between Monoamine Oxidase Inhibitors and the Hallucinogen 5-Methoxy-N,N-dimethyltryptamine", Pharmacol Biochem Behav, vol. 143, pp. 1-10, Apr. 2016.
Hamishehkar et al, "The Role of Carrier in Dry Powder Inhaler", Recent Advances in Novel Drug Carrier Systems, Chapter 3, pp. 39-66, (2012).
Hanan et al, "Pharmacy Practice for Technicians", Pharmaceutical Dosage Forms, Retrieved from the internet: https://www.google.nl/books/edition/Pharmacy_Practice_for_Technicians/wiBAAwAAQbAJ?hl=en&gbpv=1,Jan. 3, 2014.
Hasler et al, "Determination of psilocin and 4-hydroxyindole-3-acetic acid in plasma by HPLC-ECD and pharmacokinetic profiles of oral and intravenous psilocybin in man", Pharmaceutics Acta Helvetiae, vol. 72, pp. 175-184, Dec. 4, 1996.
Hesselgren et al, "Synthesis of Six Specifically Deuterated Indoles of Biological Interest", Journal of Labelled Compounds and Radiopharmaceuticals, vol. 17, No. pp. 411-419, May/Jun. 1980.
Heuer et al, "Administer Medications and Specialty Gases (Section III-D)", Chapter 12, Comprehensive Respiratory Therapy Exam Preparation Guide, p. 293, Feb. 22, 2020.
Innovation & Tech Today, "Cybin Advances Psilocybin as Treatment for Depression and Addiction", Retrieved from the internet: https://innotechtoday.com/cybin-advances-psilocybin-as-treatment-for-depression-and-addiction/, May 13, 2021.
International Search Report and Written Opinion for PCT International Patent Application No. PCT/EP2023/053752, dated May 11, 2023.
International Search Report and Written Opinion for PCT International Patent Application No. PCT/EP2022/058574, dated Sep. 12, 2022.
International Search Report and Written Opinion for PCT International Patent Application No. PCT/EP2021/072896, dated Feb. 4, 2022.
International Search Report and Written Opinion for PCT International Patent Application No. PCT/EP2023/053744, dated May 19, 2023.
Kargbo et al, "Direct Phosphorylation of Psilocin Enables Optimized cGMP Kilogram-Scale Manufacture of Psilocybin", ACS Omega, vol. 5, pp. 16959-16966, (2020).
Kargbo, "Psilocin Derivatives as Serotonergic Psychedelic Agents for the Treatment of CNS Disorders", ACS Medical Chemistry Letters, vol. 12, pp. 1519-1520, Aug. 12, 2021.
Lennham pharmaceuticals, "Coupling the therapeutic potential of psilocybin with compound patent protection", Retrieved from the internet: https://www.lennham.com/dpsilocybin, Jan. 27, 2022.
Lowe et al, "The Therapeutic Potential of Psilocybin", Molecules, vol. 26, 33 pages, May 15, 2021.
Ma et al, "Neurotransmitter-derived lipidoids (NT-lipidoids) for enhanced brain delivery through intravenous injection", Science Advances, vol. 6, No. 30, 11 pages, Jul. 24, 2020.
Marien, et al., "Injections of deuterated tryptamine into the nucleus accumbens of the rat: effects on locomotor activity and monoamine metabolism", Neuropharmacology (1987), 26, (10), 1481-8 (abstract)STN[databaseonline].CAPLUS [retrievedonNov. 4, 2021]. Accession No. 1987:629823.
Martin et al, "Synthesis, hydrolysis and stability of psilocin glucuronide", Forensic Science International, vol. 2387, pp. 1-6, Apr. 2014.
McKenna et al, "3, 4-Methylenedioxyamphetamine (MDA) analogues exhibit differential effects on synaptosomal release of 3H-dopamine and 3H-5-hydroxytryptamine", Pharmacology Biochemistry & Behavior, vol. 38, No. 3, pp. 505-512, Mar. 1, 1991.
Monte et al., "Dihydrobenzofuran analogues of hallucinogens. 3. Models of 4-substituted (2,5-dimethoxyphenyl)alkylamine derivatives with rigidified methoxy groups", J Med Chem., Jul. 1996, vol. 39, No. 15, pp. 2953-2961.
Monte et al., "Dihydrobenzofuran analogues of hallucinogens. 4. Mescaline derivatives", Sep. 12, 1997, vol. 40, No. 19, pp. 2997-3008.
Morris et al, "Indolealkylamine Metabolism: Synthesis of Deuterared Indolealkylamines as Metabolic Probes", Journal of Labelled Compounds and Pharmaceuticals, vol. XXXIII, No. 6, 5 pages, Oct. 8, 1992.

(56) References Cited

OTHER PUBLICATIONS

Morris et al, Synthesis of Deuterated N,N-Dimethyltryptamine (DMT) and 5-Methoxy-N,N-Dimethyltryptamine (5-MeO-DMT) J. Lab. Comp. Radiopharm., vol. 33, No. 6, pp. 455-465, (1993).
N' N-DMT (fumarate) Item No. 9003568 Cayman Chemical, Retrieved from the internet: https://www.caymanchem.com/ product/9003568/nc/o2Cn-dmt-(fumarate), Jan. 26, 2022.
N' N-DMT-d4 (fumarate) Item No. 34354 Cayman Chemical, Retrieved from the internet: https:// www.caymanchem.com/product/34354/n%2Cn-dmt-d4-(fumarate), Jan. 26, 2022.
N,N-DMT (succinate) Item No. 33586 Cayman Chemical, Retrieved from the internet: https://www.caymanchem.com/ product/33586/nc/o2Cn-dmt-(succinate)#:-:text=Productc/020Description,standardc/020categorizedc/020asc/020a%,20tryptamine.&text=Nc/o2CNc/o2DDMTc/020substitutesc/020for,twoc/02Dleverc/020drugc/020discriminationc/020test., Jan. 26, 2022.
Neonmind Webpage, "Leader in Psilocybin-Based Treatments Targeting Obesity", Retrieved from the internet: https://neonmindbiosciences.com/our-focus/#:-:text=LEADERc/020IN%20PSILOCYBIN%2DBASED%20TREATMENTS%20TARGETING%20OBESITY&text=NeonMind's%20lead%20candidate%2C%20NEO%2D001,for%20patients%20suffering%20from%20obesity., Jan. 26, 2022.
Newsfile, "Mindset Announces Milestone in New Drug Program with Successful Proof-of-Concept Animal Studies of Its Patent-Pending Psilocybin-Inspired Drug Candidates", Retrieved from the internet: https://www.newsfilecorp.com/release/74087/Mindset-Announces-Milestone-in-New-Drug-Program-with-Successful-ProofofConcept-Animal-Studies-of-Its-PatentPending-PsilocybinInspired-Drug-Candidates, Feb. 10, 2021.
Nichols et al, "Improvements to the Synthesis of the Psilocybin and a Facile Method for Preparing the O-Acetyl Prodrug of Psilocin", Synthesis, No. 6, pp. 935-938, Feb. 11, 1999.
Nichols et al., "1-(2,5-Dimethoxy-4-(trifluoromethyl)phenyl)-2-aminopropane: A Potent Serotonin 5-HT2A/2C Agonist", Journal of Medicinal Chemistry, Dec. 1, 1994, vol. 37, No. 25, pp. 4346-4351.
Olson, "Psychedelic drugs could treat depression, and other mental illnesses", UC Davis via the Conversation, Retrieved from the internet: https://www.universityofcalifornia.edu/news/psychedelic-drugs-could-treat-depression-and-other-mental-illnesses, Jun. 20, 2018.
Parkins, "Club to clinic: psychedelic drug trials aim to break new ground in mental health", Clinical Trials Arena, Retrieved from the internet: https://www.clinicaltrialsarena.com/analysis/psychedelics-psychedelic-drug-trials-aim-to-break-new-ground-in-mental-health/, Jun. 11, 2021.
PCT International Application No. PCT/EP2021/072898, International Search Report and Written Opinion of the International Searching Authority, dated Feb. 4, 2022, 26 pages.
PCT International Application No. PCT/EP2021/077057, International Search Report and Written Opinion of the International Searching Authority, dated Mar. 18, 2022, 24 pages.
PCT International Application No. PCT/IB2021/054340, International Search Report and Written Opinion of the International Searching Authority, dated Jul. 2, 2021, 13 pages.
Pham et al, "5-Methoxy-N, N-di-n-propyltrypatime (5-MeO-DPT): freebase and fumarate", Crystallographic Communications, vol. E77, pp. 522-526, Apr. 7, 2021.
Pham et al, "Psilacetin derivatives: fumarate salts of the methyl-ethyl, methyl-ally) and diallyl variants of the psilocin prodrug", Crystallographic Communications, vol. E77, pp. 101-106, Jan. 4, 2021.
Psilocin (4-hydroxy-N,N-Dimethyltryptamine, 4-hydroxy DMT, CAS No. 520-53-6) 1 Cayman Chemical, Retrieved from the internet: https://www.caymanchem.com/product/11864/4-hydroxy-dmt, Jan. 26, 2022.
Psilocin-d10 (4-hydroxy DMT-d10, 4-hydroxy-N,N-Dimethyltryptamine-d10, CAS No. 1435934-64-7)1 Cayman Chemical, Retrieved from the internet: https://www.caymanchem.com/product/31734/4-hydroxy-dmt-d10, Jan. 26, 2022.
Psilocin-D10, P-099 / P-099-1ML updated item number format, 100 µg/mL in Acetonitrile 1 Certified Reference Material, Cerilliant Analytical Reference Standards, Item Details retrieved from the internet: https://www.cerilliant.com/shopOnline/Item_Details.aspx?itemno=4973ed15-d59e-4a94-8cd4-ed45a8b6f249&item=P-099, Jan. 26, 2022.
Psilocin-d6 (4-hydroxy-N,N-Dimethyltryptamine-d6, 4-hydroxy DMT-d6) I Cayman Chemical, Retrieved from the internet: https://www.caymanchem.com/product/34780/4-hydroxy-dmt-d6, Jan. 26, 2022.
Psilocybin solution, P-097, 1.0 mg/mL in acetonitrile: water (1:1), ampule of 1 mL, certified reference material, Cerilliant®, Millipore Sigma, Retrieved from the internet: https://www.sigmaaldrich.com/US/en/product/cerillian/p097, Jan. 26, 2022.
Rands et al, WO2020245133A1, Dec. 10, 2020(abstract)STN[databaseonline].CAPLUS [retrivedonNov. 4, 2021]. Accession No. 2020:2519093.
Ray et al, "Tungstate-catalyzed oxidation of triptans with hydrogen peroxide: A novel method for the synthesis of N,N-dimethyltryptamine N-oxides", Indian Journal of Chemistry, vol. 48B, pp. 134-136, Sep. 29, 2008.
Reddit, "An experience with pure psilocin", Retrieved from the internet: https://www.reddit.com/r/psilocybin/comments/63gyly/an_experience_with_pure_psilocin/, Mar. 18, 2017.
Reid et al, "Discriminative Stimulus Properties of Beta-Phenylethylamine, Deuterated B-Phenylethylamine, Phenylethanolamine and Some Metabolites of Phenylethylamine in Rodents", Pharmacology Biochemistry & Behavior, vol. 24, pp. 1547-1553, Sep. 13, 1985.
Sammeta et al, "The hydrochloride salt of 4-hydroxy-N,N-di-n-propyltryptamine (4-HO-DPT)", IUCrData, vol. 5, 3 pages, Nov. 22, 2020.
Sepeda et al, "Inhaled 5-mthoxy-N,N-dimethyltryptamine: Supportive context associated with positive acute and enduring effects", Journal of Psychedelic Studies, vol. 4, No. 2, pp. 114-122, Nov. 28, 2019.
Sherwood et al, "Synthesis and Characterization of 5-MeO-DMT Succinate for Clinical Use". ACS Omega, vol. 5, pp. 32067-32075. Dec. 2, 2020.
Shoda et al, "Enzyme-assisted synthesis of the glucuronide conjugate of psilocin, an hallucinogenic component of magic mushrooms", Drug Testing and Analysis, vol. 3, pp. 594-596, Nov. 14, 2010.
Simmons et al, "Regioselective syntheses of deuterium labelled 6-hydroxydopamines", Journal of Labelled Compounds and Radiopharmaceuticals, Mar. 1, 1983, vol. 20, No. 3, pp. 325-338.
Simoes et al, "Dried blood spots combined to an UPLC-MS/MS method for the simultaneous determination of drugs of abuse in forensic toxicology", Journal of Pharmaceutical and Biomedical Analysis, vol. 147, pp. 634-644, Jan. 5, 2018.
Small Pharma, "Psychedelic-assisted therapy: a new approach to treating depression", Retrieved from the internet: https://www.nature.com/biopharmdeal, Jun. 2021.
SPL026 (DMT Fumarate) in Healthy Subjects and MDD Patients, NIH U.S. National Library of Medicine, ClinicalTrials.gov, Retrieved from the internet: https://clinicaltrials.gov/ct2/show/NCT04673383, Dec. 17, 2020.
Strassman, "Human psychopharmacology of N,N-dimethyltrypatamine", Behavioural Brain Research, vol. 73, pp. 121-124 (1996).
Tearavarich et al, "Microwave-accelerated preparation and analytical characterization of 5-ethoxy-N,N-dialkyl [a,a,B,B ¬H4] and [a,a,B,B-D4]-tryptamines", Drug Testing and Analysis, vol. 3, pp. 597-608, Sep. 19, 2010.
The Oregon Psilocybin Evidence Review Writing Group (Abbas et al), "Oregon Psilocybin Advisory Board Rapid Evidence Review and Recommendations", 40 pages, Jul. 30, 2021.
Trachsel et al, "Synthesis of fluoro analogues of 3, 4—(methylenedioxy) amphetamine (MDA) and its derivatives", Chemistry & Biodiversity vol. 3, No. 3, pp. 326-336, Mar. 1, 2006.
U.S. Appl. No. 17/108,679, filed Dec. 1, 2020.
U.S. Appl. No. 17/108,938, filed Dec. 1, 2020.
U.S. Appl. No. 17/208,583, filed Mar. 22, 2021.
U.S. Appl. No. 17/320,155, filed May 13, 2021.
U.S. Appl. No. 17/459,284, filed Aug. 27, 2021.

(56) References Cited

OTHER PUBLICATIONS

U.S. Appl. No. 17/108,679, filed Dec. 1, 2020 to Small Pharma Ltd (60 pages).
U.S. Appl. No. 17/108,938, filed Dec. 1, 2020 to Small Pharma Ltd (76 pages).
U.S. Appl. No. 17/208,583, filed Mar. 22, 2021 to Small Pharma Ltd (91 pages).
Walker et al, "Identification of N,N-dimethyltryptamine as the product of an in vitro enzymic methylation", Analytical Biochemistry vol. 47, No. 1, pp. 228-234, May 1972.
Xu et al, "Synthesis of deuterium labeled standards of 5-methoxy-N,N-dimethyltryptamine (5-Meo-DMT)", Journal of Labelled Compounds and Pharmaceuticals, vol. 49, No. 10, pp. 897-902, Sep. 2006.
Xu et al., "Synthesis of deuterium labeled phenethylamine derivatives", Journal of Labelled Compounds and Radiopharmaceuticals, Jan. 1, 2006, vol. 49, No. 13, pp. 1187-1200.
Yahoo! Finance, Cybin Inc. Stock, Retrieved from the internet: https://finance.yahoo.com/quote/CYBN/, Jan. 26, 2022.
Yu et al, "Deuterium Isotope Effects on the Enzymatic Oxidative Deamination of Trace Amines", Biochemical Pharmacology, vol. 30, No. 22, pp. 3089-3094, Apr. 6, 1981.
U.S. Appl. No. 17/394,038 2021/0363104 U.S. Pat. No. 11,242,318, filed Aug. 4, 2021 Nov. 25, 2021 Feb. 8, 2022, Alex Nivorozhkin, Deuterated Tryptamine Derivatives and Methods of Use.
U.S. Appl. No. 17/564,707 2022/0119346 U.S. Pat. No. 11,724,985, filed Dec. 29, 2021 Apr. 21, 2022 Aug. 15, 2023, Alex Nivorozhkin, Deuterated Tryptamine Derivatives and Methods of Use.
U.S. Appl. No. 17/974,007 2023/0066286 U.S. Pat. No. 11,746,088, filed Oct. 26, 2022 Mar. 2, 2023 Sep. 5, 2023, Alex Nivorozhkin, Deuterated Tryptamine Derivatives and Methods of Use.
U.S. Appl. No. 18/172,691 2023/0202979 U.S. Pat. No. 11,834,410, filed Feb. 22, 2023 Jun. 29, 2023 Dec. 5, 2023, Alex Nivorozhkin, Deuterated Tryptamine Derivatives and Methods of Use.
U.S. Appl. No. 18/493,231 2024/0067605 U.S. Pat. No. 11,958,807, filed Oct. 24, 2023 Feb. 29, 2024 Apr. 16, 2024, Alex Nivorozhkin, Deuterated Tryptamine Derivatives and Methods of Use.
U.S. Appl. No. 18/600,018, filed Mar. 8, 2024, Alex Nivorozhkin, Deuterated Tryptamine Derivatives and Methods of Use.
U.S. Appl. No. 17/999,310 2023/0219889, filed May 19, 2021 Jul. 13, 2023, Alex Nivorozhkin, Deuterated Tryptamine Derivatives and Methods of Use.
U.S. Appl. No. 18/056,958 2023/0126298, filed Nov. 18, 2022 Apr. 27, 2023, Alex Nivorozhkin, Deuterated Tryptamine Derivative Formulations and Methods of Use.
Cayman Chemical, Item No. 31734, Psilocin-d10 (4-hydroxy DMT-d10, 4-hydroxy-N,N-Dimethyltryptamine-d10), CAS No. 1435934-64-7, obtained from url: <https://www.caymanchem.com/product/31734/4-hydroxy-dmt-d10> on Jan. 26, 2022.
Cerilliant, Certified Reference Material—Certificate of Analysis, Psilocin-D10, Jan. 2018.
Cerilliant, P-099 / P-099-1ML, Psilocin-D10, 100 µg/mL in Acetonitrile, Certified Reference Material, 2022.
Deshmukh et al., "Biopolymer Composites with High Dielectric Performance: Interface Engineering", Biopolymer Composites in Electronics, 2017, 27-128.
Extended European Search Report for European Patent Application No. 21808464.8, dated May 23, 2024.
McIlhenny et al., "Direct analysis of psychoactive tryptamine and harmala alkaloids in the Amazonian botanical medicine ayahuasca by liquid chromatography-electrospray ionization-tandem mass spectrometry", Journal of Chromatography A, Dec. 18, 2009, 1216(51): 8960-8968, ePublished Nov. 5, 2009.
Sigma-Aldrich, New Hydranal® Certified Reference Materials for Water Analysis, Analytix, Issue 3, 2015.

DEUTERATED TRYPTAMINE DERIVATIVES AND METHODS OF USE

PRIORITY

This application is a continuation of U.S. Ser. No. 17/974,007, filed on Oct. 26, 2022, which is a continuation of International Application No. PCT/IB2021/054340 filed May 19, 2021, which claims priority and benefit of U.S. Provisional Application No. 63/026,939 filed May 19, 2020, U.S. Provisional Application No. 63/114,738, filed Nov. 17, 2020 and U.S. Provisional Application No. 63/157,118, filed Mar. 5, 2021. All of the foregoing are incorporated by reference in their entireties.

FIELD

The present disclosure relates generally to chemical compounds and, in some embodiments, to serotonin 5-$HT_2$ receptor agonists and uses in the treatment of diseases associated with a 5-$HT_2$ receptor.

BACKGROUND

There are three, closely related subtypes of serotonin 5-$HT_2$ receptors (5-$HT_2$Rs), 5-$HT_{2A}$. 5-$HT_{2B}$, and 5-$HT_{2C}$, and they are primary targets of classic serotonergic psychedelics, such as lysergic acid diethylamide (LSD), psilocybin, and 2,5-Dimethoxy-4-bromoamphetamine (DOB). They share approximately 60% transmembrane amino acid homology, which poses a challenge to design molecules with selectivity for one subtype over the others. Each subtype is expressed in a unique pattern in mammals (both in peripheral tissues and in the central nervous system), and when stimulated, produces unique biochemical, physiological, and behavioral effects. Activation of 5-$HT_{2A}$Rs, for example, predominantly mediates psychedelic effects and elicits anti-inflammatory effects, whereas activation of 5-$HT_{2C}$Rs reduces feeding behavior. Chronic activation of 5-$HT_{2B}$Rs, however, has been linked to valvular heart disease (VHD), a life-threatening adverse event (AE). Furthermore, there are concerns that patients who could benefit from a 5-$HT_{2A}$R pharmacotherapy could be resistant to experiencing psychedelic effects Tryptamines are a class of serotonergic psychedelics, and possess very high potencies at serotonin 5-$HT_2$Rs (in some cases sub-nanomolar affinities). Certain tryptamines are distinguished from classic psychedelics and other serotonergic psychedelics by possessing selectivity—in some cases 100-fold—for 5-$HT_{2A}$Rs over 5-$HT_{2B}$Rs and 5-$HT_{2C}$Rs.

AEs caused by tryptamines and other serotonergic psychedelics are associated with ingestion of relatively high doses. Likely owing to their very high potency at 5-$HT_{2A}$Rs and 5-$HT_{2C}$Rs, the active oral doses of tryptamines are extremely low. For example, 2C—C-NBOMe (2-(4-Chloro-2,5-dimethoxyphenyl)-N-[(2-methoxyphenyl)methyl]ethan-1-amine) is orally active at doses as low 25 μg, and very strong psychedelic doses are in the range of 500-700 μg. Thus, misuse or abuse, at or exceeding these doses, can cause visual and auditory hallucinations, agitation, aggressiveness, psychosis, and poisoning has been associated with toxicity (e.g., rhabdomyolysis) and fatalities. Furthermore, tryptamines can undergo extensive first-pass metabolism, rendering them orally inactive.

There is a need for serotonin 5-$HT_{2A}$R agonists that overcome the 5-$HT_{2B}$R problem and the issue of psychedelic effects, as well as a need to improve their bioavailability and enhance their oral activity. There is a further need for efficient, more convenient, and controllable tryptamine formulations that afford no neurologically toxic (e.g., psychotomimetic toxic) plasma concentration.

SUMMARY

The present disclosure is based at least in part on the identification of compounds that modulate serotonin 5-$HT_2$ receptors and methods of using the same to treat diseases associated with a serotonin 5-$HT_2$ receptor. More specifically, the present disclosure provides novel compounds that permit, for example, once-daily dosing to selectively engage 5-$HT_{2A}$Rs without producing psychedelic effects, and to treat neuropsychiatric and other disorders associated with inflammation.

Without being bound to any particular theory, it is believed that the novel compounds described herein having selective deuteration, like in the exocyclic moiety, allow for significant slowing of enzymatic degradation with improved exposure (i.e., prevention of high drug concentrations (spiking) observed acutely after administration) and increased blood-to-brain ratio, resulting in enhanced oral bioavailability. Some compounds described herein confer similar benefits by selective deuteration of the phenyl ring.

Disclosed herein is a compound according to Formula (III) or an optically pure stereoisomer, pharmaceutically acceptable salt, solvate, or prodrug thereof.

Formula (III)

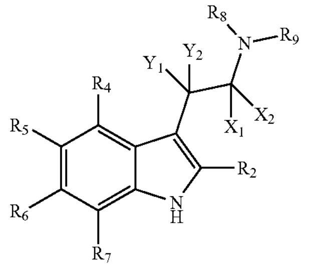

For some embodiments, $X_1$ and $X_2$ are deuterium.

For some embodiments, $Y_1$ and $Y_2$ are hydrogen or deuterium.

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen. $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ is hydrogen.

For some embodiments, when $R_4$ is hydroxyl, $R_9$ is deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, the compound of formula (III) is a compound according to Formula (III-a), Formula (III-b), Formula (III-c), Formula (III-d), Formula (III-c), Formula (III-f), Formula (III-g), Formula (III-h), Formula (III-i), Formula (III-j), Formula (III-k), Formula (III-l), Formula (III-m), Formula (III-n), Formula (III-o), Formula (III-p), Formula (III-q), Formula (III-r), Formula (III-s), Formula (III-t), Formula (III-u), or Formula (III-v), described below.

Disclosed herein is a compound according to Formula (III-a) or an optically pure stereoisomer, pharmaceutically acceptable salt, solvate, or prodrug thereof.

Formula (III-a)

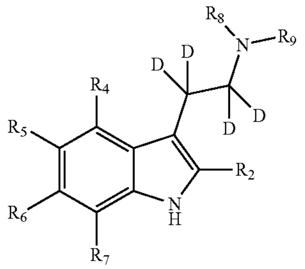

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen, $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ hydrogen or deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-b) or an optically pure stereoisomer, pharmaceutically acceptable salt, solvate, or prodrug thereof.

Formula (III-b)

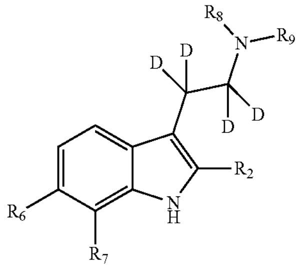

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_8$ and $R_9$ are not both unsubstituted methyl when $R_2$, $R_6$, and $R_7$ are all hydrogen.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-c) or an optically pure stereoisomer, pharmaceutically acceptable salt, solvate, or prodrug thereof.

Formula (III-c)

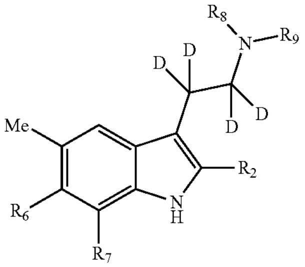

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-d) or an optically pure stereoisomer, pharmaceutically acceptable salt, solvate, or prodrug thereof.

Formula (III-d)

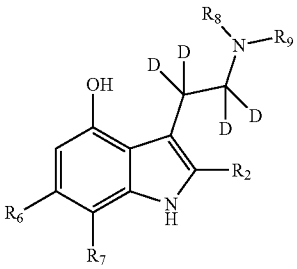

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_2$, $R_6$, and $R_7$ are all hydrogen, $R_8$ and $R_9$ are not both —$CD_3$.

For some embodiments, $R_9$ is hydrogen.

For some embodiments, $R_9$ is hydrogen or deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-e) or an optically pure stereoisomer, pharmaceutically acceptable salt, solvate, or prodrug thereof.

Formula (III-e)

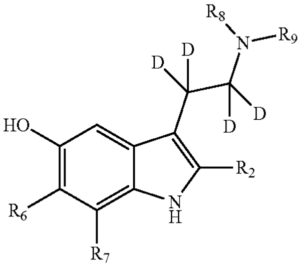

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-f) or an optically pure stereoisomer, pharmaceutically acceptable salt, solvate, or prodrug thereof.

Formlua (III-f)

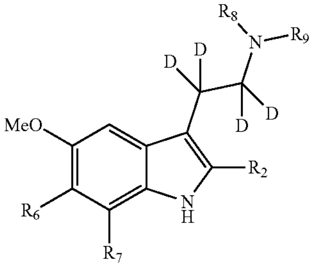

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-g) or an optically pure stereoisomer, pharmaceutically acceptable salt, solvate, or prodrug thereof.

Formula (III-g)

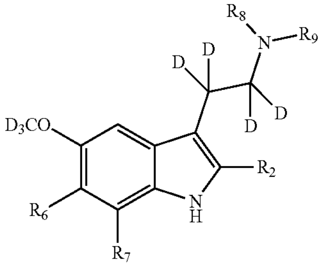

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-h) or an optically pure stereoisomer, pharmaceutically acceptable salt, solvate, or prodrug thereof.

Formula (III-h)

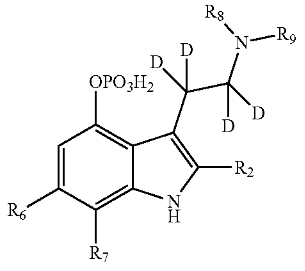

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-i) or an optically pure stereoisomer, pharmaceutically acceptable salt, solvate, or prodrug thereof.

Formula (III-i)

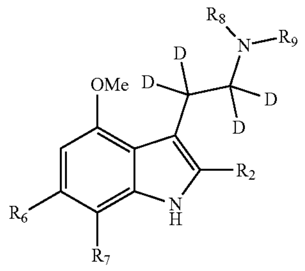

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-j) or an optically pure stereoisomer, pharmaceutically acceptable salt, solvate, or prodrug thereof.

Formula (III-j)

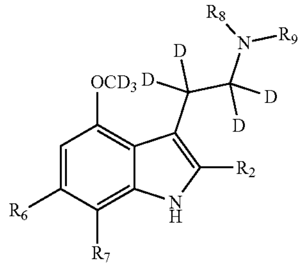

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-k) or an optically pure stereoisomer, pharmaceutically acceptable salt, solvate, or prodrug thereof.

Formula (III-k)

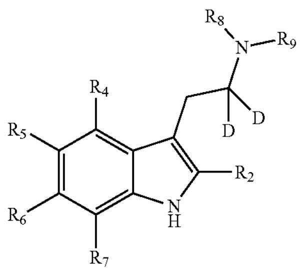

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen, $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ is hydrogen or deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-l) or an optically pure stereoisomer, pharmaceutically acceptable salt, solvate, or prodrug thereof.

Formula (III-l)

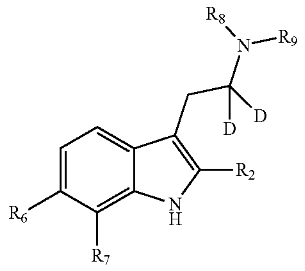

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_8$ and $R_9$ are not both unsubstituted methyl when $R_2$, $R_6$, and $R_7$ are all hydrogen.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-m) or an optically pure stereoisomer, pharmaceutically acceptable salt, solvate, or prodrug thereof.

Formula (III-m)

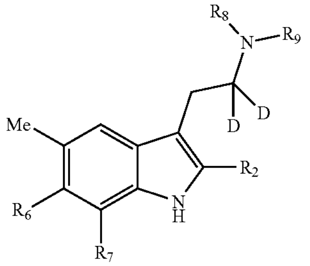

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-n) or an optically pure stereoisomer, pharmaceutically acceptable salt, solvate, or prodrug thereof.

Formula (III-n)

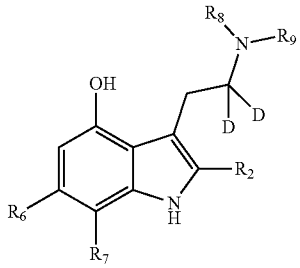

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_2$, $R_6$, and $R_7$ are all hydrogen, $R_8$ and $R_9$ are not both —$CD_3$.

For some embodiments, $R_9$ is hydrogen.

For some embodiments, $R_9$ is deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-o) or an optically pure stereoisomer, pharmaceutically acceptable salt, solvate, or prodrug thereof.

Formula (III-o)

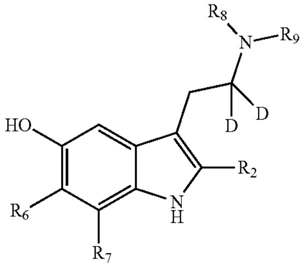

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-p) or an optically pure stereoisomer, pharmaceutically acceptable salt, solvate, or prodrug thereof.

Formula (III-p)

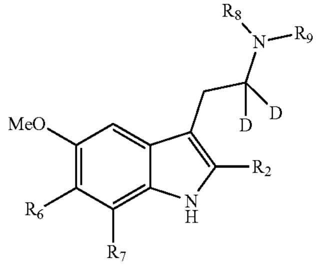

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-q) or an optically pure stereoisomer, pharmaceutically acceptable salt, solvate, or prodrug thereof.

Formula (III-q)

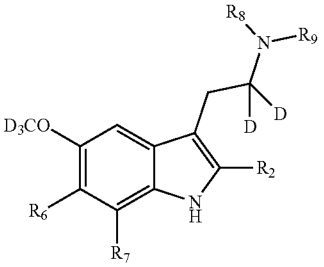

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-r) or an optically pure stereoisomer, pharmaceutically acceptable salt, solvate, or prodrug thereof.

Formula (III-r)

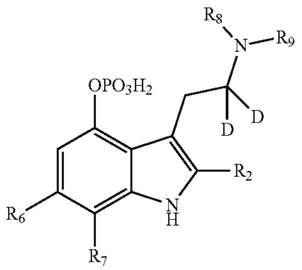

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen, For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-s) or an optically pure stereoisomer, pharmaceutically acceptable salt, solvate, or prodrug thereof.

Formula (III-s)

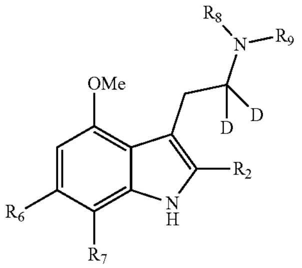

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-t) or an optically pure stereoisomer, pharmaceutically acceptable salt, solvate, or prodrug thereof.

Formula (III-t)

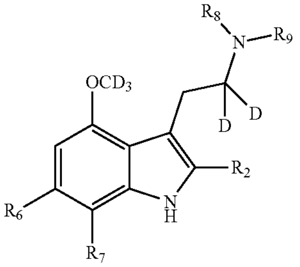

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-u) or an optically pure stereoisomer, pharmaceutically acceptable salt, solvate, or prodrug thereof.

Formula (III-u)

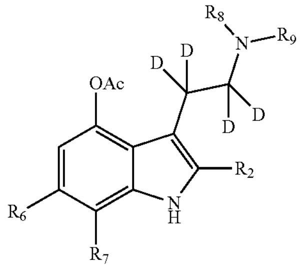

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

Disclosed herein is a compound according to Formula (III-v) or an optically pure stereoisomer, pharmaceutically acceptable salt, solvate, or prodrug thereof.

Formula (III-v)

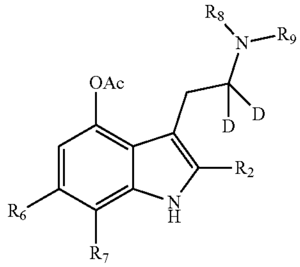

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, the compound is:

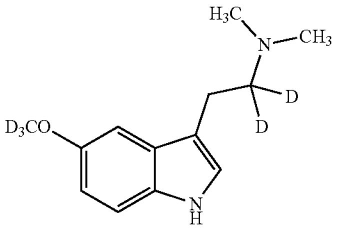

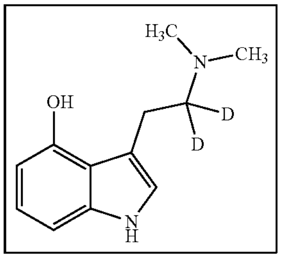

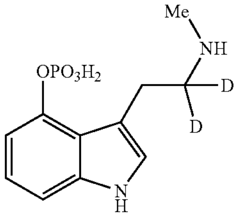

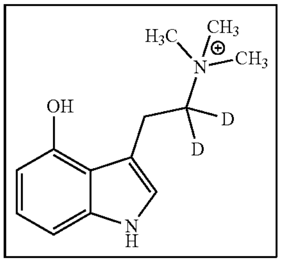

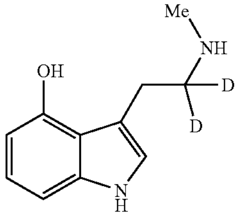

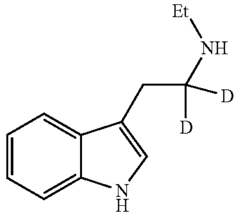

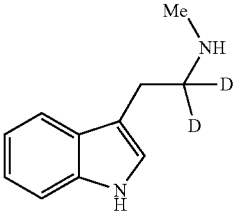

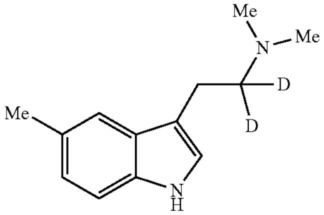

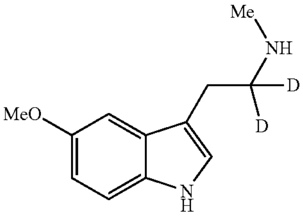

-continued

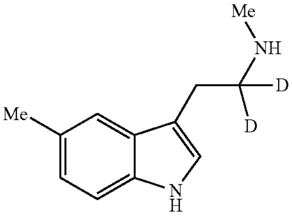

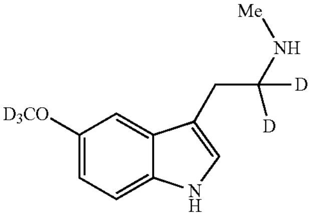

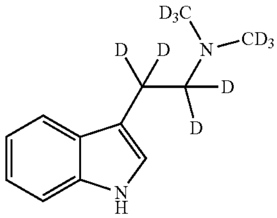

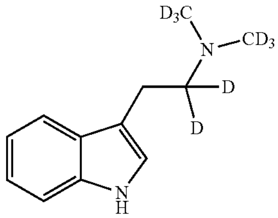

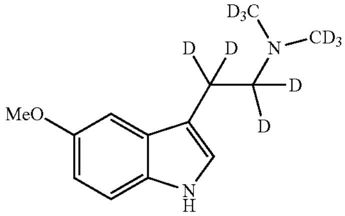

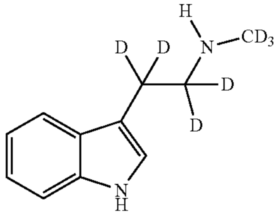

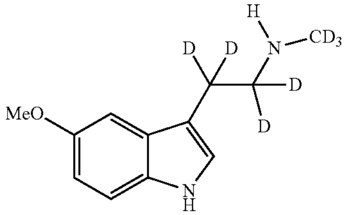

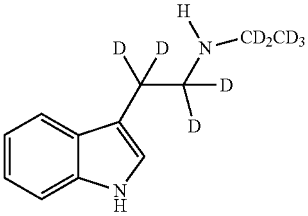

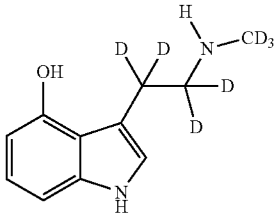

-continued

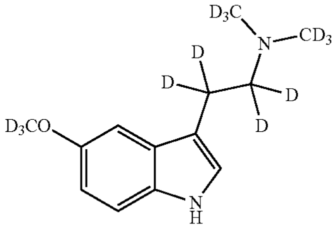

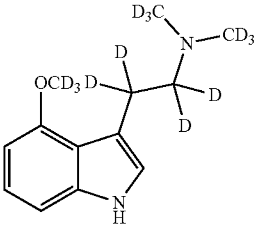

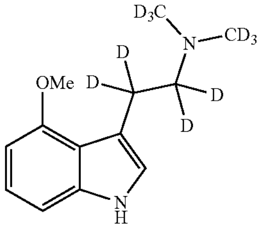

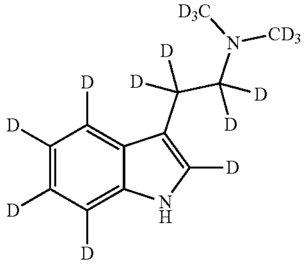

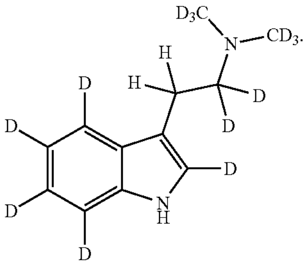

For some embodiments, the compound has the following structure:

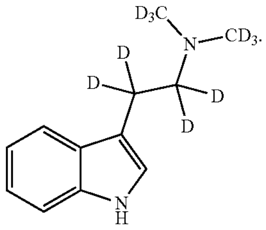 [SMILES: [2H]C([2H])([2H])N(C([2H])([2H])[2H])C([2H])([2H])C([2H])([2H])c1c[nH]c2ccccc12]

For some embodiments, the compound is an agonist of a serotonin 5-$HT_2$ receptor.

For some embodiments, the compound can be agonists of a serotonin 5-$HT_{2A}$ receptor.

Also disclosed herein is a pharmaceutical composition comprising a compound as disclosed herein and a pharmaceutically acceptable vehicle.

Also disclosed herein is a method of treating a subject with a disease or disorder comprising administering to the subject a therapeutically effective amount of a compound as disclosed herein.

Also disclosed herein is a method of treating a subject with a disease or disorder comprising administering to the subject a therapeutically effective amount of a compound as disclosed herein.

Also disclosed herein is a method of treating a subject with a disease or disorder associated with a serotonin 5-$HT_2$ receptor comprising administering to the subject a therapeutically effective amount of a compound as disclosed herein. In some embodiments, the compound has the following structure:

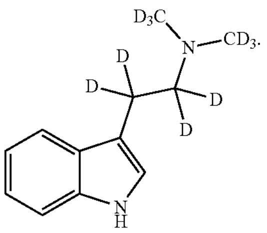 [SMILES: [2H]C([2H])([2H])N(C([2H])([2H])[2H])C([2H])([2H])C([2H])([2H])c1c[nH]c2ccccc12]

In some embodiments, the disease or disorder may include central nervous system (CNS) disorders, for example, post-traumatic stress disorder (PTSD), major depressive disorder (MDD), treatment-resistant depression (TRD), suicidal ideation, suicidal behavior, major depressive disorder with suicidal ideation or suicidal behavior, nonsuicidal self-injury disorder (NSSID), bipolar and related disorders (including but not limited to bipolar I disorder, bipolar II disorder, cyclothymic disorder), obsessive-compulsive disorder (OCD), generalized anxiety disorder (GAD), social anxiety disorder, substance use disorders (including but not limited to alcohol use disorder, opioid use disorder, amphetamine use disorder, nicotine use disorder, and cocaine use disorder), anorexia nervosa, bulimia nervosa, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, and obesity. In some embodiments, the disease or disorder is alcohol use disorder. In some embodiments, the disease or disorder may include conditions of the autonomic nervous system (ANS). In some embodiments, the disease or disorder may include pulmonary disorders (e.g., asthma and chronic obstructive pulmonary disorder (COPD). In some embodiments, the disease or disorder may include cardiovascular disorders (e.g., atherosclerosis).

Also disclosed is a method of treating a subject with alcohol use disorder associated with a serotonin 5-$HT_2$ receptor comprising administering to the subject a therapeutically effective amount of a compound having the following structure:

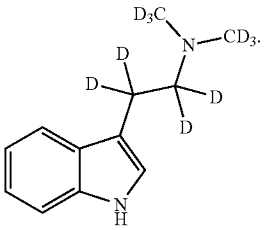 [SMILES: [2H]C([2H])([2H])N(C([2H])([2H])[2H])C([2H])([2H])C([2H])([2H])c1c[nH]c2ccccc12]

Also disclosed herein is a single-layer orally administered tablet composition comprising a tryptamine derivative, such as DMT, 5-MeO-DMT, psilocybin, and psilocin, or any of the compounds described herein, or a pharmaceutically acceptable salt thereof, and a polymer. In some embodiments, the compound has the following structure:

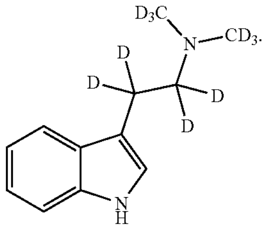 [SMILES: [2H]C([2H])([2H])N(C([2H])([2H])[2H])C([2H])([2H])C([2H])([2H])c1c[nH]c2ccccc12]

In some embodiments, the composition is adapted for maximum sustained release.

In some embodiments, the tablet composition comprises a combination of (i) a water-insoluble neutrally charged non-ionic matrix; (ii) a polymer carrying one or more negatively charged groups; and (iii) a tryptamine derivative, such as DMT, 5-MeO-DMT, psilocybin, and psilocin, or any of the compounds described herein, or a pharmaceutically acceptable salt thereof.

In some embodiments, the non-ionic matrix is selected from cellulose-based polymers, alone or enhanced by mixing with components such as starches; waxes; neutral gums; polymethacrylates; PVA; PVA/PVP blends; or mixtures thereof.

In some embodiments, the cellulose-based polymer is hydroxypropyl methylcellulose (HPMC).

In some embodiments, the polymer carrying one or more negatively charged groups is polyacrylic acid, polylactic acid, polyglycolic acid, polymethacrylate carboxylates, cation-exchange resins, clays, zeolites, hyaluronic acid, anionic gums, salts thereof, or mixtures thereof.

In some embodiments, the anionic gum is a naturally occurring material, a semi-synthetic material, or combinations thereof.

In some embodiments, the naturally occurring material is alginic acid, pectin, xanthan gum, carrageenan, locust bean gum, gum arabic, gum karaya, guar gum, gum tragacanth, or combinations thereof.

In some embodiments, the semi-synthetic material is carboxymethyl-chitin, cellulose gum, or combinations thereof.

In some embodiments, the tablet composition comprises a therapeutically effective amount of a tryptamine derivative, such as DMT, 5-MeO-DMT, psilocybin, and psilocin, or any of the compounds described herein, or a pharmaceutically acceptable salt thereof, for the treatment of pain.

In some embodiments, the tablet composition comprises a therapeutically effective amount of a tryptamine derivative, such as DMT, 5-MeO-DMT, psilocybin, and psilocin, or any of the compounds described herein, or a pharmaceutically acceptable salt thereof, for the treatment of brain injury.

In some embodiments, the tablet composition comprises a therapeutically effective amount of a tryptamine derivative, such as DMT, 5-MeO-DMT, psilocybin, and psilocin, or any of the compounds described herein, or a pharmaceutically acceptable salt thereof, for the treatment of depression.

In some embodiments, the tablet composition comprises a therapeutically effective amount of a tryptamine derivative, such as DMT, 5-MeO-DMT, psilocybin, and psilocin, or any of the compounds described herein, or a pharmaceutically acceptable salt thereof, for use in treating a disease or disorder associated with a serotonin 5-$HT_2$ receptor.

For some embodiments, the disease or disorder is selected from the group consisting of central nervous system (CNS) disorders, including major depressive disorder (MDD), major depressive disorder (MDD) with suicidal ideation or suicidal behavior, suicidal ideation, suicidal behavior, non-suicidal self-injury disorder (NSSID), treatment-resistant depression (TRD), post-traumatic stress disorder (PTSD), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme Disease, and obesity, or combinations thereof. In some embodiments, the disease or disorder is alcohol use disorder.

For some embodiments, the disease or disorder includes conditions of the autonomic nervous system (ANS).

For some embodiments, the disease or disorder includes pulmonary disorders including asthma and chronic obstructive pulmonary disorder (COPD).

For some embodiments, the disease or disorder includes cardiovascular disorders including atherosclerosis.

In some embodiments, the composition achieves a combined concentration of a tryptamine derivative, such as DMT, 5-MeO-DMT, psilocybin, and psilocin, or any of the compounds described herein, or a pharmaceutically acceptable salt thereof, in plasma in the range of 10-500 (e.g., about 10, 20, 30, 40, 50, 100, 150, 200, 250, 300, 350, 400, 450, 500 or more ng/ml (or any range between about 10 and about 500 ng/ml, e.g., about 100 to about 300 ng/ml, about 250 to about 450 ng/ml, or about 50 to about 400 ng/ml), and maintains this concentration for duration of the release period.

In some embodiments, the polymer comprises one or more negatively charged groups.

Also disclosed herein is a tablet composition formulated for oral administration comprising: a tryptamine derivative, such as DMT, 5-MeO-DMT, psilocybin, and psilocin, or any of the compounds described herein, or a pharmaceutically acceptable salt thereof, and a polymer. In some embodiments, the compound has the following structure:

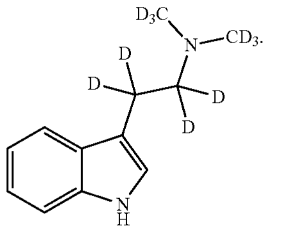 [SMILES: [2H]C([2H])([2H])N(C([2H])([2H])[2H])C([2H])([2H])C([2H])([2H])c1c[nH]c2ccccc12]

In some embodiments, the polymer comprises one or more negatively charged groups.

In some embodiments, the polymer comprises one or more acid groups.

In some embodiments, the polymer comprises a water-insoluble neutrally charged non-ionic matrix.

In some embodiments, the non-ionic matrix is selected from cellulose-based polymers, alone or enhanced by mixing with components such as starches; waxes; neutral gums; polymethacrylates; PVA; PVA/PVP blends; or mixtures thereof.

In some embodiments, the cellulose-based polymer is hydroxypropyl methylcellulose (HPMC).

Also described herein is a kit for the treatment of a subject comprising 1) a single-layer orally administered tablet composition as disclosed herein, and 2) instructions for use in the treatment of pain.

Also described herein is a kit for the treatment of a subject comprising 1) a single-layer orally administered tablet composition as disclosed herein, and 2) instructions for use in the treatment of brain injury.

Also described herein is a kit for the treatment of a subject comprising 1) a single-layer orally administered tablet composition as disclosed herein, and 2) instructions for use in the treatment of depression.

Also described herein is a kit for the treatment of a subject comprising 1) a single-layer orally administered tablet composition as disclosed herein, and 2) instructions for use in the treatment of a disease or disorder associated with a serotonin 5-$HT_2$ receptor.

DETAILED DESCRIPTION

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

Unless defined otherwise, all technical and scientific terms used herein have the same meaning as is commonly understood by one of skill in the art to which this disclosure belongs.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —$S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 6, including, for example, 1 to 3 carbon atoms that are either straight-chained or branched, and which are optionally interrupted with one or more groups selected from —O—, —$NR^{10}$—, —$NR^{10}C(O)$—, —$C(O)NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene am as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms, for example 2 to 4 carbon atoms and having at least 1, for example from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms, for example, 2 to 3 carbon atoms and having at least 1 and for example, from 1 to 2 sites of triple bond unsaturation. Examples of such alkynyl groups include acetylenyl (—C≡CH), and propargyl (—$CH_3C$≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$ "Acylamino" refers to the groups —$NR^{20}C(O)$alkyl, —$NR^{20}C(O)$substituted alkyl, $NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}$C(O)$NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_1$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O— cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and for example, from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO-alkyl, —$SO_2$-substituted alkyl, —$SO_2$-aryl and —$SO_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO— substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms a selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO- moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —SO-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —$NO_2$.

"Oxo" refers to the atom (═O).

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, OSO-substituted alkenyl, $OSO_2$-cycloalkyl, $OSO_2$-substituted cycloalkyl, $OSO_2$-cycloalkenyl. $OSO_2$-substituted cycloalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═$NR^{70}$, ═N—$OR^{70}$, ═$N_2$ or ═S) on saturated carbon atoms in the specified group or radical are, unless otherwise specified, —$R^{60}$, halo, ═O, —$OR^{71}$, —$SR^{70}$, —$NR^{80}R^{80}$, trihalomethyl, —CN, —OCN, —SCN, —NO, —$NO_2$, ═$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the disclosure and the other a typical counter ion such as chloride, or two ionized compounds disclosed herein can serve as counter ions for such divalent alkali earth ions, or a doubly ionized compound of the disclosure can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^7$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, the language "maximum sustained release" describes the release window for certain formulations of the present disclosure formulated to increase the release period to a maximum value, which is ultimately limited by the time the gastrointestinal tract naturally excretes all drugs with food.

The language "tamper resistance" is art-recognized to describe aspects of a drug formulation that make it more difficult to use the formulation to abuse the drug moiety of the formulation through extraction for intravenous use, or crushing for freebase use; and therefore reduce the risk for abuse of the drug.

As used herein, the term "steady" describes the stable or steady-state level of a molecule concentration, e.g., concentration of any compound described herein.

As used herein, the term "composition" is equivalent to the term "formulation."

As used herein, the language "administration event" describes the administration of a subject a given dose, in the form of one or more pills within a short window of time, e.g., less than 10 minutes.

As used herein, the language "release period" describes the time window in which any compound described herein is released from the matrix to afford plasma concentrations of compounds described herein. The start time of the release period is defined from the point of oral administration to a subject, which is considered nearly equivalent to entry into the stomach, and initial dissolution by gastric enzymes and acid. The end time of the release period is defined as the point when the entire loaded drug is released. In embodiments, the release period can be greater than about 4 hours, 8 hours, 12 hours, 16 hours, or 20 hours, greater than or equal to about 24 hours, 28 hours, 32 hours, 36 hours, or 48 hours, or less than about 48 hours, 36 hours, 4 hours or less, 3 hours or less, 2 hour or less, or 1 hour or less.

The term "treating" or "treatment" as used herein means the treating or treatment of a disease or medical condition in a patient, such as a mammal (particularly a human) that includes: ameliorating the disease or medical condition, such as, eliminating or causing regression of the disease or medical condition in a patient; suppressing the disease or medical condition, for example by, slowing or arresting the development of the disease or medical condition in a patient; or alleviating a symptom of the disease or medical condition in a patient. In an embodiment, prophylactic treatment can result in preventing the disease or medical condition from occurring, in a subject.

"Patient" refers to human and non-human subjects, especially mammalian subjects.

As used herein, and unless otherwise specified, the terms "prevent," "preventing" and "prevention" refer to the prevention of the onset, recurrence or spread of a disease, disorder, or condition, or of one or more symptoms thereof. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term"managing" encompasses treating a subject who had suffered from the particular disease, disorder, or condition in an attempt to prevent or minimize the recurrence of the disease, disorder, or condition.

"Pharmaceutically effective amount" and "therapeutically effective amount" refer to an amount of a compound sufficient to treat a specified disorder or disease or one or more of its symptoms and/or to prevent the occurrence of the disease or disorder.

As used herein, and unless otherwise specified, a "prophylactically effective amount" of an active agent, is an amount sufficient to prevent a disease, disorder, or condition, or prevent its recurrence. The term "prophylactically effective amount" can encompass an amount that improves overall prophylaxis or enhances the prophylactic efficacy of another prophylactic agent.

The language "neurologically toxic spikes" is used herein to describe spikes in concentration of any compound described herein that would produce side-effects of sedation or psychotomimetic effects, e.g., hallucination, dizziness, and nausea; which can not only have immediate repercussions, but also effect treatment compliance. In particular, side effects may become more pronounced at blood concentration levels above about 300 ng/L (e.g. above about 300, 400, 500, 600 or more ng/L).

As used herein, and unless otherwise specified, a "neuropsychiatric disease or disorder" is a behavioral or psychological problem associated with a known neurological condition, and typically defined as a cluster of symptoms that co-exist. Examples of neuropsychiatric disorders include, but are not limited to, schizophrenia, cognitive deficits in schizophrenia, attention deficit disorder, attention deficit hyperactivity disorder, bipolar and manic disorders, depression or any combinations thereof.

"Inflammatory conditions" or"inflammatory disease," as used herein, refers broadly to chronic or acute inflammatory diseases. Inflammatory conditions and inflammatory diseases, include but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis. Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

Compounds

Disclosed herein is a compound according to Formula (I) or an optically pure stereoisomer, pharmaceutically acceptable salt, solvate, or prodrug thereof, wherein $X_1$ and $X_2$ are deuterium and $Y_1$ and $Y_2$ are deuterium.

Formula (I)

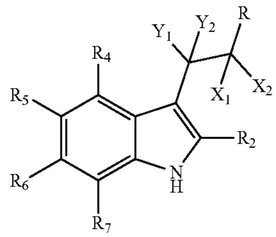

For some embodiments, R is

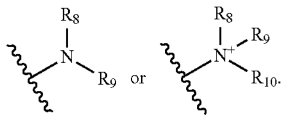

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is a partially or fully deuterated alkyl. For some embodiments, $R_5$ is a partially or fully deuterated methyl or ethyl.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_8$ and $R_9$ are not both —$CD_3$.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is hydrogen or deuterium.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is not an unsubstituted or substituted alkyl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (I-a) or an optically pure stereoisomer, pharmaceutically acceptable salt, solvate, or prodrug thereof, wherein $X_1$ and $X_2$ are deuterium and $Y_1$ and $Y_2$ are deuterium.

Formula (I-a)

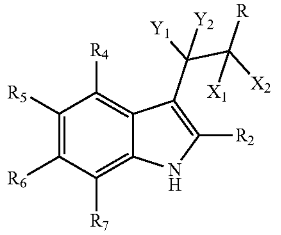

For some embodiments, R is

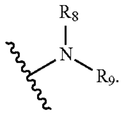

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_8$ and $R_9$ are not both —$CD_3$.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is hydrogen or deuterium.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is not an unsubstituted or substituted alkyl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (I-b) or an optically pure stereoisomer, pharmaceutically acceptable salt, solvate, or prodrug thereof, wherein $X_1$ and $X_2$ are deuterium and $Y_1$ and $Y_2$ are deuterium.

Formula (I-b)

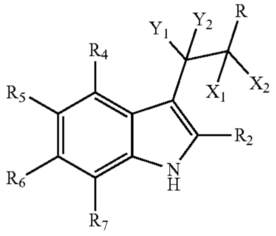

For some embodiments, R is

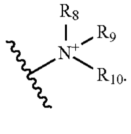

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_5$ is a partially or fully deuterated alkyl. For some embodiments, $R_8$ is a partially or fully deuterated methyl or ethyl.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_8$ and $R_9$ are not both $—CD_3$.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is hydrogen or deuterium.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that when $R_4$ is hydroxyl, $R_9$ is not unsubstituted or substituted alkyl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (I-c) or an optically pure stereoisomer, pharmaceutically acceptable salt, solvate, or prodrug thereof.

Formula (I-c)

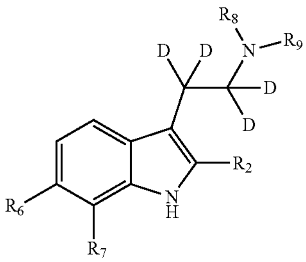

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-d) or an optically pure stereoisomer, pharmaceutically acceptable salt, solvate, or prodrug thereof.

Formula (I-d)

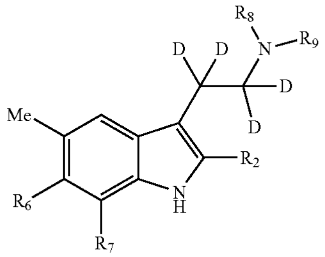

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-e) or an optically pure stereoisomer, pharmaceutically acceptable salt, solvate, or prodrug thereof.

Formula (I-e)

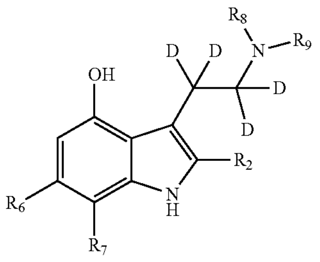

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that $R_8$ and $R_9$ are not both —$CD_3$.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-f) or an optically pure stereoisomer, pharmaceutically acceptable salt, solvate, or prodrug thereof.

Formula (I-f)

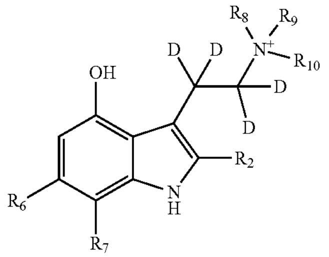

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, under the proviso that $R_8$ and $R_9$ are not both —$CD_3$.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-g) or an optically pure stereoisomer, pharmaceutically acceptable salt, solvate, or prodrug thereof.

Formula (I-g)

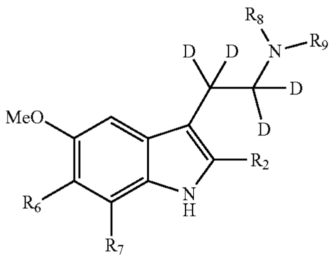

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-h) or an optically pure stereoisomer, pharmaceutically acceptable salt, solvate, or prodrug thereof.

Formula (I-h)

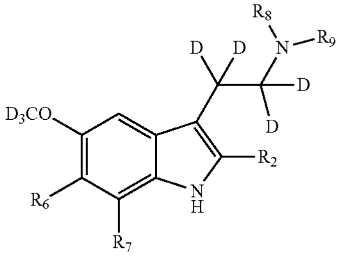

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-i) or an optically pure stereoisomer, pharmaceutically acceptable salt, solvate, or prodrug thereof.

Formula (I-i)

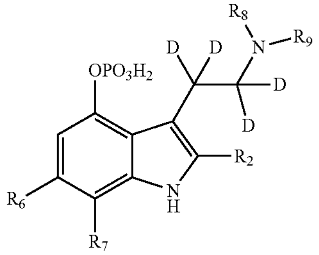

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-j) or an optically pure stereoisomer, pharmaceutically acceptable salt, solvate, or prodrug thereof.

Formula (I-j)

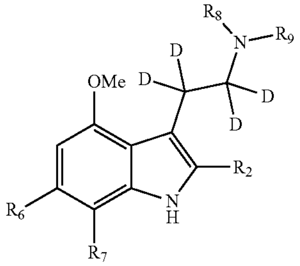

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (I-k) or an optically pure stereoisomer, pharmaceutically acceptable salt, solvate, or prodrug thereof.

Formula (I-k)

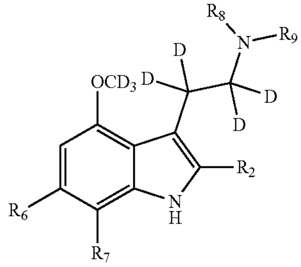

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II) or an optically pure stereoisomer, pharmaceutically acceptable salt, solvate, or prodrug thereof, wherein $X_1$ and $X_2$ are deuterium, and $Y_1$ and $Y_2$ are hydrogen.

Formula (II)

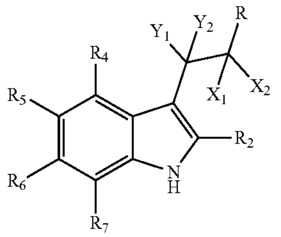

For some embodiments, R is

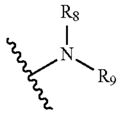

or

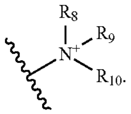

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (II-a) or an optically pure stereoisomer, pharmaceutically acceptable salt, solvate, or prodrug thereof, wherein $X_1$ and $X_2$ deuterium, $Y_1$ and $Y_2$ are hydrogen, and R is

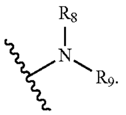

Formula (II-a)

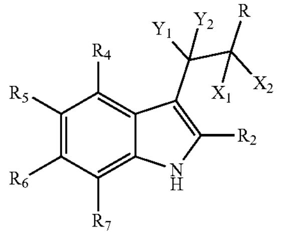

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, RR is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (II-b) or an optically pure stereoisomer, pharmaceutically acceptable salt, solvate, or prodrug thereof, wherein $X_1$ and $X_2$ are deuterium, $Y_1$ and $Y_2$ are hydrogen, and R is

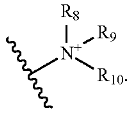

Formula (II-b)

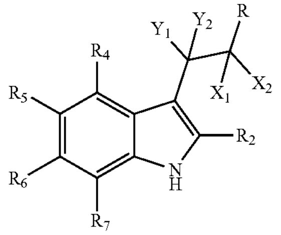

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (II-c) or an optically pure stereoisomer, pharmaceutically acceptable salt, solvate, or prodrug thereof, wherein $X_1$ and $X_2$ are deuterium, $Y_1$ and $Y_2$ are hydrogen, and R is

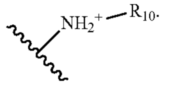

Formula (II-c)

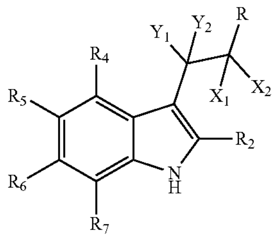

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_{10}$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_{10}$ is a partially or fully deuterated methyl or ethyl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (II-d) or an optically pure stereoisomer, pharmaceutically acceptable salt, solvate, or prodrug thereof.

Formula (II-d)

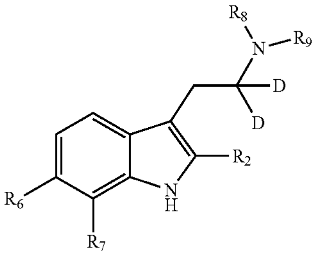

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II-e) or an optically pure stereoisomer, pharmaceutically acceptable salt, solvate, or prodrug thereof.

Formula (II-e)

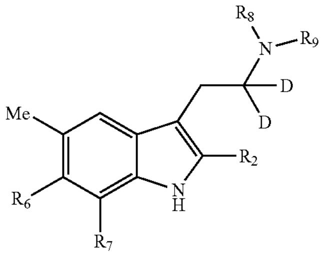

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II-f) or an optically pure stereoisomer, pharmaceutically acceptable salt, solvate, or prodrug thereof.

Formula (II-f)

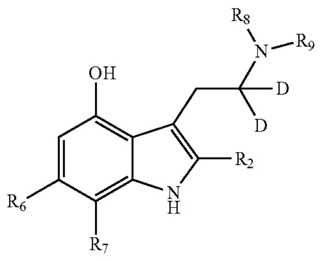

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II-g) or an optically pure stereoisomer, pharmaceutically acceptable salt, solvate, or prodrug thereof.

Formula (II-g)

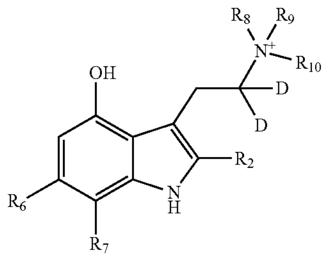

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_9$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, substituted means partially or fully substituted with deuterium, e.g., substituted alkyl is a partially or fully deuterated alkyl.

Disclosed herein is a compound according to Formula (II-h) or an optically pure stereoisomer, pharmaceutically acceptable salt, solvate, or prodrug thereof.

Formula (II-h)

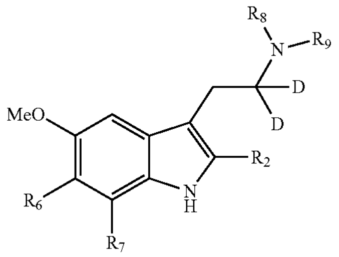

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II-i) or an optically pure stereoisomer, pharmaceutically acceptable salt, solvate, or prodrug thereof.

Formula (II-i)

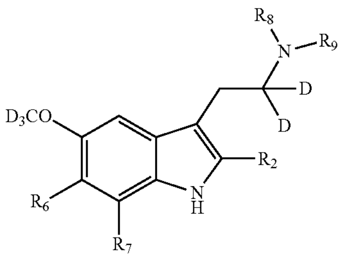

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (II-j) or an optically pure stereoisomer, pharmaceutically acceptable salt, solvate, or prodrug thereof.

Formula (II-j)

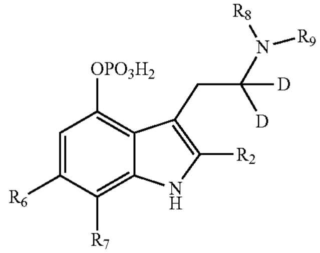

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_6$ and $R_7$ are selected from hydrogen, deuterium, and halogen.

For some embodiments, $R_8$ is a partially or fully deuterated alkyl. For some embodiments, $R_8$ is a partially or fully deuterated methyl or ethyl.

For some embodiments, $R_9$ is selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, unsubstituted or substituted alkyl is an unsubstituted or partially or fully deuterated methyl or ethyl.

For some embodiments, substituted means partially or fully substituted with deuterium, e.g., substituted alkyl is a partially or fully deuterated alkyl.

Disclosed herein is a compound according to Formula (III) or an optically pure stereoisomer, pharmaceutically acceptable salt, solvate, or prodrug thereof.

Formula (III)

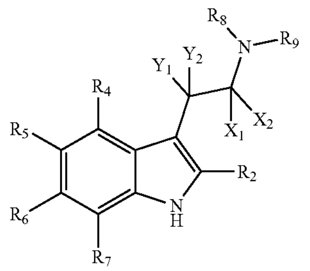

For some embodiments, $X_1$ and $X_2$ are deuterium.

For some embodiments, $Y_1$ and $Y_2$ are hydrogen or deuterium.

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl. For some embodiments, $R_2$ is independently selected from hydrogen, deuterium, halogen, and an unsubstituted or partially or fully deuterated methyl or ethyl.

For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl. For some embodiments, $R_8$ is a partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen, $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ is hydrogen.

For some embodiments, when $R_4$ is hydroxyl, $R_9$ is deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl. For some embodiments, alkoxy is methoxy or ethoxy.

For some embodiments, the compound of formula (III) is a compound according to Formula (III-a), Formula (III-b), Formula (III-c), Formula (III-d), Formula (III-e), Formula (III-f), Formula (III-g), Formula (III-h), Formula (III-i), Formula (III-j), Formula (III-k), Formula (III-l), Formula (III-m), Formula (III-n), Formula (III-o), Formula (III-p), Formula (III-q), Formula (III-r), Formula (III-s), Formula (III-t), Formula (III-u), or Formula (III-v), described below.

Disclosed herein is a compound according to Formula (III-a) or an optically pure stereoisomer, pharmaceutically acceptable salt, solvate, or prodrug thereof.

Formula (III-a)

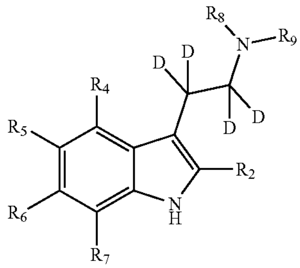

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ is independently selected from hydrogen, deuterium, hydroxyl, unsubstituted or substituted alkoxy, unsubstituted or substituted acetoxy, and phosphoryloxy.

For some embodiments $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen, $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ is hydrogen or deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (III-b) or an optically pure stereoisomer, pharmaceutically acceptable salt, solvate, or prodrug thereof.

Formula (III-b)

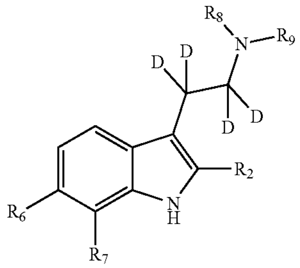

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_8$ and $R_9$ are not both unsubstituted methyl when $R_2$, $R_6$, and $R_7$ are all hydrogen.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-c) or an optically pure stereoisomer, pharmaceutically acceptable salt, solvate, or prodrug thereof.

Formula (III-c)

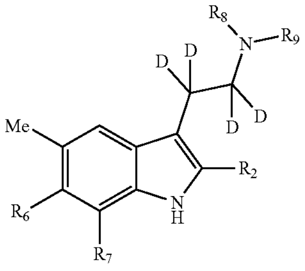

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_6$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-d) or an optically pure stereoisomer, pharmaceutically acceptable salt, solvate, or prodrug thereof.

Formula (III-d)

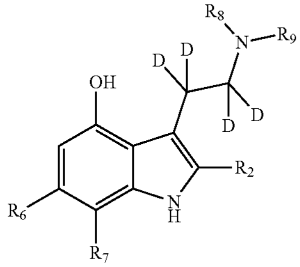

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_2$, $R_6$, and $R_7$ are all hydrogen, $R_8$ and $R_9$ are not both —$CD_3$.

For some embodiments, $R_9$ is hydrogen.

For some embodiments, $R_9$ is deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-e) or an optically pure stereoisomer, pharmaceutically acceptable salt, solvate, or prodrug thereof.

Formula (III-e)

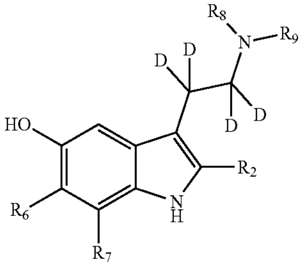

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ am selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-f) or an optically pure stereoisomer, pharmaceutically acceptable salt, solvate, or prodrug thereof.

Formula (III-f)

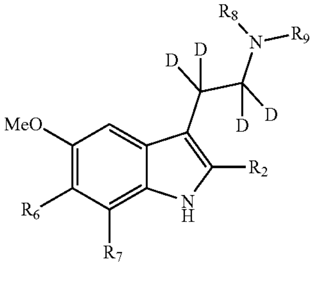

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_5$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-g) or an optically pure stereoisomer, pharmaceutically acceptable salt, solvate, or prodrug thereof.

Formula (III-g)

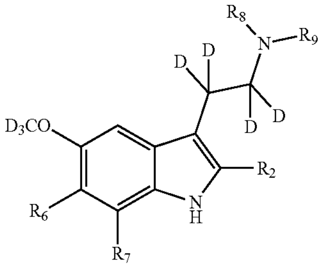

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-h) or an optically pure stereoisomer, pharmaceutically acceptable salt, solvate, or prodrug thereof.

Formula (III-h)

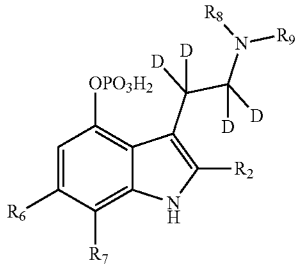

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-i) or an optically pure stereoisomer, pharmaceutically acceptable salt, solvate, or prodrug thereof.

Formula (III-i)

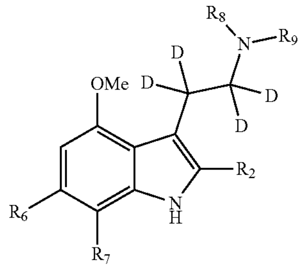

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-j) or an optically pure stereoisomer, pharmaceutically acceptable salt, solvate, or prodrug thereof.

Formula (III-j)

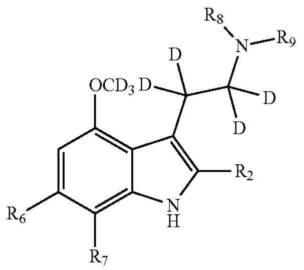

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-k) or an optically pure stereoisomer, pharmaceutically acceptable salt, solvate, or prodrug thereof.

Formula (III-k)

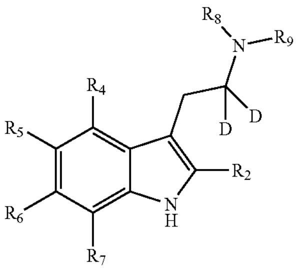

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, For some embodiments, $R_4$ is independently selected from hydrogen, deuterium, hydroxyl, unsubstituted or substituted alkoxy, unsubstituted or substituted acetoxy, and phosphoryloxy.

For some embodiments, $R_5$ is independently selected from hydrogen, deuterium, hydroxyl, unsubstituted or substituted alkoxy, and phosphoryloxy.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_4$ is hydroxyl and $R_2$, $R_5$, $R_6$, and $R_7$ are all hydrogen, $R_8$ and $R_9$ are not both —$CD_3$, and $R_8$ and $R_9$ are not both unsubstituted methyl when $R_2$, $R_4$, $R_5$, $R_6$, and $R_7$ are all hydrogen.

For some embodiments, when $R_4$ is hydroxyl, $R_9$ is hydrogen or deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl. For some embodiments, alkoxy is methoxy or ethoxy.

Disclosed herein is a compound according to Formula (III-l) or an optically pure stereoisomer, pharmaceutically acceptable salt, solvate, or prodrug thereof.

Formula (III-l)

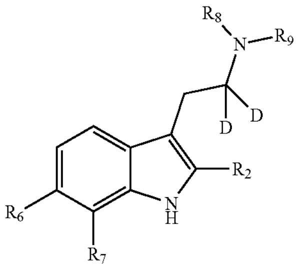

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_8$ and $R_9$ are not both unsubstituted methyl when $R_2$, $R_6$, and $R_7$ are all hydrogen.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-m) or an optically pure stereoisomer, pharmaceutically acceptable salt, solvate, or prodrug thereof.

Formula (III-m)

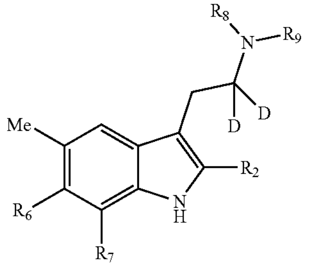

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-n) or an optically pure stereoisomer, pharmaceutically acceptable salt, solvate, or prodrug thereof.

Formula (III-n)

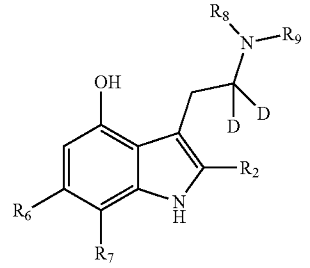

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, when $R_2$, $R_6$, and $R_7$ are all hydrogen, $R_8$ and $R_9$ are not both —$CD_3$.

For some embodiments, $R_9$ is hydrogen.

For some embodiments, $R_9$ is deuterium.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-o) or an optically pure stereoisomer, pharmaceutically acceptable salt, solvate, or prodrug thereof.

Formula (III-o)

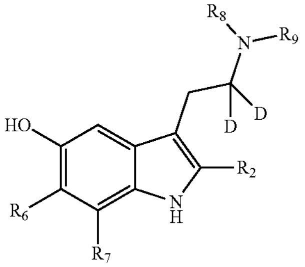

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-p) or an optically pure stereoisomer, pharmaceutically acceptable salt, solvate, or prodrug thereof.

Formula (III-p)

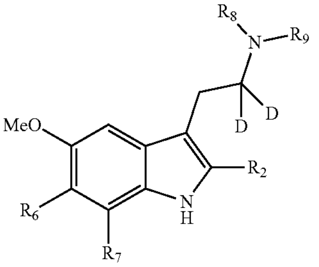

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-q) or an optically pure stereoisomer, pharmaceutically acceptable salt, solvate, or prodrug thereof.

Formula (III-q)

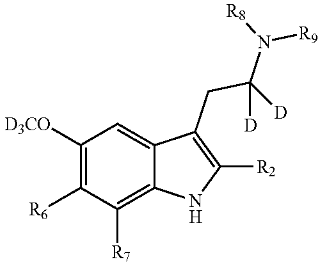

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-r) or an optically pure stereoisomer, pharmaceutically acceptable salt, solvate, or prodrug thereof.

Formula (III-r)

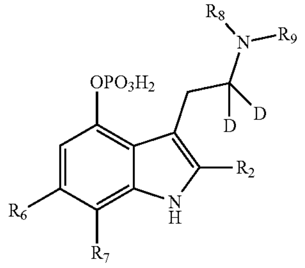

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen, For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-s) or an optically pure stereoisomer, pharmaceutically acceptable salt, solvate, or prodrug thereof.

Formula (III-s)

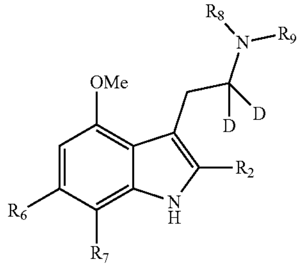

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-t) or an optically pure stereoisomer, pharmaceutically acceptable salt, solvate, or prodrug thereof.

Formula (III-t)

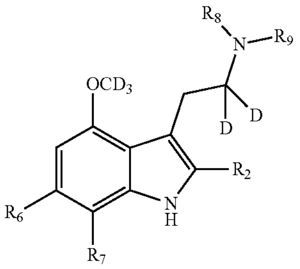

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-u) or an optically pure stereoisomer, pharmaceutically acceptable salt, solvate, or prodrug thereof.

Formula (III-u)

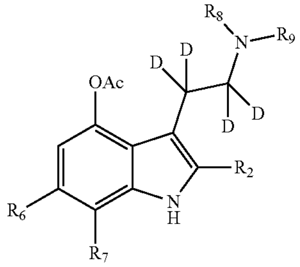

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.

For some embodiments, substituted means partially or fully substituted with deuterium, e.g., substituted alkyl is a partially or fully deuterated alkyl.

Disclosed herein is a compound according to Formula (III-v) or an optically pure stereoisomer, pharmaceutically acceptable salt, solvate, or prodrug thereof.

Formula (III-v)

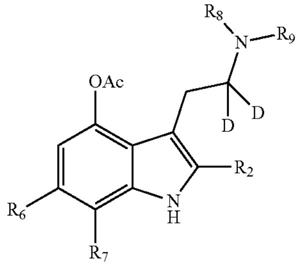

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_6$ and $R_7$ are selected from hydrogen, deuterium, and halogen.

For some embodiments, $R_8$ is an unsubstituted or partially or fully deuterated methyl or ethyl.

For some embodiments, $R_9$ is hydrogen, deuterium, or an unsubstituted or partially or fully deuterated methyl or ethyl.

For some embodiments, $R_2$ is independently selected from hydrogen, deuterium, halogen, and an unsubstituted or partially or fully deuterated methyl or ethyl.

For some embodiments, $R_8$ and $R_9$ are not both unsubstituted or partially or fully deuterated ethyl.
For some embodiments, substituted means partially or fully substituted with deuterium, e.g., substituted alkyl is a partially or fully deuterated alkyl.
For some embodiments, the compound is selected from:
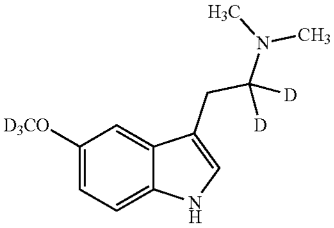
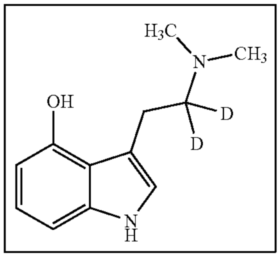
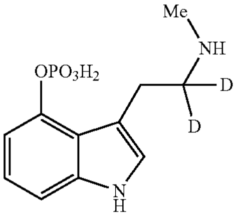
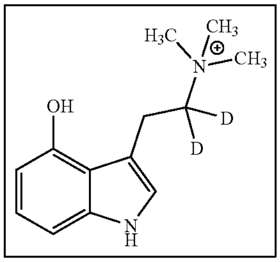
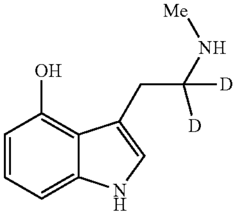
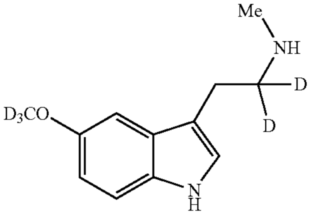
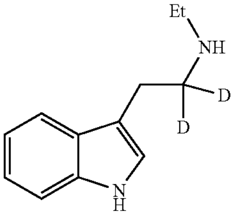
-continued
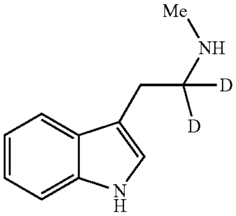
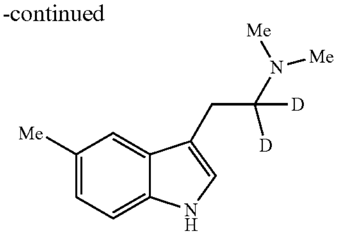
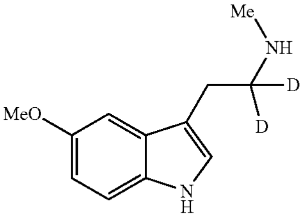 [SMILES: [2H]C([2H])(Cc1c[nH]c2ccc(OC)cc12)NC]
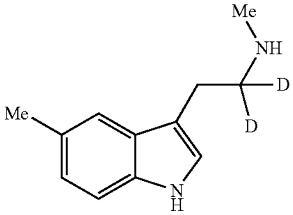
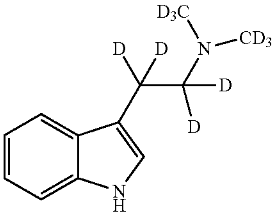
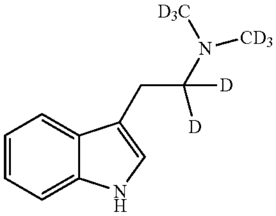
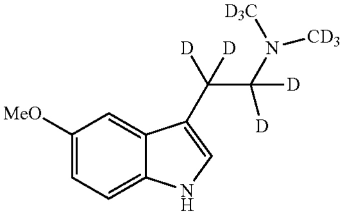
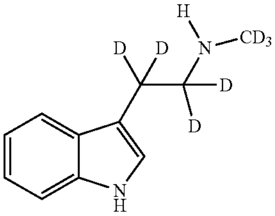
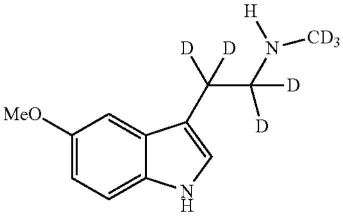
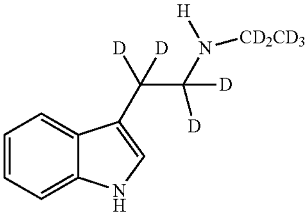

-continued

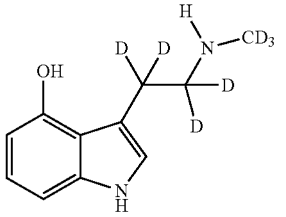

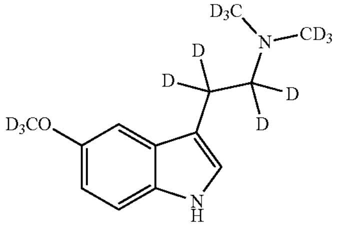

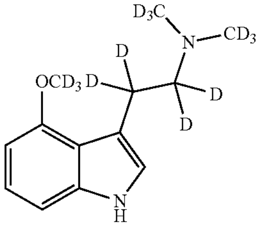

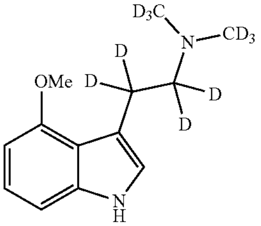

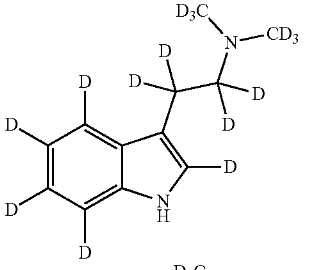

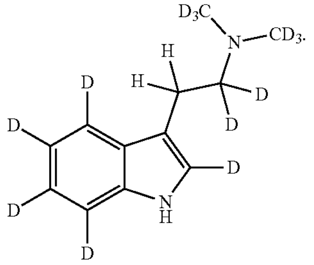

For some embodiments, the compound has the following structure:

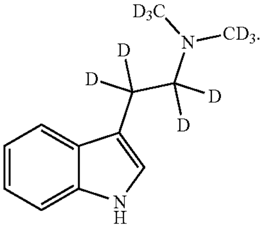 [SMILES: [2H]C([2H])([2H])N(C([2H])([2H])[2H])C([2H])([2H])C([2H])([2H])c1c[nH]c2ccccc12]

For some embodiments, the compounds described herein have at least one of $R_2$, $R_4$, $R_5$, $R_6$, $R_7$, $R_9$, and $R_{10}$ is deuterium or substituted with a deuterium.

For some embodiments, the compounds described herein have at least one of $R_2$, $R_4$, $R_5$, $R_6$, and $R_7$ is deuterium or substituted with a deuterium.

For some embodiments, $R_2$ of the compounds described herein is deuterium or substituted with a deuterium.

For some embodiments, $R_4$ of the compounds described herein is deuterium or substituted with a deuterium.

For some embodiments, $R_5$ of the compounds described herein is deuterium or substituted with a deuterium.

For some embodiments, $R_6$ of the compounds described herein is deuterium or substituted with a deuterium.

For some embodiments, $R_7$ of the compounds described herein is deuterium or substituted with a deuterium.

For some embodiments, $R_9$ of the compounds described herein is deuterium or substituted with a deuterium.

For some embodiments, $R_{10}$ of the compounds described herein is deuterium or substituted with a deuterium.

For some embodiments, $R_6$ and/or $R_7$ of the compounds described herein is halogen.

For some embodiments, $R_4$ and/or $R_5$ of the compounds described herein is deuterium or substituted with a deuterium.

For some embodiments, the compound is an agonist of a serotonin 5-$HT_2$ receptor.

For some embodiments, the compound can be agonists of a serotonin 5-$HT_{2A}$ receptor.

Without being bound to any particular theory, it is believed that the novel compounds described herein having selective deuteration, like in the exocyclic moiety, allow for significant slowing of enzymatic degradation with improved exposure (i.e., prevention of high drug concentrations (spiking) observed acutely after administration) and increased blood-to-brain ratio, resulting in enhanced oral bioavailability. Some compounds described herein confer similar benefits by selective deuteration of the phenyl ring.

Also disclosed herein is a pharmaceutical composition comprising a compound as disclosed herein and a pharmaceutically acceptable vehicle.

"Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy. Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; administration by inhalation via, for example a nebulizer or inhaler, and parenteral administration.

In some embodiments, the compositions include a compound as disclosed herein at a purity of at least 50% by weight of the total amount of isotopologues of formula present. In some embodiments, any position in the compound having deuterium has a minimum deuterium incorporation of at least 45% at the deuterium. In some embodiments, the composition is substantially free of other isotopologues of the compound.

In some embodiments, the pharmaceutical composition includes: (i) a water-insoluble neutrally charged non-ionic matrix; and (ii) a polymer carrying one or more negatively charged groups.

In some embodiments, the non-ionic matrix is selected from cellulose-based polymers such as HPMC, alone or enhanced by mixing with components such as starches; waxes; neutral gums; polymethacrylates; PVA; PVA/PVP blends; or mixtures thereof. In some embodiments, the cellulose-based polymer is hydroxypropyl methylcellulose (HPMC).

In some embodiments, the polymer carrying one or more negatively charged groups is polyacrylic acid, polylactic acid, polyglycolic acid, polymethacrylate carboxylates, cation-exchange resins, clays, zeolites, hyaluronic acid, anionic gums, salts thereof, or mixtures thereof.

In some embodiments, the anionic gum is a naturally occurring material or a semi-synthetic material. In some embodiments, the naturally occurring material is alginic acid, pectin, xanthan gum, carrageenan, locust bean gum, gum arabic, gum karaya, guar gum, gum tragacanth, or mixtures thereof. In some embodiments, the semi-synthetic material is carboxymethyl-chitin, cellulose gum, or mixtures thereof.

In some embodiments, provided is a modified release oral formulation. In some embodiments, the oral formulation is for low dose maintenance therapy that can be constructed using either deuterated or non-deuterated tryptamines, capitalizing on the ability of tryptamines to bind with anionic polymers.

The pharmaceutical composition may be prepared and administered in a wide variety of dosage formulations. Compounds described may be administered orally, rectally, via inhalation, or by injection (e.g., intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets can contain from about 5% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from about 0.001 mg to about 10 mg (e.g., about 0.001, 0.005, 0.01, 0.05, 0.1, 0.5, 1.0, 2.0, 3.0, 4.0, 5.0, 6.0, 7.0, 8.0, 9.0, 10.0 mg or more; or any range between about 0.001 and about 10.0 mg (e.g., between about 0.0001 and about 0.1, between about 0.1 and 1.0, between about 0.0005 and 0.5, or between about 0.01 and about 2.0 mg), according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided dug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Also disclosed is a method of treating a subject with a disease or disorder comprising administering to the subject a therapeutically effective amount of a compound as disclosed herein.

Also disclosed is a method of treating a subject with a disease or disorder comprising administering to the subject a therapeutically effective amount of a compound as disclosed herein.

Also disclosed is a method of treating a subject with a disease or disorder associated with a serotonin 5-$HT_2$ receptor comprising administering to the subject a therapeutically effective amount of a compound as disclosed herein. In some embodiments, the compound has the following structure:

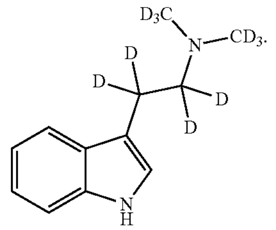 [SMILES: [2H]C([2H])([2H])N(C([2H])([2H])[2H])C([2H])([2H])C([2H])([2H])c1c[nH]c2ccccc12]

For some embodiments, the administration of the disclosed methods is by oral, sublingual, buccal, parenteral, topical, nasal, inhalation, or injectable mute.

For some embodiments, the disease or disorder is selected from the group consisting of central nervous system (CNS) disorders, including major depressive disorder (MDD), major depressive disorder (MDD) with suicidal ideation or suicidal behavior, suicidal ideation, suicidal behavior, non-suicidal self-injury disorder (NSSID), treatment-resistant depression (TRD), post-traumatic stress disorder (PTSD), bipolar and related disorders including bipolar I disorder, bipolar IT disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme Disease, and obesity, or combinations thereof. In some embodiments, the disease or disorder is alcohol use disorder.

For some embodiments, the disease or disorder includes conditions of the autonomic nervous system (ANS).

For some embodiments, the disease or disorder includes pulmonary disorders including asthma and chronic obstructive pulmonary disorder (COPD).

For some embodiments, the disease or disorder includes cardiovascular disorders including atherosclerosis.

Also disclosed is a method of treating a subject with alcohol use disorder associated with a serotonin 5-$HT_2$ receptor comprising administering to the subject a therapeutically effective amount of a compound having the following structure:

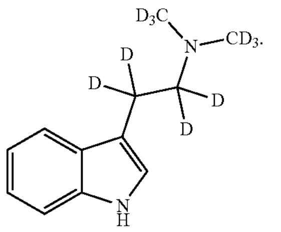 [SMILES: [2H]C([2H])([2H])N(C([2H])([2H])[2H])C([2H])([2H])C([2H])([2H])c1c[nH]c2ccccc12]

Formulations

Also disclosed herein is a pharmaceutical composition, e.g., a pharmaceutical composition formulated for oral administration, such as pills (e.g., tablets, capsules, caplets, troaches, lozenges, caches, gelcaps, caps, pellets, holuses, pastilles, orally disintegrating tablets, sublingual tablets and buccal tablets), formulated for oral administration, e.g., single-layer tablet composition, comprising a tryptamine derivative, such as DMT, 5-MeO-DMT, psilocybin, and psilocin, or any of the compounds described herein, or a pharmaceutically acceptable salt thereof, with reduced neurological adverse effects compared to existing oral formulations. The pharmaceutical composition is formulated to ensure the steady release of a therapeutically effective concentration of tryptamine derivatives described herein from an oral pharmaceutical composition without sedative or psychotomimetic toxic spikes in plasma concentration of any of the compounds described herein (e.g., a tryptamine derivative, such as DMT, 5-MeO-DMT, psilocybin, and psilocin, or any of the compounds described herein, or a pharmaceutically acceptable salt thereof). Such spikes in plasma concentration have been well-documented to have serious psychotomimetic directed side effects including, but not limited to hallucination, dizziness, and nausea; which can not only have immediate repercussions, but also adversely affect treatment compliance. In this regard, the disclosure provides novel and inventive formulations for oral administration comprising, e.g., optimal matrices discovered for the long-term steady release of a tryptamine derivative, such as DMT, 5-MeO-DMT, psilocybin, and psilocin, or any of the compounds described herein, or a pharmaceutically acceptable salt thereof, with reduced sedative and psychotomimetic side effects.

In some embodiments, the pharmaceutical composition (e.g., a tablet composition formulated for oral administration such as a single-layer tablet composition), comprises any of the compounds described herein (e.g., a tryptamine derivative, such as DMT, 5-MeO-DMT, psilocybin, and psilocin, or any of the compounds described herein), or a pharmaceutically acceptable salt thereof. In some embodiments, the compound has the following structure:

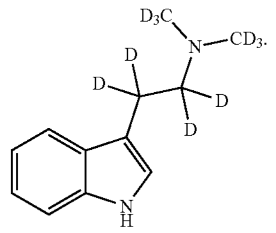 [SMILES: [2H]C([2H])([2H])N(C([2H])([2H])[2H])C([2H])([2H])C([2H])([2H])c1c[nH]c2ccccc12]

In some embodiments of the disclosure, the tablet composition is a modified-release tablet adapted for sustained release, e.g., maximum sustained release.

In some embodiments of the disclosure, the tablet composition is adapted for tamper resistance. In some embodiments, the tablet composition comprises polyethylene oxide (PEO), e.g., MW about 2,000 to about 7,000 KDa, in combination with HPMC. In some embodiments, the tablet composition may further comprise polyethylene glycol (PEG), e.g., PEG 8K. In some embodiments, the tablet composition may further comprise polymer carrying one or more negatively charged groups, e.g., polyacrylic acid. In specific embodiments, the tablet composition comprising PEO is further subjected to heating/annealing, e.g., extrusion conditions.

In some embodiments of the disclosure, the pharmaceutical composition comprises a combination of (i) a water-insoluble neutrally charged non-ionic matrix; (ii) a polymer carrying one or more negatively charged groups; and (iii) a tryptamine derivative, such as DMT, 5-MeO-DMT, psilocybin, and psilocin, or any of the compounds described herein, or a pharmaceutically acceptable salt thereof.

In some embodiments of the disclosure, the polymer carrying one or more negatively charged groups is polyacrylic acid, polylactic acid, polyglycolic acid, polymethacrylate carboxylates, cation-exchange resins, clays, zeolites, hyaluronic acid, anionic gums, salts thereof, or mixtures thereof. In some embodiments, the anionic gum is a naturally occurring material, a semi-synthetic material, or a combination thereof. In some embodiments, the naturally occurring material is alginic acid, pectin, xanthan gum, carrageenan, locust bean gum, gum arabic, gum karaya, guar gum, gum tragacanth, or combinations thereof. In another embodiment, the semi-synthetic material is carboxymethylchitin, cellulose gum, or combinations thereof.

Moreover, without wishing to be bound by theory, in some embodiments, the role of the polymer carrying one or more negatively charged groups, e.g., moieties of acidic nature as in those of the acidic polymers described herein, surprisingly offers significant retention of a tryptamine derivative, such as DMT, 5-MeO-DMT, psilocybin, and psilocin, or any of the compounds described herein, or a pharmaceutically acceptable salt thereof, in the matrix. In some embodiments, this negative charge may be created in situ, for example, based on release of a proton due to pKa and under certain pH conditions or through electrostatic interaction/creation of negative charge. Further noting that acidic polymers may be the salts of the corresponding weak acids that will be the related protonated acids in the stomach; which, and without wishing to be bound by theory, will neutralize the charge and may reduce the interactions of the tryptamine derivative, such as DMT, 5-MeO-DMT, psilocybin, and psilocin, or any of the compounds described herein, or a pharmaceutically acceptable salt thereof, with the matrix. In addition, the release matrix may be further complemented by other inactive pharmaceutical ingredients to aid in preparation of the appropriate solid dose form such as fillers, disintegrants, flow improving agents, lubricants, colorants, and taste maskers.

In some embodiments of the disclosure, the tablet composition is adapted for tamper resistance. In some embodiments, the tablet composition comprises polyethylene oxide (PEO), e.g., MW about 2,000 to about 7,000 KDa. In specific embodiments, the tablet composition comprising PEO is further subjected to heating/annealing, e.g., extrusion.

In some embodiments of the disclosure, the non-ionic matrix is selected from cellulose-based polymers such as HPMC, alone or enhanced by mixing with components such as starches; waxes; neutral gums; polymethacrylates; PVA; PVA/PVP blends; or mixtures thereof.

In some embodiments of the disclosure, the cellulose-based polymer is hydroxypropyl methylcellulose (HPMC). In some embodiments, the tablet composition comprises about 20-60% hydroxypropyl methylcellulose by weight, about 10-30% starch by weight, or any combination thereof.

In some embodiments, the tablet composition comprises a therapeutically effective amount of any of the compounds described herein for the treatment of pain. In some embodiments, the pain treated is cancer pain, e.g., refractory cancer pain. In some embodiments, the pain treated is post-surgical pain. In some embodiments, the pain treated is orthopedic pain. In some embodiments, the pain treated is back pain. In some embodiments, the pain treated is neuropathic pain. In some embodiments, the pain treated is dental pain. In some embodiments, the pain treated is chronic pain in opioid-tolerant patients.

In some embodiments, the tablet composition comprises a therapeutically effective amount of any of the compounds described herein for the treatment of depression.

In some embodiments, the tablet composition comprises a therapeutically effective amount of any of the compounds described herein for the treatment of brain injury.

In some embodiments, the tablet composition comprises a therapeutically effective amount of any of the compounds described herein for the treatment of stroke.

In some embodiments, the tablet composition comprises a therapeutically effective amount of any of the compounds described herein for use in migraine, e.g., with aura.

In some embodiments, the tablet composition comprises a therapeutically effective amount of any of the compounds described herein for use in refractory asthma.

In some embodiments, the tablet composition comprises a therapeutically effective amount of any of the compounds described herein for use in treating alcohol dependence.

In some embodiments, the tablet composition comprises a therapeutically effective amount of any of the compounds described herein for use in treating post-traumatic stress disorder (PTSD).

In some embodiments, the tablet composition comprises a therapeutically effective amount of any of the compounds described herein for use in treating depression (e.g., treatment resistant depression (TRD) or bipolar depression).

In some embodiments, the tablet composition comprises a therapeutically effective amount of any of the compounds described herein for use in treating major depressive disorder (MDD).

In some embodiments, the tablet composition comprises a therapeutically effective amount of any of the compounds described herein for use in treating anxiety (e.g., generalized anxiety disorder).

In some embodiments the tablet composition comprises a therapeutically effective amount of any of the compounds described herein for use in treating schizophrenia.

In some embodiments, the tablet composition comprises a therapeutically effective amount of any of the compounds described herein for use in treating bipolar disorder.

In some embodiments, the tablet composition comprises a therapeutically effective amount of any of the compounds described herein for use in treating suicidality or suicidal ideation.

In some embodiments, the tablet composition comprises a therapeutically effective amount of any of the compounds described herein for use in treating autism.

In some embodiments, the tablet composition comprises a therapeutically effective amount of any of the compounds described herein for use in treating diabetic neuropathy.

In some embodiments, the tablet composition comprises a therapeutically effective amount of any of the compounds described herein for use in treating neuropathic pain.

In some embodiments, the tablet composition comprises a therapeutically effective amount of any of the compounds described herein for use in treating acute pain (e.g., acute trauma pain).

In some embodiments, the tablet composition comprises a therapeutically effective amount of any of the compounds described herein for use in treating chronic pain.

In some embodiments, the tablet composition comprises a therapeutically effective amount of any of the compounds described herein for use in treating levodopa-induced dyskinesia.

In some embodiments, the tablet composition comprises a therapeutically effective amount of any of the compounds described herein for use in treating or modulating a pseudobulbar effect or Bulbar function.

In some embodiments, the tablet composition comprises a therapeutically effective amount of any of the compounds described herein for use in treating Alzheimer's disease or conditions associated with Alzheimer's disease (e.g., Alzheimer's dementia or Alzheimer's agitation).

In some embodiments, the tablet composition comprises a therapeutically effective amount of any of the compounds described herein for use in treating tinnitus.

In some embodiments, the tablet composition comprises a therapeutically effective amount of any of the compounds described herein for use in treating a disease or disorder associated with a serotonin 5-$HT_2$ receptor.

For some embodiments, the disease or disorder is selected from the group consisting of central nervous system (CNS) disorders, including major depressive disorder (MDD), major depressive disorder (MDD) with suicidal ideation or suicidal behavior, suicidal ideation, suicidal behavior, non-suicidal self-injury disorder (NSSID), treatment-resistant depression (TRD), post-traumatic stress disorder (PTSD), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme Disease, and obesity, or combinations thereof. In some embodiments, the disease or disorder is alcohol use disorder.

For some embodiments, the disease or disorder includes conditions of the autonomic nervous system (ANS).

For some embodiments, the disease or disorder includes pulmonary disorders including asthma and chronic obstructive pulmonary disorder (COPD).

For some embodiments, the disease or disorder includes cardiovascular disorders including atherosclerosis.

Depression, anxiety, or stress can be common among patients who have chronic and/or life-threatening illnesses such as Alzheimer's disease, autoimmune diseases (e.g., systemic lupus erythematosus, rheumatoid arthritis, and psoriasis), cancer, coronary heart disease, diabetes, epilepsy, HIV/AIDS, hypothyroidism, multiple sclerosis. Parkinson's disease, and stroke. Symptoms of depression, anxiety, or stress can occur after diagnosis with the disease or illness. Patients that have depression, anxiety, or stress concurrent with another medical disease or illness can have more severe symptoms of both illnesses and symptoms of depression, anxiety, or stress can continue even as a patient's physical health improves. Compounds and formulations described herein can be used to treat depression associated with a chronic or life-threatening disease or illness.

In some embodiments, the tablet composition comprises an amount of any of the compounds described herein released from the matrix with a rate 0.05-2 mg/kg/h over a period of 12-24 hours, e.g., 24 hours.

In some embodiments of the disclosure, the composition achieves a combined concentration of a tryptamine derivative, such as DMT, 5-MeO-DMT, psilocybin, and psilocin, or any of the compounds described herein, or a pharmaceutically acceptable salt thereof, in plasma in the range of about 10-500 ng/ml (e.g., about 10, 20, 30, 40, 50, 100, 150, 200, 250, 300, 350, 400, 450, 500 or more ng/ml (or any range between about 10 and about 500 ng/ml, e.g., about 100 to about 300 ng/ml, about 250 to about 450 ng/ml, or about 50 to about 400 ng/ml), and maintains this concentration for duration of the release period. In some embodiments, the composition achieves a combined concentration of a tryptamine derivative, such as DMT, 5-MeO-DMT, psilocybin, and psilocin, or any of the compounds described herein, or a pharmaceutically acceptable salt thereof, in plasma in the range of about 10-300 ng/ml, and maintains this concentration for duration of the release period. In some embodiments, the composition achieves a combined concentration of a tryptamine derivative, such as DMT, 5-MeO-DMT, psilocybin, and psilocin, or any of the compounds described herein, or a pharmaceutically acceptable salt thereof, in plasma in the range of about 10-100 ng/ml, or about 50-100 ng/ml, and maintains this concentration for duration of the release period. In some embodiments, the composition achieves a combined concentration of a tryptamine derivative, such as DMT, 5-MeO-DMT, psilocybin, and psilocin, or any of the compounds described herein, or a pharmaceutically acceptable salt thereof, in plasma in the range of about 10-20 ng/ml, and maintains this concentration for duration of the release period.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is 4 hours or less, 3 hours or less, 2 hours or less, or 1 hour or less.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than 4 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than about 8 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than about 12 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than about 16 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than about 20 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than or equal to about 24 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than or equal to about 28 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than or equal to about 32 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is greater than or equal to about 36 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is less than about 48 hours.

In some embodiments of the disclosure, the release period of a tryptamine derivative, such as DMT, 5-MeO-DMT, psilocybin, and psilocin, or any of the compounds described herein, or a pharmaceutically acceptable salt thereof, in the formulations of the disclosure is less than about 36 hours.

In some embodiments of the disclosure, the tablet compositions of the disclosure are utilized as a 2-times a day (BID), 3-times a day (TID) or 4-times a day (QID) application.

In some embodiments of the disclosure, the tablet compositions of the disclosure are utilized as a once a day (QD) application.

In some embodiments of the disclosure, the tablet compositions of the disclosure are utilized as a nightly (QHS) application.

In some embodiments of the disclosure, the tablet compositions of the disclosure are utilized as an as needed (PRN) application.

In some embodiments of the disclosure, the oral pharmaceutical compositions are enhanced. In some embodiments, due to the efficiency of administration, the formulation is able to utilize less of a tryptamine derivative, such as DMT, 5-MeO-DMT, psilocybin, and psilocin, for treatment to achieve the same effect as comparative oral tablets not described by the disclosure.

In some embodiments of the disclosure, the oral administration event, which provides the appropriate single unit dose, may comprise one single pill or multiple pills.

In addition, to protect the tablet from the acidic environment in the stomach and maintain a long-term release, various types of enteric coating may be used in some embodiments.

In some embodiments of the disclosure, a single-layer tablet or caplet is coated with protective layers of inactive pharmaceutical ingredients to form a modified-release formulation, e.g., to ensure steady release of the drug from the matrix and avoid concentration bursts at the early release time points.

Some embodiments of the disclosure provides formulation of a tryptamine derivative, such as DMT, 5-MeO-DMT, psilocybin, and psilocin, or any of the compounds described herein, or a pharmaceutically acceptable salt thereof as a modified-release formulation, that ensures the steady release of a therapeutically effective concentration of a tryptamine derivative, such as DMT, 5-MeO-DMT, psilocybin, and psilocin, or any of the compounds described herein, or a pharmaceutically acceptable salt thereof, from such oral modified-release formulation, without sedative or psychotomimetic toxic spikes in plasma concentration of any of the compounds described herein (e.g., a tryptamine derivative, such as DMT, 5-MeO-DMT, psilocybin, and psilocin, or any of the compounds described herein, or a pharmaceutically acceptable salt thereof). This formulation comprises a tryptamine derivative, such as DMT, 5-MeO-DMT, psilocybin, and psilocin, or any of the compounds described herein, or a pharmaceutically acceptable salt thereof, formulated in an osmotic controlled release pharmaceutical composition, such as a tablet, caplet or granules. In these formulations a single core layer containing a tryptamine derivative, such as DMT, 5-MeO-DMT, psilocybin, and psilocin, or any of the compounds described herein, or a pharmaceutically acceptable salt thereof (e.g., as defined by other tablet formulations described herein), is surrounded by semi-permeable membrane with or without drug delivery orifice. Without wishing to be bound by theory, because these systems use water osmotic pressure for the controlled delivery of the active material, delivery rates are expected to be independent of gastrointestinal conditions. In combination with the novel and inventive aspects of the disclosure, osmotic asymmetric-membrane technology or AMT (e.g., technology directed to a single-layer tablet, caplet or granules coated with an insoluble, asymmetric microporous membrane produced by controlled phase separation) may be used to produce formulations useful in the methods of treatment and kits described herein.

In some embodiments of the disclosure, a tryptamine derivative, such as DMT, 5-MeO-DMT, psilocybin, and psilocin, or any of the compounds described herein, or a pharmaceutically acceptable salt thereof, may be formulated as a pharmaceutically acceptable salt thereof, e.g., hydrochloride, aspartate, succinate, etc., such that the counterion does not significantly affect formulation as described herein for a tryptamine derivative, such as DMT, 5-MeO-DMT, psilocybin, and psilocin, or any of the compounds described herein, or a pharmaceutically acceptable salt thereof, or the ability of a tryptamine derivative, such as DMT, 5-MeO-DMT, psilocybin, and psilocin, or any of the compounds described herein, or a pharmaceutically acceptable salt thereof, to achieve the desired therapeutic effects described herein, i.e., with similar steady release of a therapeutically effective concentration (e.g., based on indication) from an oral pharmaceutical composition, such as a tablet, a caplet, a capsule, a gelcap, a cap or granules, without sedative or psychotomimetic toxic spikes in the concentration of a tryptamine derivative, such as DMT, 5-MeO-DMT, psilocybin, and psilocin, or any of the compounds described herein, or a pharmaceutically acceptable salt thereof. Exemplary salts, within this scope, may include but are not limited to: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art. Additional examples may include salts with inorganic cations such as sodium, potassium, calcium, magnesium, lithium, aluminum, zinc, etc.; and salts formed with pharmaceutically acceptable amines such as ammonia, alkylamines, hydroxyalkylamines, lysine, arginine, N-methylglucamine, procaine and the like. In specific embodiments, the pharmaceutically acceptable salt is a hydrochloride salt.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising pharmaceutical composition, such as an orally administered pharmaceutical composition like a pill, of any one of the formulations described herein comprising a tryptamine derivative, such as DMT, 5-MeO-DMT, psilocybin, and psilocin, or any of the compounds described herein, or a pharmaceutically acceptable salt thereof, and instructions for use in the treatment, prevention or management of a disease, disorder or condition, such as pain, e.g., as described herein.

In some embodiments of the disclosure, the pain treated is cancer pain, e.g., refractory cancer pain.

In some embodiments of the disclosure, the pain treated is post-surgical pain.

In some embodiments of the disclosure, the pain treated is orthopedic pain.

In some embodiments of the disclosure, the pain treated is back pain.

In some embodiments of the disclosure, the pain treated is neuropathic pain.

In some embodiments of the disclosure, the pain treated is dental pain.

In some embodiments of the disclosure, the pain treated is chronic pain in opioid-tolerant patients.

In some embodiments, the disease or disorder is a disease or disorder associated with a serotonin 5-$HT_2$ receptor.

For some embodiments, the disease or disorder is selected from the group consisting of central nervous system (CNS) disorders, including major depressive disorder (MDD), major depressive disorder (MDD) with suicidal ideation or suicidal behavior, suicidal ideation, suicidal behavior, non-suicidal self-injury disorder (NSSID), treatment-resistant depression (TRD), post-traumatic stress disorder (PTSD), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa. Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme Disease, and obesity, or combinations thereof. In some embodiments, the disease or disorder is alcohol use disorder.

For some embodiments, the disease or disorder includes conditions of the autonomic nervous system (ANS).

For some embodiments, the disease or disorder includes pulmonary disorders including asthma and chronic obstructive pulmonary disorder (COPD).

For some embodiments, the disease or disorder includes cardiovascular disorders including atherosclerosis.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising a pharmaceutical composition, such as an orally administered tablet pharmaceutical composition like a pill, of any one of the formulations of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of brain injury.

Some embodiments of the disclosure provides a kit for the treatment of a subject with a tryptamine derivative, such as DMT, formula, psilocybin, and psilocin, or any of the compounds described herein, or a pharmaceutically acceptable salt thereof, comprising a pharmaceutical composition, such as an orally administered tablet pharmaceutical composition like a pill, of any one of the formulations of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of depression.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising a pharmaceutical composition, such as an orally administered tablet pharmaceutical composition like a pill, of the formulations of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of migraine, e.g., with aura.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising a pharmaceutical composition, such as an orally administered tablet pharmaceutical composition like a pill, of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of refractory asthma.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising a pharmaceutical composition, such as an orally administered tablet pharmaceutical composition like a pill, of any one of the formulations of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of stroke.

Some embodiments of the disclosure provides a kit for the treatment of a subject with a tryptamine derivative, such as DMT, 5-MeO-DMT, psilocybin, and psilocin, or any of the compounds described herein, or a pharmaceutically acceptable salt thereof, comprising a pharmaceutical composition, such as an orally administered tablet pharmaceutical composition like a pill, of any one of the formulations of the disclosure comprising a tryptamine derivative, such as DMT, 5-MeO-DMT, psilocybin, and psilocin, or any of the compounds described herein, or a pharmaceutically acceptable salt thereof, and instructions for use in the treatment of alcohol dependence.

In some embodiments, the instructions for use form an integrated component of the packaging for the tablet composition.

In embodiments, the disclosure features an oral, modified-release pharmaceutical composition for oral administration to a subject for treating the subject diagnosed with, suffering from or susceptible to a disease, disorder or condition, such as those for which tryptamine treatment may be indicated, considered or recommended, wherein the subject is in need of treatment with said oral, modified-release pharmaceutical composition, said oral, modified-release pharmaceutical composition comprising:

(a) a drug including a tryptamine derivative, such as DMT, 5-MeO-DMT, psilocybin, and psilocin, or any of the compounds described herein, or a pharmaceutically acceptable salt thereof in an effective amount for treating, preventing and/or managing the disease, disorder, or condition in the subject; and (b) a pharmaceutically acceptable excipient;

whereby, upon oral administration of the modified-release pharmaceutical composition to the subject, a steady release of said drug from the modified-release pharmaceutical composition is maintained so that no neurologically toxic spike in the subject's plasma occurs during the release period of said drug from said pharmaceutical composition.

General Tablet Formulations

The formulations of the disclosure comprise orally administered pharmaceutical compositions, such as tablet, capsule, caplets, gelcap and cap compositions, which may include uncoated tablets or coated tablets, caplets and caps (including film-coated, sugar-coated tablets, and gastro-resistant/enteric-coated tablets). The oral pharmaceutical compositions for oral use may include the active ingredients, e.g., a tryptamine derivative, such as DMT, 5-MeO-DMT, psilocybin, and psilocin, or any of the compounds described herein, mixed with pharmaceutically acceptable inactive excipients such as diluents, disintegrating agents, binding agents, lubricating agents, powder flow improving agent, wetting agents, sweetening agents, flavoring agents, coloring agents and preservatives. Moreover, oral pharmaceutical compositions of the disclosure are solid dosage forms intended for oral administration, e.g., obtained by dry granulation with single or multiple compressions of powders or granules. In some embodiments, the oral pharmaceutical compositions may be obtained by using wet granulation techniques. In some embodiments, the oral pharmaceutical compositions may be obtained by molding, heating/annealing, or extrusion techniques.

In some embodiments, the oral tablets are right circular solid cylinders, the end surfaces of which are flat or convex, and the edges of which may be beveled. In some embodiments, the surfaces are convex. In addition, they may have lines or break-marks (scoring), symbols or other markings.

In some embodiments, the break-mark(s) is/are intended to permit accurate subdivision of the tablet in order to provide doses of less than one tablet. In some embodiments of the disclosure, the tablet compositions comprise one or more excipients such as diluents, binders, disintegrating agents, glidants, lubricants, substances capable of modifying the behavior of the dosage forms and the active ingredient(s) in the gastrointestinal tract, coloring matter authorized by the appropriate national or regional authority and flavoring substances. When such excipients are used it is necessary to ensure that they do not adversely affect the stability, dissolution rate, bioavailability, safety or efficacy of the active ingredient(s); there must be no incompatibility between any of the components of the dosage form.

Coated tablets are tablets covered with one or more layers of mixtures of substances such as natural or synthetic resins, polymers, gums, fillers, sugars, plasticizers, polyols, waxes, coloring matters authorized by the appropriate national or regional authority, and flavoring substances. Such coating materials do not contain any active ingredient, e.g., a tryptamine derivative, such as DMT, 5-MeO-DMT, psilocybin, and psilocin, or any of the compounds described herein, or a pharmaceutically acceptable salt thereof. The tablets may be coated for a variety of reasons such as protection of the active ingredients from burst release from the matrix, air, moisture or light, masking of unpleasant tastes and odors or improvement of appearance. The substance used for coating may be applied as a solution or suspension.

In some embodiments, the manufacturing processes for the oral pharmaceutical compositions, e.g., tablets, meet the requirements of good manufacturing practices (GMP). In some embodiments, one or more measures are taken in the manufacture of oral pharmaceutical compositions selected from the following: ensure that mixing with excipients is carried out in a manner that ensures homogeneity; ensure that the oral pharmaceutical compositions possess a suitable mechanical strength to avoid crumbling or breaking on subsequent processing, e.g., coating, storage and distribution; minimize the degradation of the active ingredient; minimize the risk of microbial contamination; minimize the risk of cross-contamination. In addition, in the manufacture of scored tablets (tablets bearing a break-mark or marks) for which subdivision is intended in order to provide doses of less than one tablet measures are taken to: ensure the effectiveness of break-marks with respect to the uniformity of mass or content, as appropriate, of the subdivided parts so that the patient receives the intended close.

In general a suitable dose will be in the range of about 0.01 to about 10 mg per kilogram body weight of the recipient per day, e.g., in the range of about 0.1 to about 5 mg per kilogram body weight per day. Additional details on techniques for formulation and administration are well described in the scientific and patent literature, see, e.g., the latest edition of Remington's Pharmaceutical Sciences. Maack Publishing Co. Easton Pa. ("Remington's"). After a pharmaceutical composition has been formulated in an acceptable carrier, it can be placed in an appropriate container and labeled for treatment of an indicated condition). For administration of the formulations comprising any of the compounds described herein (e.g., a tryptamine derivative, such as DMT, 5-MeO-DMT, psilocybin, and psilocin, or any of the compounds described herein), or a pharmaceutically acceptable salt thereof, such labeling would include, e.g., instructions concerning the amount, frequency, method of administration, treatment regimen and indications.

Compliance with Monographs

In some embodiments, the formulations of the disclosure conform to certain industry accepted monographs to afford compliance with the Federal Food Drug and Cosmetic Act. In particular, the formulations of the disclosure conform and are considered acceptable under visual inspection, uniformity of mass analysis, uniformity of content analysis, and/or dissolution/disintegration analysis all of which are established by a relevant monograph.

In some embodiments, throughout manufacturing certain procedures are validated and monitored by carrying out appropriate in-process controls. These are designed to guarantee the effectiveness of each stage of production. In-process controls during tablet production may include the moisture content of the final lubricated blend, the size of granules, the flow of the final mixture and, where relevant, the uniformity of mass of tablet cores before coating. In-process controls during tablet production may also include the dimensions (thickness, diameter), uniformity of mass, hardness and/or crushing force, friability, disintegration or dissolution rate (for example, for modified-release tablets) of the finished dosage form. Suitable test methods that may be used to demonstrate certain of these attributes are known in the art.

In some embodiments, packaging maybe or is required to be adequate to protect the pharmaceutical compositions, including tablets, from light, moisture and damage during transportation.

In additional embodiments, the commercially available formulation (e.g., kit) complies with the labeling requirements established under Good Manufacturing Practices (GMP). Such label includes:

(1) the name of the pharmaceutical product;
(2) the name(s) of the active ingredient(s); International Nonproprietary Names (INN) should be used wherever possible;
(3) the amount of the active ingredient(s) in each tablet and the number of tablets in the container;
(4) the batch (lot) number assigned by the manufacturer;
(5) the expiry date and, when required, the date of manufacture;
(6) any special storage conditions or handling precautions that may be necessary; (7) directions for use, warnings, and precautions that may be necessary;
(8) the name and address of the manufacturer or the person responsible for placing the product on the market;
(9) for scored tablets where the directions for use include subdivision to provide doses of less than one tablet, the label should also include: the storage conditions for and the period of use of those subdivided part(s) not immediately taken or administered.

In some embodiments, the pharmaceutical compositions, e.g., tablets, are able to withstand handling, including packaging and transportation, without losing their integrity.

The formulations of the disclosure may be used in the methods of the disclosure, e.g., methods of treatment of the disclosure. As such, the disclosure relates to the method of use of formulations or compositions (e.g., pharmaceutical compositions) of the disclosure, which contain a tryptamine derivative, such as DMT, 5-MeO-DMT, psilocybin, and psilocin, or any of the compounds described herein, or a pharmaceutically acceptable salt thereof, e.g., for the treatment of pain. As such, in some embodiments, the disclosure provides for the management of different kinds of pain, including but not limited to refractory cancer pain, neurologic pain, postoperative pain, complex regional pain syndrome (CRPS), migraine, e.g., with aura, and other conditions including depression, alcohol dependence, refractory asthma, epilepsy, acute brain injury and stroke, Alzheimer's disease and other disorders comprising an oral administration of the formulations of the disclosure, described herein. In some embodiments, the use of formulations of the disclosure may be used as a standalone therapy. In some embodiments, the use of formulations of the disclosure may be used as an adjuvant/combination therapy.

In some embodiments, the disclosure provides for the management of different kinds of pain, including but not limited to cancer pain, e.g., refractory cancer pain; neuropathic pain; opioid-induced hyperalgesia and opioid-related tolerance; neurologic pain; postoperative/post-surgical pain; complex regional pain syndrome (CRPS); shock; limb amputation; severe chemical or thermal burn injury; sprains, ligament tears, fractures, wounds and other tissue injuries; dental surgery, procedures and maladies; labor and delivery; during physical therapy; radiation poisoning; acquired immunodeficiency syndrome (AIDS); epidural (or peridural) fibrosis; orthopedic pain; back pain; failed back surgery and failed laminectomy; sciatica; painful sickle cell crisis; arthritis; autoimmune disease; intractable bladder pain; pain associated with certain viruses, e.g., shingles pain or herpes pain; acute nausea, e.g., pain that may be causing the nausea or the abdominal pain that frequently accompanies sever nausea; migraine, e.g., with aura; and other conditions including depression (e.g., acute depression or chronic depression), depression along with pain, alcohol dependence, acute agitation, refractory asthma, acute asthma (e.g., unrelated pain conditions can induce asthma), epilepsy, acute brain injury and stroke, Alzheimer's disease and other disorders. In addition, the disclosure includes the treatment/management of any combination of these types of pain or conditions.

In some embodiments, the pain treated/managed is acute breakthrough pain or pain related to wind-up that can occur in a chronic pain condition.

In some embodiments of the disclosure, the pain treated/managed is cancer pain, e.g., refractory cancer pain.

In some embodiments of the disclosure, the pain treated/managed is post-surgical pain.

In some embodiments of the disclosure, the pain treated/managed is orthopedic pain.

In some embodiments of the disclosure, the pain treated/managed is back pain.

In some embodiments of the disclosure, the pain treated/managed is neuropathic pain.

In some embodiments of the disclosure, the pain treated/managed is dental pain.

In some embodiments of the disclosure, the condition treated/managed is depression.

In some embodiments of the disclosure, the pain treated/managed is chronic pain in opioid-tolerant patients.

In embodiments, the disclosure relates to a method of treating a disease or condition by modulating NMDA activity, where the method comprises administering an effective amount of any of the compounds described herein (e.g., a tryptamine derivative, such as DMT, 5-MeO-DMT, psilocybin, and psilocin, or any of the compounds described herein) to a subject in need thereof. In embodiments, the disease or condition is selected from: levodopa-induced dyskinesia; dementia (e.g., Alzheimer's dementia), tinnitus, treatment resistant depression (TRD), major depressive disorder, neuropathic pain, agitation resulting from or associated with Alzheimer's disease, pseudobulbar effect, autism, Bulbar function, generalized anxiety disorder, Alzheimer's disease, schizophrenia, diabetic neuropathy, acute pain, depression, bipolar depression, suicidality, neuropathic pain, or post-traumatic stress disorder (PTSD). In embodiments, the disease or condition is a psychiatric or mental disorder (e.g., schizophrenia, mood disorder, substance induced psychosis, major depressive disorder (MDD), bipolar disorder, bipolar depression (BDep), post-traumatic stress disorder (PTSD), suicidal ideation, anxiety, obsessive compulsive disorder (OCD), and treatment-resistant depression (TRD)). In other embodiments, the disease or condition is a neurological disorder (e.g., Huntington's disease (HD), Alzheimer's disease (AD), or systemic lupus erythematosus (SLE)).

For example, in some embodiments, the disclosure provides a method of treating a subject with a tryptamine derivative, such as DMT, 5-MeO-DMT, psilocybin, and psilocin, or any of the compounds described herein, or a pharmaceutically acceptable salt thereof, comprising the step of administering to a subject an orally administered tablet composition, e.g., matrix composition, of the disclosure comprising a tryptamine derivative, such as DMT, 5-MeO-DMT, psilocybin, and psilocin, or any of the compounds described herein, or a pharmaceutically acceptable salt thereof, such that the subject is treated.

The administering physician can provide a method of treatment that is prophylactic or therapeutic by adjusting the amount and timing of a tryptamine derivative, such as DMT, 5-MeO-DMT, psilocybin, and psilocin, or any of the compounds described herein, or a pharmaceutically acceptable salt thereof, administration on the basis of observations of one or more symptoms of the disorder or condition being treated.

In some embodiments, the disclosure provides a method of continuous oral administration of a tryptamine derivative, such as DMT, 5-MeO-DMT, psilocybin, and psilocin, or any of the compounds described herein, or a pharmaceutically acceptable salt thereof, into a tablet, e.g., single-layer tablet, that provides a steady release of a therapeutically effective concentration of a tryptamine derivative, such as DMT, 5-MeO-DMT, psilocybin, and psilocin, or any of the compounds described herein, or a pharmaceutically acceptable salt thereof, from an oral tablet over a complete release period without neurologically toxic spikes, e.g., no sedative or psychotomimetic toxic spikes in plasma concentration of a tryptamine derivative, such as DMT, 5-MeO-DMT, psilocybin, and psilocin, or any of the compounds described herein, or a pharmaceutically acceptable salt thereof, to produce a tablet composition, e.g., single-layer tablet composition; and orally administering the tablet composition to a subject, such that a continuous therapeutically effective concentration of a tryptamine derivative, such as DMT, 5-MeO-DMT, psilocybin, and psilocin, or any of the compounds described herein, or a pharmaceutically acceptable salt thereof, is provided to the subject.

In some embodiments of the disclosure, the subject is a mammal.

In some embodiments of the disclosure, the mammal is a human.

In some embodiments, the disclosure provides a method of formulating a tryptamine derivative, such as DMT, 5-MeO-DMT, psilocybin, and psilocin, or any of the compounds described herein, or a pharmaceutically acceptable salt thereof, to ensure the steady release of a therapeutically effective concentration of a tryptamine derivative, such as DMT, 5-MeO-DMT, psilocybin, and psilocin, or any of the compounds described herein, or a pharmaceutically acceptable salt thereof, from an oral tablet without neurologically toxic spikes, e.g., sedative or psychotomimetic toxic spikes, in plasma concentration of a tryptamine derivative, such as DMT, 5-MeO-DMT, psilocybin, and psilocin, or any of the compounds described herein, or a pharmaceutically acceptable salt thereof. In some embodiments, the method comprises the step of combining (i) a water-insoluble neutrally charged non-ionic matrix; (ii) a polymer carrying one or more negatively charged groups; and (iii) a tryptamine derivative, such as DMT, 5-MeO-DMT, psilocybin, and psilocin, or any of the compounds described herein, or a pharmaceutically acceptable salt thereof, to produce an orally administered tablet composition, e.g., single-layer. In some embodiments, the method comprises the step of combining (i) polyethylene oxide (PEO), e.g., MW about 2.000 to about 7,000 KDa, with HPMC, and (ii) a tryptamine derivative, such as DMT, 5-MeO-DMT, psilocybin, and psilocin, or any of the compounds described herein, or a pharmaceutically acceptable salt thereof, to produce an orally administered tablet composition, e.g., single-layer. In some embodiments, the method comprises the step of combining polyethylene oxide (PEO) with HPMC, and a tryptamine derivative, such as DMT, 5-MeO-DMT, psilocybin, and psilocin, or any of the compounds described herein, or a pharmaceutically acceptable salt thereof, the tablet composition may further comprise polyethylene glycol (PEG), e.g., PEG 8K, a polymer carrying one or more negatively charged groups, e.g., polyacrylic acid and/or may be further subjected to heating/annealing, e.g., extrusion conditions. In some embodiments, the formulations of the disclosure may be administered in combination with other active therapeutic agents, e.g., opioids to reduce pain. In some embodiments, the formulations of the disclosure serve to reduce the amount of opioids necessary to treat a patient.

In some embodiments, the formulations of the disclosure are not administered in combination with other active therapeutic agents.

In some embodiments, the formulations of the disclosure may be administered in combination with another formulation of tryptamine or derivatives thereof, e.g., a fast release formulation tryptamine or derivatives thereof.

In some embodiments, the disclosure provides a method of formulating a tryptamine derivative, such as DMT, 5-MeO-DMT, psilocybin, and psilocin, or any of the compounds described herein, or a pharmaceutically acceptable salt thereof, to ensure the steady release of a therapeutically effective concentration of the a tryptamine derivative, such as DMT, 5-MeO-DMT, psilocybin, and psilocin, or any of the compounds described herein, or a pharmaceutically acceptable salt thereof, from an oral tablet without sedative or psychotomimetic toxic spikes in plasma concentration of the a tryptamine derivative, such as DMT, 5-MeO-DMT, psilocybin, and psilocin, or any of the compounds described herein, or a pharmaceutically acceptable salt thereof. The method comprises formulation of a tryptamine derivative, such as DMT, 5-MeO-DMT, psilocybin, and psilocin, or any of the compounds described herein, or a pharmaceutically acceptable salt thereof, in an osmotic controlled release tablet. In these formulations the single core layer containing a tryptamine derivative, such as DMT, 5-MeO-DMT, psilocybin, and psilocin, or any of the compounds described herein, or a pharmaceutically acceptable salt thereof, is surrounded by semi-permeable membrane with or without drug delivery orifice. In some embodiments, combination with the novel and inventive pharmaceutical compositions (e.g., a tryptamine derivative, such as DMT, 5-MeO-DMT, psilocybin, and psilocin, or any of the compounds described herein, or a pharmaceutically acceptable salt thereof), of the disclosure and osmotic asymmetric-membrane technology or AMT (e.g., technology directed to a single-layer tablet coated with an insoluble, asymmetric microporous membrane produced by controlled phase separation) may be used to produce formulations useful in the methods and kits described herein.

EXAMPLES

Example 1. Synthesis of PI-α,α-$d_2$

Synthesis of PI-α,α-$d_2$ started with 4-oxybenzylindole that is iminoformylated by formaldehyde/dimethylamine and then converted to the 3-acetic acid derivative using potassium cyanide in acidic conditions. Subsequent treatment with thionyl chloride and dimethylamine produces a related amide that is reduced by $LiAlD_4$, which inserts a deuteromethylene group in the α-position. In the final step, the —OBz protective group is removed by hydrogen gas over a palladium catalyst to produce a final compound. The structure of the product has been confirmed by $^1H$ NMR and LC-MS.

Scheme 1. Synthesis of PI-α,α-$d_2$.

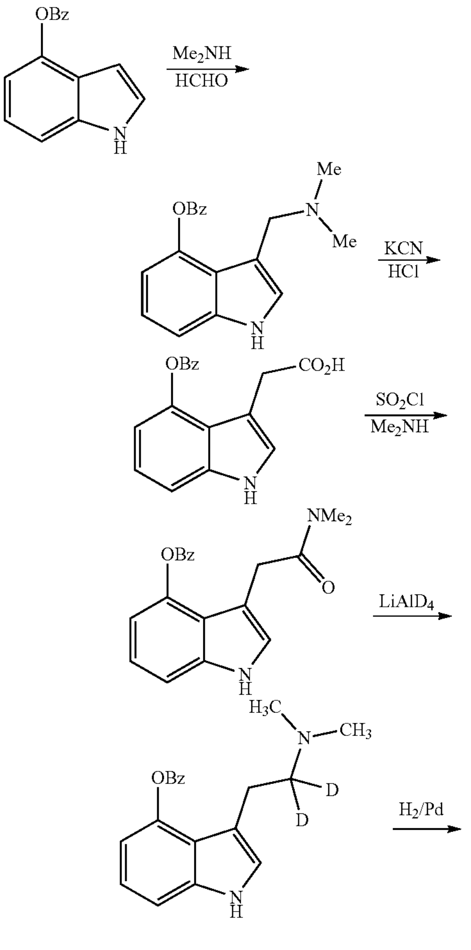

-continued

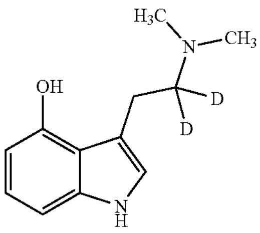

Example 2. Synthesis of DMT-$d_{10}$

Synthesis of DMT-$d_{10}$ started with indole that is first acylated by oxalyl chloride and then converted to the related amide by treatment with dimethyl amine-$d_6$. Subsequent reduction with $LiAlD_4$ leads to the final product. The structure of the material has been confirmed by $^1H$ NMR and LC-MS.

Example 3. Synthesis of 5-$CD_3$O-DMP-α,α,5,5,5-$d_5$

Synthesis of 5-$CD_3$O-DMP-α,α,5,5,5-$d_5$ has been conducted analogously to DMT-α,α-$d_2$ described in the Example 2 starting from 5-deuteromethoxy indole prepared by the methylation of 5-hydroxyindole using deuteromethyl iodide. The structure of the product has been confirmed by $^1H$ NMR and LC-MS.

Example 4. Synthesis of Aer-α,α,-$d_2$

Synthesis of Aer-α,α-$d_2$ has been conducted using an —OBz bis-deuterated tryptamine intermediate obtained as described in the Example 1. That material has been alkylated with methylamine and then reduced by hydrogen on palladium to obtain a final product as an iodide salt (Scheme 2). The structure of the product has been confirmed by $^1H$ NMR and LC-MS.

Scheme 2. Synthesis of Aer-α,α,-$d_2$

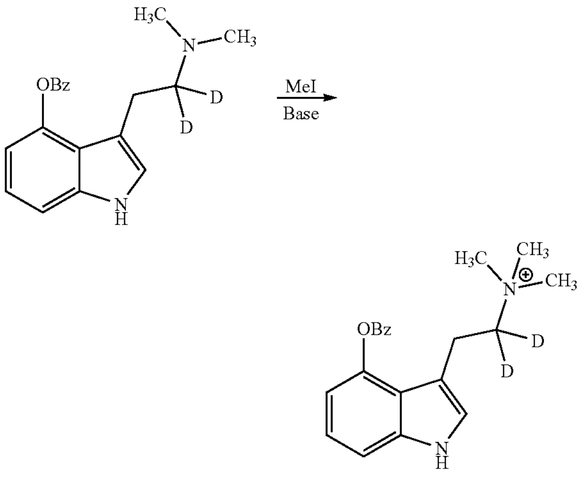

-continued

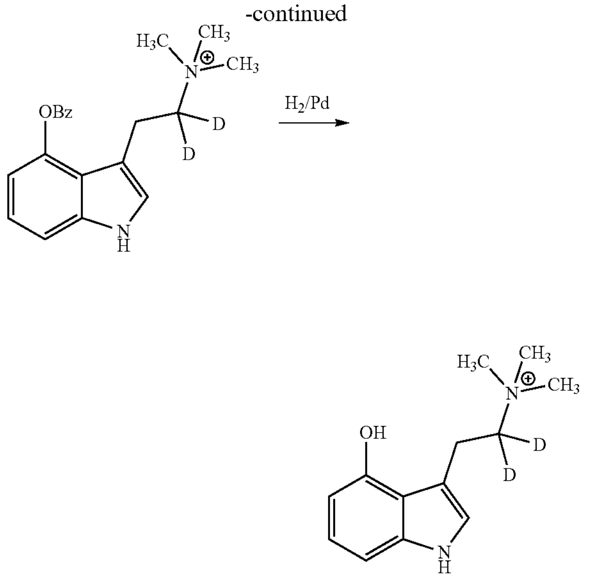

Example 5. 5-HT Receptor Pharmacodynamics

Binding affinity ($K_i$) and functional potency ($EC_{50}$) values of PI and PI-α-$d_2$ are summarized in Table 1. Deuteration was found to have little effect on the affinity and function at key receptor targets.

Receptor Affinity Assays: 5-$HT_{1A}$, 5-$HT_{2(A,B,C)}$ receptor affinities were determined by radioligand competition binding. Membranes from CHO-K1 or HEK293 cells expressing serotonergic receptors were collected and incubated in assay buffer with $K_d$ concentrations of radioligands and tests compounds that compete for receptor binding sites. After equilibration, the reaction was terminated by collecting ligand-receptor-membrane complexes (Microbeta, PerkinElmer), and radioactivity was measured by a scintillation counter (Microbeta2, PerkinElmer). Data were fit to non-linear curves, and $K_i$ values were calculated per the Cheng-Prusoff equation.

Receptor Function Assays: 5-$HT_{1A}$ receptor-mediated Gi stimulation (reduction in cyclic adenosine monophosphate (cAMP) levels) and 5-$HT_{2(A,B,C)}$ receptor-mediated Gq stimulation (phosphoinositide hydrolysis leading to the production of inositol phosphate 1 (IP1))—canonical signaling pathways—were measured as previously described (Canal et al., 2013), for example, with a homogeneous time-resolved fluorescence (HTRF) capable microplate reader (e.g., Mithras LB 940. Berthold) using commercially-available kits employing Fluorescence Resonance Energy Transfer (FRET) technology (e.g., LANCE Ultra cAMP TR-FRET (PerkinElmer) and IP-One HTRF (Cisbio) kits). Briefly, CHO-K1 or HEK293 cells expressing serotonergic receptors were incubated with test compounds in stimulation buffer. After equilibration, the reaction was terminated with the donor and acceptor fluorescent conjugates in lysis buffer, and FRET was measured. Data were fit to non-linear curves to calculate potencies (e.g., $EC_{50}$) and efficacies (e.g., $E_{MAX}$), relative to positive controls (e.g., serotonin).

TABLE 1

| PI and PI-α,α-$d_2$ Affinities and Functions at Target Serotonin Receptors | | | | | | | | |
|---|---|---|---|---|---|---|---|---|
| | 5-$HT_{1A}$ | | 5-$HT_{2A}$ | | 5-$HT_{2B}$ | | 5-$HT_{2C}$ | |
| PI | 567[a] | N.R. | 107[b] | 45 | 5[a] | >20,000 | 140[b] | N.R. |
| PI-α,α-$d_2$ | 510[a] | 200 | 100[b] | 40 | 6[a] | >20,000 | 130[b] | 115 |

Pharmacodynamics of psilocin and deuteropsilocin at target serotonergic receptors suggest no significant changes in ligand-receptor interactions. Under each receptor, sub-columns report, in nM, $K_i$ (agonist[a]- or antagonist[b]-labeled) and $EC_{50}$ (canonical signaling pathways) values, respectively, based on assessment at human receptors. PI data are PDSP certified or from Blough et al., 2014, Rickli et al., 2016, or Almaula et al., 1996. N.R. = not reported.

Example 6. In Vitro Liver Metabolism and Kinetic Deuterium Isotope Effects

5-MeO-DMT and 5-MeO-DMT-α,α-$d_2$ (10 μl of 2 μM solution) were incubated in 200 μl of medium that consisted of 100 mg rat liver microsomes, NADPH regenerating system (1 mM NADP, 1 unit/ml of isocitrate dehydrogenase, 5 mM isocitric acid, 5 mM magnesium chloride), and 25 mM of phosphate buffer (pH 7.4). The reaction was terminated at different time points (0 to 60 min) by the addition of 300 μl of acetonitrile. For the analyses of products, the precipitated salts and proteins were spun out on a centrifuge, the residual solution diluted with 300 μl of water and injected into the LC/MS (Agilent 1200 system interfaced with an ABS Sciex 4000 QTRAP LC/MS/MS Mass Spectrometer). The metabolic stability was estimated by evaluating the rate of disappearance of the main parent peak. The observed collective kinetic deuterium isotope effect (the reaction rate decrease for deuterated vs. non-deuterated molecule) was substantial at 150-200%. Similar effects were observed in this assay for DMT vs. DMT-α,α-$d_2$ and DMT-α,α, β,β-$d_4$. Further enhancement of metabolic stability has been detected for DMT-$d_{10}$ that also showed a superiority in the MAO-A enzymatic assay highlighting additional deuteration effects of the —$N(CD_3)_2$ substituent.

TABLE 2

Results of the Determination of Metabolic Stability of Four Test Articles in the Presence of RLM

| Test Article | % Remaining of Initial 0 min | 5 min | 10 min | 20 min | 30 min | 60 min | 120 min | Half-life (min) | $CL_{int}$ (mL/min/mg protein)[a] |
|---|---|---|---|---|---|---|---|---|---|
| DMT | 100 | 65.2 | 52.2 | 41.0 | 33.2 | 17.4 | 4.07 | 18.2 | 0.0762 |
| DMT-$d_2$ | 100 | 67.5 | 56.6 | 48.8 | 43.3 | 32.0 | 21.5 | 37.0 | 0.0374 |
| DMT-$d_4$ | 100 | 70.7 | 59.6 | 51.8 | 46.3 | 34.2 | 23.7 | 42.1 | 0.0329 |
| DMT-$d_{10}$ | 100 | 72.5 | 62.2 | 55.2 | 50.9 | 39.6 | 29.4 | 55.6 | 0.0249 |

[a]Intrinsic clearance ($CL_{int}$) was calculated based on $CL_{int}$ = k/P, where k is the elimination rate constant and P is the protein concentration in the incubation.

TABLE 3

Results of the Determination of Metabolic Stability of Four Test Articles in the Presence of hrMAO-A

| Test Article | % Remaining of Initial 0 min | 5 min | 10 min | 20 min | 30 min | 60 min | 120 min | Half-life (min) | $CL_{int}$ (mL/min/mg protein)[a] |
|---|---|---|---|---|---|---|---|---|---|
| DMT | 100 | 96.3 | 90.7 | 64.8 | 49.4 | 18.1 | 3.95 | 27.2 | 0.638 |
| DMT-$d_2$ | 100 | 106 | 111 | 101 | 97.5 | 76.0 | 59.1 | >120 (137) | 0.126 |
| DMT-$d_4$ | 100 | 106 | 111 | 102 | 98.2 | 77.4 | 61.4 | >120 (145) | 0.119 |
| DMT-$d_{10}$ | 100 | 107 | 112 | 103 | 101 | 82.2 | 68.6 | >120 (180) | 0.0953 |

TABLE 4

Results of the Determination of Metabolic Stability of $d_8$ and $d_{10}$ Analogs of DMT in the Presence of RLM

| Test Article | % Remaining of Initial 0 min | 5 min | 10 min | 20 min | 30 min | 60 min | 120 min | Half-life (min) | $CL_{int}$ (mL/min/mg protein)[a] |
|---|---|---|---|---|---|---|---|---|---|
| DMT-$d_8$ | 100 | 69.8 | 55.9 | 44.0 | 39.2 | 29.7 | 22.7 | 30.5 | 0.0454 |
| DMT-$d_{10}$ | 100 | 69.3 | 56.0 | 44.9 | 39.3 | 30.5 | 23.6 | 32.2 | 0.0430 |
| Percent Ratio of $[d_{10}]/[d_8]$ | 100 | 99.3 | 100.2 | 101.9 | 100.2 | 102.6 | 103.8 | NA | NA |

TABLE 5

| Results of the Determination of Metabolic Stability of $d_8$ and $d_{10}$ Analogs of DMT in the Presence of hrMAO-A | | | | | | | | | |
|---|---|---|---|---|---|---|---|---|---|
| | % Remaining of Initial | | | | | | | Half-life | $CL_{int}$ (mL/min/mg |
| Test Article | 0 min | 5 min | 10 min | 20 min | 30 min | 60 min | 120 min | (min) | protein)[a] |
| DMT-$d_8$ | 100.0 | 99.1 | 94.9 | 95.1 | 91.2 | 80.3 | 63.9 | >120 (196) | 0.177 |
| DMT-$d_{10}$ | 100.0 | 99.0 | 94.9 | 95.4 | 91.4 | 81.5 | 65.8 | >120 (210) | 0.165 |
| Percent Ratio of $[d_{10}]/[d_8]$ | 100.0 | 99.9 | 100.0 | 100.4 | 100.2 | 101.6 | 102.9 | NA | NA |

Example 7. PK Studies in Rats and Mice

The key PK parameters (presented as a % change vs. non-deuterated materials) are presented in Table 3 to include half-life ($T_{1/2}$), area under the curve (AUC), bioavailability (F) and blood-to-plasma ration (BPR). Pharmacokinetics of the deuterated tryptamines was studied in rats. In a typical experiment, run as a cassette dosing, two groups of 5 Wistar female rats (200-250 g) with surgically inserted jugular vein catheter (Charles River, Andover, MA) were fasted for 12 h and then administered 5 mg/kg of the deuterated and 5 mg/kg of the related non-deuterated analog, by oral gavage or via a catheter for each group. At time points 0, 15, 30, 60 min, and 2, 4, 8, and 24 h, the resulting plasma was analyzed for the parent molecule using LC/MS spectroscopy. Two separate groups of 5 animals were used for determining blood-to-plasma ratio (BPR). Each group was sacrificed at time points 15 and 30 min, respectively, and the concentration of the parent drug was determined in the brain and plasma by LC/MS spectroscopy.

TABLE 6

| Deuterium Kinetic Isotope Effects (% change) for the Key PK Parameters. | | | | | |
|---|---|---|---|---|---|
| Compound | $T_{1/2}$ | AUC | F | BPR, 15 min | BPR, 30 min |
| PI-α-$d_2$ | 50 | 75 | 45 | 100 | 150 |
| 5-MeO-DMT-α,α-$d_2$ | 30 | 60 | 200 | 120 | 180 |

Example 8. In Vitro Enzymatic Assays

The metabolic consequences of selective deuteration of tryptamine-based compounds were ascertained in two in vitro assays, i.e., monoamine oxidase A (MAO-A) and rat liver microsomes (RLM). Rat liver microsomal assays are considered a good proxy of the in vivo liver metabolism controlling the metabolic fate of tryptamines. Similar outcomes of deuteration have been detected in the in vitro assay of different animal species including human liver microsomes.

Without being bound to any particular theory, it is hypothesized that the major metabolic degradation pathway involving tryptamines, especially the exocyclic side chain of tryptamines, is controlled by the MAO-A enzymes. Consequently, for certain molecules, it is believed that specific deuteration in the exocyclic moiety of tryptamines (like the N—$CH_2$ fragment) can make a significant impact on the overall metabolic kinetics, i.e., the significant slowing of enzymatic degradation of the tryptamine derivatives discussed herein. In these instances, increased metabolic stabilities in both MAO-A and RLM assays were observed relative to the base nondeuterated compounds. In absence of MAO-A metabolism, deuteration of the N—$CH_2$ group had no impact on the RLM digest kinetics. No metabolism of tryptamines by MAO-B enzyme was observed.

Test results are summarized in Table 7 that established a set of exemplary compounds suitable for selective deuteration of the N—$CH_2$ fragment and also provided additional information regarding selective deuteration in other parts of the molecules. Comparison between the compounds was made using a best-fit curve to calculate half-life, i.e., a time point where 50% of the compound is digested in the assay.

hrMAO-A (Lot #8213001) and the hrMAO control (Lot #1067001) were purchased from XenoTech. The reaction mixture was prepared as described below. The co-dosed TAs were added into the reaction mixture at a final concentration of 1 microM each. The positive control, kynuramine (25 microM), was run simultaneously with the TAs in a separate reaction. The reaction mixture (without TAs or kynuramine) was equilibrated in a shaking water bath at 37° C. for 5 minutes. The reaction was initiated by the addition of the TAs or kynuramine, and the mixture was incubated in a shaking water bath at 37° C. Aliquots (100 microL) of the TA reaction mixture were withdrawn at 0, 5, 10, 20, 30, 60, and 120 minutes. Aliquots (100 microL) of the positive control reaction mixture were withdrawn at 0 and 30 minutes. TA and kynuramine samples were immediately combined with 100 microL of ice-cold 100% MeCN containing 0.1% formic acid and IS to terminate the reaction. The samples were then mixed and centrifuged to precipitate proteins. All TA samples were assayed by LC-HRAMS. The PARR (analyte to IS) at each time point was compared to the PARR at time 0 to determine the percent remaining at each time point. Reaction composition: hrMAO 0.02 mg/mL; Potassium Phosphate, pH 7.4 100 mM; Magnesium Chloride 5 mM; Test Articles (each) 1 microM.

Substrates were incubated in 200 μl of medium that consisted of 100 mg rat liver microsomes, NADPH regenerating system (1 mM NADP, 1 unit/ml of isocitrate dehydrogenase, 5 mM isocitric acid, 5 mM magnesium chloride), and 25 mM of phosphate buffer (pH 7.4). The reaction was terminated at different time points (0, 5, 10, 20, 30, 60, and 120 minutes) by the addition of 300 μl of acetonitrile. For the analyses of products, the precipitated salts and proteins were spun out on a centrifuge, the residual solution diluted with 300 μl of water and injected into the LC/MS (Agilent 1200 system interfaced with an ABS Sciex 4000 QTRAP LC/MS/MS Mass Spectrometer). The metabolic stability was estimated by evaluating the rate of disappearance of the main parent peak.

TABLE 7

Results of in vitro MAO-A and RLM assays

| $R_8$ | $R_9$ | $R_2$ | $R_4$ | $R_5$ | $R_6$ | $R_7$ | $X_{1,2}$ | $Y_{1,2}$ | MAO, % | RLM, % |
|---|---|---|---|---|---|---|---|---|---|---|
| Nor-Tryptamines | | | | | | | | | | |
| $CH_3$ | H | H | H | H | H | H | H,H | H,H | R | R |
| $CH_3$ | H | H | H | H | H | H | D,D | D,D | 622 | 189 |
| $CH_3$ | H | H | H | H | H | H | D,D | H,H | 578 | 182 |
| $CD_3$ | H | H | H | H | H | H | D,D | D,D | 711 | 214 |
| $CD_3$ | H | H | H | H | H | H | D,D | H,H | 744 | 207 |
| $C_2H_5$ | H | H | H | H | H | H | H,H | H,H | R | R |
| $C_2H_5$ | H | H | H | H | H | H | D,D | D,D | 140 | 142 |
| $C_2H_5$ | H | H | H | H | H | H | D,D | H,H | 145 | 138 |
| $C_2D_5$ | H | H | H | H | H | H | D,D | D,D | 166 | 159 |
| $C_2D_5$ | H | H | H | H | H | H | D,D | H,H | 170 | 151 |
| i-$C_3H_7$ | H | H | H | H | H | H | H,H | H,H | NR | R |
| i-$C_3H_7$ | H | H | H | H | H | H | D,D | D,D | NR | [106] |
| i-$C_3H_7$ | D | D | D | D | D | D | H,H | H,H | NR | 145 |
| Allyl | H | H | H | H | H | H | H,H | H,H | NR | R |
| 4-OH-Nor-Tryptamines | | | | | | | | | | |
| $CH_3$ | H | H | OH | H | H | H | H,H | H,H | R | R |
| $CH_3$ | H | H | OH | H | H | H | D,D | D,D | 396 | 160 |
| $CH_3$ | H | H | OH | H | H | H | D,D | H,H | 395 | 154 |
| $CD_3$ | H | H | OH | H | H | H | D,D | D,D | 459 | 173 |
| $CD_3$ | H | H | OH | H | H | H | D,D | H,H | 466 | 163 |
| $C_2H_5$ | H | H | OH | H | H | H | H,H | H,H | NR | R |
| $C_2H_5$ | H | H | OH | H | H | H | D,D | D,D | NR | [94] |
| $C_2D_5$ | H | H | OH | H | H | H | D,D | D,D | NR | [93] |
| $C_2H_5$ | D | D | OH | D | H | H | H,H | H,H | NR | R |
| i-$C_3H_7$ | H | H | OH | H | H | H | H,H | H,H | NR | R |
| i-$C_3H_7$ | H | H | OH | H | H | H | D,D | D,D | NR | [108] |
| i-$C_3H_7$ | D | D | OH | D | D | D | H,H | H,H | NR | 131 |
| N,N-Dialkyl Tryptamines | | | | | | | | | | |
| $CH_3$ | $C_2H_5$ | H | H | H | H | H | H,H | H,H | R | R |
| $CH_3$ | $C_2H_5$ | H | H | H | H | H | D,D | D,D | 162 | 131 |
| $CH_3$ | $C_2H_5$ | H | H | H | H | H | D,D | H,H | 168 | 121 |
| $C_2H_5$ | $C_2H_5$ | H | H | H | H | H | H,H | H,H | NR | R |
| $C_2H_5$ | $C_2H_5$ | H | H | H | H | H | D,D | D,D | NR | [105] |
| Allyl | Allyl | H | H | H | H | H | H,H | H,H | NR | R |
| Allyl | Allyl | H | H | H | H | H | D,D | D,D | NR | [106] |
| i-$C_3H_7$ | i-$C_3H_7$ | H | OH | H | H | H | H,H | H,H | NR | R |
| i-$C_3H_7$ | i-$C_3H_7$ | H | OH | H | H | H | D,D | D,D | NR | [97] |
| i-$C_3H_7$ | i-$C_3H_7$ | D | OH | D | D | D | H,H | H,H | NR | 167 |
| 4-OMe Tryptamines | | | | | | | | | | |
| $CH_3$ | $CH_3$ | H | OCH3 | H | H | H | H,H | H,H | R | R |
| $CH_3$ | CH3 | H | OCH3 | H | H | H | D,D | D,D | 325 | 190 |
| $CH_3$ | CH3 | H | OCH3 | H | H | H | D,D | H,H | 335 | 185 |
| $CH_3$ | $C_2H_5$ | H | OCH3 | H | H | H | H,H | H,H | R | R |
| $CH_3$ | $C_2H_5$ | H | OCH3 | H | H | H | D,D | H,H | 281 | 163 |
| $CH_3$ | $C_2H_5$ | H | OCH3 | H | H | H | D,D | D,D | 291 | 161 |
| $C_2H_5$ | $C_2H_5$ | H | OCH3 | H | H | H | H,H | H,H | NR | R |
| 5-OH Tryptamines | | | | | | | | | | |
| $CH_3$ | $CH_3$ | H | H | OH | H | H | H,H | H,H | R | R |
| $CH_3$ | $CH_3$ | H | H | OH | H | H | D,D | D,D | 418 | 136 |
| $CH_3$ | $CH_3$ | H | H | OH | H | H | D,D | H,H | 415 | 133 |
| $CH_3$ | $C_2H_5$ | H | H | OH | H | H | H,H | H,H | R | R |
| $CH_3$ | $C_2H_5$ | H | H | OH | H | H | D,D | H,H | 173 | 132 |
| $CH_3$ | $C_2H_5$ | H | H | OH | H | H | D,D | D,D | 179 | 144 |
| $C_2H_5$ | $C_2H_5$ | H | H | OH | H | H | H,H | H,H | NR | R |
| $C_2H_5$ | $C_2H_5$ | H | H | OH | H | H | D,D | D,D | NR | [106] |
| 5-OMe Tryptamines | | | | | | | | | | |
| $CH_3$ | $CH_3$ | H | H | OCH3 | H | H | H,H | H,H | R | R |
| $CH_3$ | CH3 | H | H | OCH3 | H | H | D,D | H,H | 227 | 185 |
| $CH_3$ | CH3 | H | H | OCH3 | H | H | D,D | D,D | 229 | 184 |
| $CH_3$ | $C_2H_5$ | H | H | OCH3 | H | H | H,H | H,H | R | R |
| $CH_3$ | $C_2H_5$ | H | H | OCH3 | H | H | D,D | D,D | 132 | 115 |
| $CH_3$ | $C_2H_5$ | H | H | OCH3 | H | H | D,D | H,H | 126 | 117 |
| $C_2H_5$ | $C_2H_5$ | H | H | OCH | H | H | H,H | H,H | NR | R |
| $C_2H_5$ | $C_2H_5$ | H | H | OCH3 | H | H | D,D | D,D | NR | [95] |
| $C_2H_5$ | $C_2H_5$ | D | D | OCH3 | D | D | H,H | H,H | NR | 172 |
| $CD_3$ | $CD_3$ | H | H | OCD3 | H | H | D,D | D,D | 372 | 299 |
| $CD_3$ | $CD_3$ | H | H | OCD3 | H | H | D,D | H,H | 366 | 288 |
| $CH_3$ | $CH_3$ | H | H | OCD3 | H | H | H,H | H,H | [109] | 151 |

TABLE 7-continued

| Results of in vitro MAO-A and RLM assays | | | | | | | | | | |
|---|---|---|---|---|---|---|---|---|---|---|
| $R_8$ | $R_9$ | $R_2$ | $R_4$ | $R_5$ | $R_6$ | $R_7$ | $X_{1,2}$ | $Y_{1,2}$ | MAO, % | RLM, % |
| DMT | | | | | | | | | | |
| $CH_3$ | $CH_3$ | D | D | D | D | D | H,H | H,H | [103] | [106] |
| $CH_3$ | $CH_3$ | D | D | D | D | D | D,D | D,D | 551 | 243 |
| $CD_3$ | $CD_3$ | D | D | D | D | D | D,D | D,D | 643 | 325 |

half-life differentiation in metabolic assays presented as % vs. the related nondeuterated compounds R means substantially metabolized NR means not metabolized at the last assay time point (120 min)

the values in square brackets are within 10% difference (assay's accuracy), indicative of no deuteration effect on metabolism As can be seen in Table 7, there is MAO-A metabolic activity for tryptamine-based substrates having N-Me and N-Et substituents, as well as the asymmetrically substituted like the N,N-Me,Et substituents, whereas no MAO-A metabolic activity was observed for a tryptamine-based substrate having a N,N-Et moiety. Consequently, tryptamine-based substrates with N,N-Et and higher alkyl chains, e.g., i-Pr and allyl, deuteration in the —N—$CH_2$—$CH_2$ and N—$R_8$, $R_9$ fragments had no metabolic consequences observed in both MAO-A and RLM assays. Tetra-deuteration of the ethylene bridge or selective bis-deuteration at the alpha carbon stabilized the substrates against MAO-A action compared to the metabolic activity for their base nondeuterated substrates, i.e., slowed down enzymatic degradation. Deuteration at the N—$R_8$, $R_9$ fragment further stabilized the substrates against MAO-A action as seen in Table 7. Perdeuterated DMT-dis, with additional deuteration in the phenyl ring provided no improvement in half-life compared to DMT-$d_{10}$ selectively deuterated at the exocyclic moiety observed in the RLM assay. However, it is observed that phenyl ring deuteration plays a role in slowing down RLM metabolism of the tryptamines that have no MAO-A metabolism. Without being bound to any particular theory, it is believed that there is a contribution to metabolism of tryptamine-based substrates from enzymes other than MAO like CYP isoforms to generate ring-hydroxylated metabolites. Involvement of the CYP enzymes is also believed to be involved in slowed RLM metabolism of the —OMe deuterated vs. non-deuterated 5-OMe substituted tryptamines.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

Accordingly, the preceding merely illustrates the principles of the methods and compositions. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the following.

What is claimed is:

1. A method of treating generalized anxiety disorder (GAD) in a subject, comprising administering to the subject a therapeutically effective amount of a compound, which is:

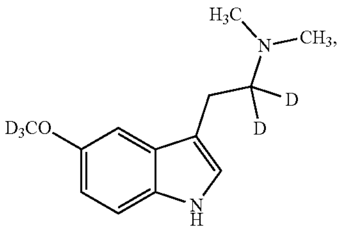

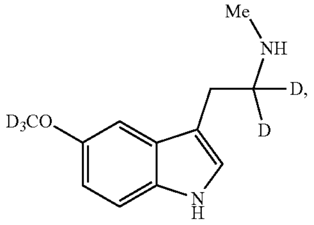

or a pharmaceutically acceptable salt, solvate, or prodrug thereof.

2. The method of claim 1, wherein the compound is

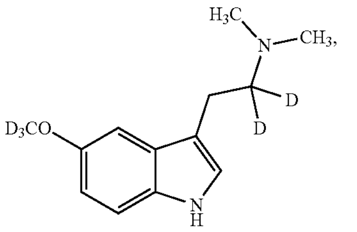

or a pharmaceutically acceptable salt or solvate thereof.

3. The method of claim 1, wherein the compound is a pharmaceutically acceptable salt of

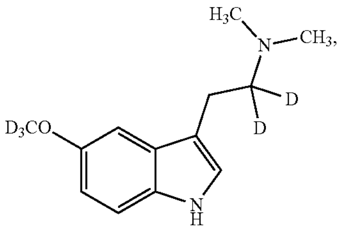

4. A method of treating major depressive disorder (MDD) and/or treatment-resistant depression (TRD) in a subject, comprising administering to the subject a therapeutically effective amount of a compound, which is:

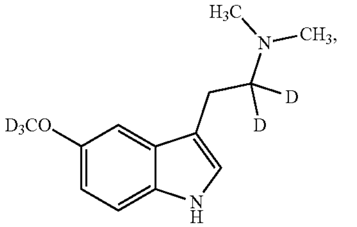

-continued

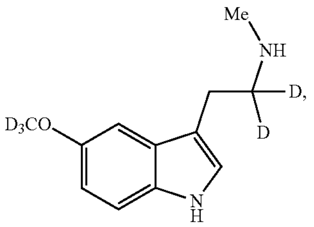

or a pharmaceutically acceptable salt, solvate, or prodrug thereof.

5. The method of claim 4, wherein the subject has major depressive disorder (MDD).

6. The method of claim 5, wherein the compound is

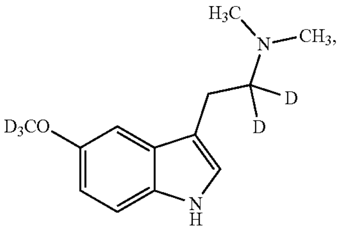

or a pharmaceutically acceptable salt or solvate thereof.

7. The method of claim 5, wherein the compound is a pharmaceutically acceptable salt of

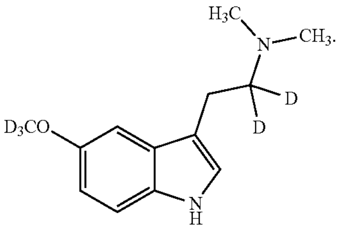

8. The method of claim 4, wherein the subject has treatment-resistant depression (TRD).

9. The method of claim 8, wherein the compound is

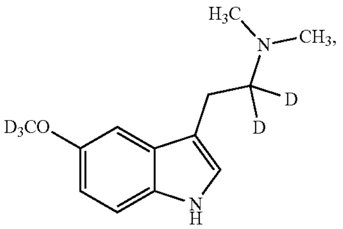

or a pharmaceutically acceptable salt or solvate thereof.

10. The method of claim 8, wherein the compound is a pharmaceutically acceptable salt of

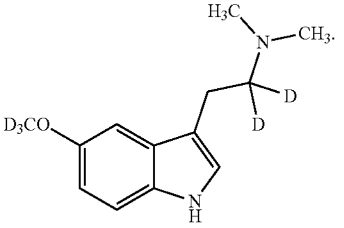

11. A method of treating a bipolar disorder in a subject, comprising administering to the subject a therapeutically effective amount of a compound, which is:

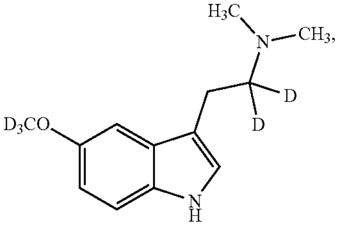

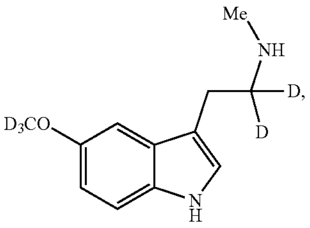

or a pharmaceutically acceptable salt, solvate, or prodrug thereof.

12. The method of claim 11, wherein the bipolar disorder is bipolar II disorder.

13. The method of claim 12, wherein the compound is

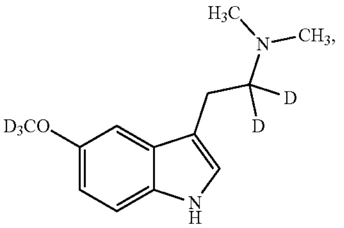

or a pharmaceutically acceptable salt or solvate thereof.

14. The method of claim 12, wherein the compound is a pharmaceutically acceptable salt of

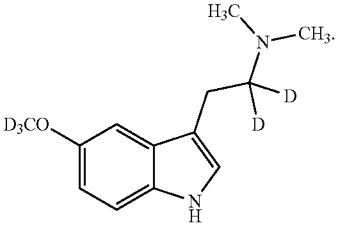

15. A method of treating a substance use disorder in a subject, comprising administering to the subject a therapeutically effective amount of a compound, which is:

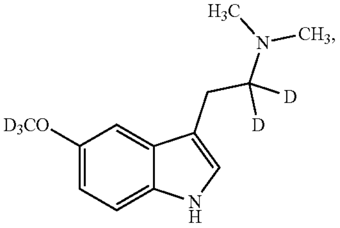

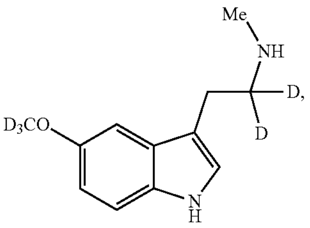

or a pharmaceutically acceptable salt, solvate, or prodrug thereof.

16. The method of claim 15, wherein the substance use disorder is alcohol use disorder.

17. The method of claim 16, wherein the compound is

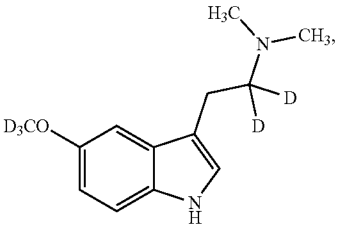

or a pharmaceutically acceptable salt or solvate thereof.

18. The method of claim 16, wherein the compound is a pharmaceutically acceptable salt of
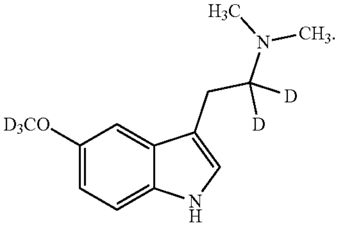
* * * * *